United States Patent
Eckhardt et al.

(10) Patent No.: US 8,609,690 B2
(45) Date of Patent: Dec. 17, 2013

(54) ARYL- AND HETEROARYLCARBONYL DERIVATIVES OF SUBSTITUTED NORTROPANES, MEDICAMENTS CONTAINING SUCH COMPOUNDS AND THEIR USE

(75) Inventors: Matthias Eckhardt, Biberach (DE); Bradford S. Hamilton, Biberach (DE); Frank Himmelsbach, Mittelbiberach (DE); Stefan Peters, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 227 days.

(21) Appl. No.: 13/059,233

(22) PCT Filed: Aug. 21, 2009

(86) PCT No.: PCT/EP2009/060820
§ 371 (c)(1),
(2), (4) Date: Jul. 29, 2011

(87) PCT Pub. No.: WO2010/023161
PCT Pub. Date: Mar. 4, 2010

(65) Prior Publication Data
US 2012/0115853 A1 May 10, 2012

(30) Foreign Application Priority Data
Aug. 25, 2008 (EP) .................... 08162899

(51) Int. Cl.
A61K 31/541 (2006.01)
C07D 451/02 (2006.01)
A61K 31/46 (2006.01)
A61K 31/498 (2006.01)
A61K 31/519 (2006.01)

(52) U.S. Cl.
USPC ............ 514/304; 514/3; 514/222.2; 514/249; 514/262.1; 514/265.1; 546/126; 546/132; 544/3; 544/263; 544/181; 544/353

(58) Field of Classification Search
USPC ................ 514/222.2, 249, 262.1, 265.1, 304; 546/126, 132; 544/3, 263, 281, 353
See application file for complete search history.

(56) References Cited

U.S. PATENT DOCUMENTS 6,525,059 B1 * 2/2003 Anantanarayan et al. .... 514/256
2006/0194780 A1   8/2006 Nargund et al.
2009/0170894 A1   7/2009 Aletru et al.

FOREIGN PATENT DOCUMENTS

WO 98/52940 * 11/1998
WO 2006044174 A2 4/2006
WO 2008000951 A2 1/2008

OTHER PUBLICATIONS

International Search Report and Written Opinion for PCT/EP2009/060820 mailed Dec. 3, 2009.
ChemAbstract—Accession No. 958599-31-0, Chemical Abstracts Service, Columbus, Ohio, Source: Emory MLSC database, Dec. 2007.
ChemAbstract—Accession No. 958625-83-7, Chemical Abstracts Service, Columbus, Ohio, Source: Emory MLSC database, Dec. 2007.
ChemAbstract—Accession No. 958629-14-6, Chemical Abstracts Service, Columbus, Ohio, Source: Emory MLSC database, Dec. 2007.
ChemAbstract—Accession No. 958629-22-6, Chemical Abstracts Service, Columbus, Ohio, Source: Emory MLSC database, Dec. 2007.
ChemAbstract—Accession No. 958629-39-5, Chemical Abstracts Service, Columbus, Ohio, Source: Emory MLSC database, Dec. 2007.
ChemAbstract—Accession No. 958696-32-7, Chemical Abstracts Service, Columbus, Ohio, Source: Emory MLSC database, Dec. 2007.
ChemAbstract—Accession No. 958696-39-4, Chemical Abstracts Service, Columbus, Ohio, Source: Emory MLSC database, Dec. 2007.
ChemAbstract—Accession No. 958700-63-5, Chemical Abstracts Service, Columbus, Ohio, Source: Emory MLSC database, Dec. 2007.

* cited by examiner

*Primary Examiner* — Niloofar Rahmani
(74) *Attorney, Agent, or Firm* — Michael P. Morris; David L. Kershner

(57) ABSTRACT

The present invention relates to compounds defined by formula (I) wherein the groups $R^1$ and $R^2$ are defined as in claim 1, possessing valuable pharmacological activity. Particularly the compounds are inhibitors of 11 β-hydroxysteroid dehydrogenase (HSD) 1 and thus are suitable for treatment and prevention of diseases which can be influenced by inhibition of this enzyme, such as metabolic diseases, in particular diabetes type 2, obesity, and dyslipidemia.

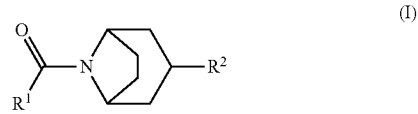

(I)

24 Claims, No Drawings

ARYL- AND HETEROARYLCARBONYL DERIVATIVES OF SUBSTITUTED NORTROPANES, MEDICAMENTS CONTAINING SUCH COMPOUNDS AND THEIR USE

The present invention relates to compounds derived from the following chemical scaffold which is structurally defined by the formula I

wherein the groups $R^1$ and $R^2$ are as defined hereinafter, including the tautomers, the stereoisomers, the mixtures thereof and the salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the enzyme 11β-hydroxysteroid dehydrogenase (HSD) 1 are proposed for the treatment of the metabolic syndrome, in particular diabetes type 2, obesity, and dyslipidemia.

In the international application WO 2006/044174 derivatives of nortropanes of the general formula

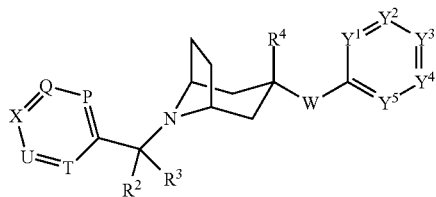

wherein $R^2$, $R^3$, $R^4$, W, $Y^1$ to $Y^5$, W, T, U, P, Q, and X are as defined therein, are described as ligands of the melanin concentrating hormone (MCH) receptor which may be used to modulate MCH binding to MCH receptors.

AIM OF THE INVENTION

The aim of the present invention is to find new nortropanes, particularly those which are active with regard to the enzyme 11β-hydroxysteroid dehydrogenase (HSD) 1. A further aim of the present invention is to discover nortropanes which have an inhibitory effect on the enzyme 11β-hydroxysteroid dehydrogenase (HSD) 1 in vitro and/or in vivo and possess suitable pharmacological and pharmacokinetic properties to use them as medicaments.

A further aim of the present invention is to provide new pharmaceutical compositions which are suitable for the prevention and/or treatment of metabolic disorders, particularly diabetes, obesity, and dyslipidemia.

Other aims of the present invention will become apparent to the skilled man directly from the foregoing and following remarks.

OBJECT OF THE INVENTION

In a first aspect the present invention relates to compounds which are structurally defined by the formula I

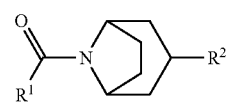

wherein
$R^1$ denotes phenyl, naphthyl,
  pyrrolyl, furanyl, thienyl, pyridinyl, indolyl, benzofuranyl, benzothiophenyl, quinolinyl, isoquinolinyl, or
  pyrrolyl, imidazolyl, furanyl, thienyl, pyridinyl, in each of which one or two CH groups are replaced by N, or
  indolyl, benzofuranyl, benzothiophenyl, quinolinyl, isoquinolinyl, in each of which 1 to 3 CH groups are replaced by N, or
  pyrazolopyrimidinyl, triazolopyrimidinyl,
  while in the above-mentioned N-heteroaromatic groups one or two —N=CH— groups are optionally replaced by —NH—CO— and/or —N($C_{1-4}$-alkyl)-CO—, and
  while the above-mentioned polycyclic aromatic and heteroaromatic groups are optionally partially saturated, though, retaining an aromatic or heteroaromatic substructure that is attached to the carbonyl group in formula I,
    where in the partially saturated rings one or two $CH_2$ groups optionally are independently replaced by oxygen, sulfur, NH, N($C_{1-4}$-alkyl), carbonyl, or sulfonyl,
  wherein the above-mentioned aromatic, heteroaromatic, partially saturated aromatic and heteroaromatic groups are optionally substituted with one or more, preferably one to four, substituents $R^4$, and wherein 2 adjacent C-atoms of each of said rings are optionally substituted with $R^5$ and $R^6$, and
  wherein all heteroaromatic rings are attached to the carbonyl group in formula I via a carbon atom,
$R^2$ denotes phenyl, naphthyl,
  pyrrolyl, furanyl, thienyl, pyridinyl, indolyl, benzofuranyl, benzothiophenyl, quinolinyl, isoquinolinyl, or
  pyrrolyl, imidazolyl, furanyl, thienyl, pyridinyl, in each of which one or two CH groups are replaced by N, or
  indolyl, benzofuranyl, benzothiophenyl, quinolinyl, isoquinolinyl, in each of which 1 to 3 CH groups are replaced by N,
  while the above-mentioned aromatic and heteroaromatic groups are optionally substituted with one or more, preferably one to four, substituents $R^7$,
  wherein all heteroaromatic rings are attached to the nortropane skeleton in formula I via a carbon atom,
$R^4$ independently of each other denotes halogen, $C_{1-6}$-alkyl, $C_{2-6}$-alkenyl, $C_{2-6}$-alkynyl, hydroxy, $C_{1-4}$-alkyloxy,
  nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)piperazin-1-yl, $C_{1-3}$-alkyl-carbonylamino, (het)aryl-carbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonyl-amino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonyl-amino, piperidin-1-yl-sulfonylamino, morpholin-4-yl-sulfonylamino, piperazin-1-yl-sulfonylamino, 4-($C_{1-3}$-alkyl)piperazin-1-yl-sulfonylamino, ($C_{1-3}$-alkyloxy-carbonyl-amino)carbonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkylaminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, N-($C_{1-3}$-alkyl)-(het)aryl-$C_{1-3}$-alkyksulfonylamino, oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl, 1,1-dioxothiazinanyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, (het)aryl-aminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkylsulfinyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, thietan-3-yloxy, while the above-mentioned $C_{3-n}$-cycloalkyl and $C_{3-n}$-cycloheteroalkyl groups are optionally substituted with one or two groups independently selected from fluorine, $C_{1-3}$-alkyl, $C_{1-3}$-alkoxy, $C_{1-3}$-alkoxy-$C_{1-3}$-alkyl, or hydroxy, and wherein one $CH_2$ group is optionally replaced by CO or $SO_2$, and $R^5$ and $R^6$ are linked to each other and bound to adjacent carbon atoms and form together a methylenedioxy, ethylenedioxy, or $C_{3-5}$-alkylene bridging group, which may be mono- or disubstituted with fluorine and/or methyl; or $R^5$ and $R^6$ may form combined with the carbon atoms they are attached to a benzo, pyrido, pyrimido, pyrrolo, furano, thieno, pyrazolo, imidazo, oxazolo, thiazolo, isoxazolo, or isothiazolo ring, wherein each of said rings is optionally substituted with one or more, preferably one to four, substituents independently of each other selected from halogen, $C_{1-3}$-alkyl, trifluoromethyl, amino, $C_{1-3}$-alkylamino, di-($C_{1-3}$-alkyl)amino, $C_{1-3}$-alkylcarbonylamino, hydroxy, cyano, carboxy, $C_{1-3}$-alkyloxycarbonyl, and $C_{1-3}$-alkyloxy, $R^7$ independently of each other denotes halogen, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, $C_{1-6}$-alkyl, $C_{2-6}$-alkenyl, $C_{2-6}$-alkynyl, $C_{1-4}$-alkyloxy, where in each group optionally one $CH_2$ group is replaced by carbonyl or sulfonyl and each of which is optionally mono- or polyfluorinated and optionally mono- or disubstituted with hydroxy, chlorine, $C_{1-3}$-alkyloxy, amino, $C_{1-3}$-alkylamino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 2-oxo-4-($C_{1-3}$-alkyl)-piperazin-1-yl, 3-oxo-4-($C_{1-3}$-alkyl)piperazin-1-yl, carboxy, $C_{1-3}$-alkyloxy-carbonyl, cyano, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, $C_{1-3}$-alkyl-carbonylamino, arylcarbonylamino, $C_{1-3}$-alkylsulfanyl, $C_{1-3}$-alkylsulfinyl, $C_{1-3}$-alkylsulfonyl, $C_{3-6}$-cycloalkyl, (het)aryl, or (het)aryloxy;

amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-4}$-alkyl-carbonylamino, (het)aryl-carbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonyl-amino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonyl-amino, piperidin-1-yl-sulfonylamino, morpholin-4-yl-sulfonylamino, piperazin-1-yl-sulfonylamino, 4-($C_{1-3}$-alkyl)piperazin-1-yl-sulfonylamino, ($C_{1-3}$-alkyloxy-carbonyl-amino)carbonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkylaminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkylsulfonylamino, N-($C_{1-3}$-alkyl)-(het)arylsulfonylamino, N-($C_{1-3}$-alkyl)-(het)aryl-$C_{1-3}$-alkyksulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, (het)aryl-aminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-3}$-alkylsulfanyl, $C_{1-3}$-alkysulfinyl, (het)arylsulfonyl, trifluoromethylsulfanyl, trifluoromethylsulfinyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)piperazin-1-yl-sulfonyl, wherein the above-mentioned $C_{3-n}$-cycloalkyl and $C_{3-n}$-cycloheteroalkyl groups are optionally substituted with one or two groups independently selected from fluorine, $C_{1-3}$-alkyl, $C_{1-3}$-alkoxy, $C_{1-3}$-alkoxy-$C_{1-3}$-alkyl, or hydroxy, and wherein one $CH_2$ group is optionally replaced by CO or $SO_2$, and $R^{11}$ independently of each other denotes halogen, $C_{1-4}$-alkyl, difluoromethyl, trifluoromethyl, cyano, nitro, amino, $C_{1-3}$-alkylcarbonylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, $C_{1-3}$-alkylaminosulfonyl, di-($C_{1-3}$-alkyl)-aminosulfonyl, $C_{1-3}$-alkylsulfanyl, $C_{1-3}$-alkylsulfinyl, $C_{1-3}$-alkylsulfonyl, hydroxy, $C_{1-3}$-alkyloxy, difluoromethoxy, trifluoromethoxy, phenyl, while the above-mentioned (het)aryl is phenyl, naphthyl, pyrrolyl, furanyl, thienyl, pyridyl, indolyl, benzofuranyl, benzothiophenyl, quinolinyl, isoquinolinyl, or pyrrolyl, furanyl, thienyl, imidazolyl, pyridyl in which 1 or 2 CH are replaced by N, or indolyl, benzofuranyl, benzothiophenyl, quinolinyl, isoquinolinyl in which 1 to 3 CH are replaced by N, or a ring selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxoquinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl and 3,4-dihydro-3-oxo-2H-benzo[1,4]oxazinyl, wherein each above-mentioned (het)aryl is optionally substituted with 1, 2 or 3 $R^{11}$ which may be identical or different, whilst the above-mentioned alkyl or alkylene moieties may be branched or unbranched, the tautomers thereof, the stereoisomers thereof, the mixtures thereof, and the salts thereof.

A preferred embodiment of this invention is described by formula I, wherein $R^1$ denotes phenyl, naphthyl, pyrrolyl, furanyl, thienyl, pyridinyl, indolyl, benzofuranyl, benzothio phenyl, quinolinyl, isoquinolinyl, or pyrrolyl, furanyl, thienyl, pyridinyl wherein 1 or 2 CH are replaced by N, or indolyl, benzofuranyl, benzothiophenyl, quinolinyl, isoquinolinyl, wherein 1 or 2 CH are replaced by N, or indolinyl, 2-oxo-2,3-dihydro-indolyl, 1-oxo-2,3-dihydro-isoindolyl, 2-oxo-2,3-dihydro-benzoimidazolyl, pyrazolo[1,5-a]pyrimidinyl, 7-oxo-4,7-dihydro-pyrazolo[1,5-a]pyrimidinyl, [1,2,4]triazolo[1,5-a]pyrimidinyl, 4-oxo-3,4-dihydro-quinazolinyl, tetrahydroquinolinyl, wherein the above-mentioned aromatic and heteroaromatic groups are optionally substituted with one or more, preferably one to four, substituents $R^4$ and wherein 2 adjacent C-atoms are optionally substituted with $R^5$ and $R^6$.

Another preferred embodiment of this invention is described by formula I, wherein $R^1$ denotes phenyl, naphthyl, furanyl, thienyl, pyrazolyl, oxazolyl, thiazolyl, isothiazolyl, [1,2,5]-thiadiazolyl, pyridinyl, pyrimidinyl, pyrazinyl, pyridazinyl, benzofuranyl, indolyl, indolinyl, 2-oxo-2,3-dihydro-indolyl, 1-oxo-2,3-dihydro-isoindolyl, indazolyl, benzimidazolyl, 2-oxo-2,3-dihydro-1H-benzoimidazolyl, benzoxazolyl, benzotriazolyl, benzothiazolyl, pyrazolo[1,5-a]
pyrimidinyl, 7-oxo-4,7-dihydro-pyrazolo[1,5-a]pyrimidinyl,
quinoxalinyl, quinolinyl, isoquinolinyl, quinazolinyl, 4-oxo-
3,4-dihydro-quinazolinyl, naphthyridinyl, and 1,2,3,4-tetrahydroquinolinyl, each of these groups is optionally substituted with one or more, preferably one to four, substituents $R^4$ and/or at 2 adjacent C-atoms with $R^5$ and $R^6$.

Another preferred embodiment of this invention is described by formula I, wherein $R^1$ denotes phenyl, furanyl, thienyl, pyrazolyl, thiazolyl, pyridinyl, benzofuranyl, indolyl, indolinyl, 2-oxo-2,3-dihydro-1H-indolyl, 1-oxo-2,3-dihydro-1H-isoindolyl, indazolyl, benzimidazolyl, 2-oxo-2,3-dihydro-1H-benzoimidazolyl, benzotriazolyl, benzothiazolyl, quinoxalinyl, quinolinyl, isoquinolinyl, 4-oxo-3,4-dihydro-quinazolinyl, and 1,2,3,4-tetrahydroquinolinyl, each of these groups is optionally substituted with one to four substituents $R^4$ and/or at 2 adjacent C-atoms with $R^5$ and $R^6$.

Another preferred embodiment of this invention is described by formula I, wherein $R^1$ denotes phenyl, benzofuranyl, indolyl, 2-oxo-2,3-dihydro-1H-indolyl, indazolyl, benzimidazolyl, benzotriazolyl, benzothiazolyl, quinoxalinyl, quinolinyl, and 1,2,3,4-tetrahydroquinolinyl, each of these groups is optionally substituted with one, two, or three substituents $R^4$ or optionally substituted with one or two substituents $R^4$ and/or at 2 adjacent C-atoms with $R^5$ and $R^6$.

Another preferred embodiment of this invention is described by formula I, wherein $R^2$ denotes phenyl, naphthyl, pyrrolyl, furanyl, thienyl, pyridinyl, indolyl, benzofuranyl, benzothiophenyl, quinolinyl, isoquinolinyl, or pyrrolyl, furanyl, thienyl, pyridinyl wherein 1 or 2 CH are replaced by N, or indolyl, benzofuranyl, benzothiophenyl, quinolinyl, isoquinolinyl, wherein 1 or 2 CH are replaced by N, while the above-mentioned aromatic and heteroaromatic rings are optionally substituted with one to four $R^7$.

Another preferred embodiment of this invention is described by formula I, wherein $R^2$ denotes phenyl, naphthyl, furanyl, pyridinyl, pyrimidinyl, pyrazinyl, pyridazinyl, indoly, benzimidazolyl, benzoxazolyl, quinolinyl, or isoquinolinyl, wherein each of these groups is optionally substituted with one, two, or three $R^7$.

Another preferred embodiment of this invention is described by formula I, wherein $R^2$ denotes phenyl, naphthyl, or pyridinyl that are optionally substituted with one, two, or three $R^7$.

Another preferred embodiment of this invention is described by formula I, wherein $R^2$ denotes phenyl optionally substituted with one or two $R^7$.

Another preferred embodiment of this invention is described by formula I, wherein $R^4$ denotes fluorine, chlorine, bromine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxycarbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, N-($C_{1-3}$-alkyl)-(het)aryl-$C_{1-3}$-alkyl-sulfonylamino, oxo-imidazolidinyl, 2,4-dioxo-imidazolidinyl, 2,5-dioxo-imidazolidin-1-yl, 2-oxo-hexahydropyrimidin-1-yl, wherein the nitrogen atom in position 3 of the aforementioned groups is optionally substituted with methyl, 1,1-dioxo-[1,2]thiazinan-2-yl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxomorpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, thietan-3-yloxy, wherein the above-mentioned (het)aryl groups are phenyl, naphthyl, or pyrrolyl, furanyl, thienyl, pyridyl, indolyl, benzofuranyl, benzothiophenyl, quinolinyl, isoquinolinyl, or pyrrolyl, furanyl, thienyl, imidazolyl, pyridyl wherein 1 or 2 CH are replaced by N, or indolyl, benzofuranyl, benzothiophenyl, quinolinyl, isoquinolinyl wherein 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, 3,4-dihydro-3-oxo-2H-benzo[1,4]oxazinyl, and wherein all the above-mentioned (het)aryl groups are optionally substituted with 1, 2 or 3 $R^{11}$ which may be identical or different.

Another preferred embodiment of this invention is described by formula I, wherein $R^4$ denotes fluorine, chlorine, bromine, $C_{1-4}$-alkyl, hydroxy, $C_{1-4}$-alkyloxy, thietan-3-yloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, 2-oxo-imidazolidinyl, 1,1-dioxo-[1,2]thiazinanyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, N-($C_{1-3}$-alkyl)-(het)arylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, $C_{1-3}$-alkylsulfonyl, aminosulfonyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, (het)aryl, (het)aryl-$C_{1-3}$-alkyl, or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, imidazolyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups are optionally substituted with 1, 2, or 3 $R^{11}$ which may be identical or different.

Another preferred embodiment of this invention is described by formula I, wherein $R^4$ denotes fluorine, chlorine, $C_{1-4}$-alkyl, difluoromethyl, trifluoromethyl, hydroxy, $C_{1-4}$-alkyloxy, difluoromethoxy, trifluoromethoxy, thietan-3-yloxy, amino, $C_{1-3}$-alkylamino, di-($C_{1-3}$-alkyl)amino, pyrrolidin-1-yl, piperidin-1-yl, morpholin-4-yl, $C_{1-3}$-alkyl-carbonylamino, $C_{1-4}$-alkylcarbonyl, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, 2-oxo-pyrrolidin-1-yl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, morpholin-4-yl-$C_{1-3}$-alkyl, $C_{1-3}$-alkylcarbonyl-$C_{1-3}$-alkyl, $C_{1-3}$-alkylcarbonylamino-$C_{1-3}$-alkyl, 1,1-dioxo-[1,2]thiazinan-2-yl, 2-oxo-imidazolidinyl, $C_{1-3}$-alkylsulfonyl, aminosulfonyl, phenyl, pyrazolyl, oxazolyl, [1,2,4]oxadiazol-3-yl, or tetrazol-1-yl, while the aromatic and heteroaromatic groups listed are optionally substituted with 1, 2, or 3 groups $R^{11}$ which may be identical or different.

Another preferred embodiment of this invention is described by formula I, wherein $R^4$ denotes fluorine, chlorine, methyl, ethyl, iso-butyl, tert-butyl, difluoromethyl, trifluoromethyl, hydroxy, methoxy, tert-butyloxy, thietan-3-yloxy, amino, methylamino, acetylamino, hydroxymethyl, acetylaminomethyl, carboxy, cyano, methoxycarbonyl, aminocarbonyl, methylaminocarbonyl, 2-oxo-pyrrolidin-1-yl, methylcarbonyl, 2-oxo-imidazolidinyl, methylsulfonyl, aminosulfonyl, phenyl, pyrazol-3-yl, oxazol-5-yl, 5-methyl-[1,2,4]oxadiazol-3-yl, tetrazol-1-yl, or tetrazol-5-yl.

Another preferred embodiment of this invention is described by formula I, wherein $R^7$ denotes halogen, $C_{1-6}$-alkyl, $C_{2-6}$-alkenyl, $C_{2-6}$-alkynyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkylcarbonyl)piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)aryl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, $C_{1-3}$-alkyl-sulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, (het)arylsulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, (het)arylaminocarbonyl, N-($C_{1-3}$-alkyl)-(het)arylaminocarbonyl, (het)aryl-$C_{1-3}$-alkyl-aminocarbonyl, N-($C_{1-3}$-alkyl)-(het)aryl-$C_{1-3}$-alkylaminocarbonyl, $C_{1-4}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, 3-oxo-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, 3-oxo-piperazin-1-yl-$C_{1-3}$-alkyloxy, 3-oxo-4-($C_{1-3}$-alkyl)piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, wherein the above-mentioned (het)aryl is phenyl, naphthyl, pyrrolyl, furanyl, thienyl, pyridyl, or pyrrolyl, furanyl, thienyl, imidazolyl, pyridyl in which 1 or 2 CH are replaced by N, and wherein the above-mentioned (het)aryl groups are optionally substituted with one or two $R^{11}$ which may be identical or different.

Another preferred embodiment of this invention is described by formula I, wherein $R^7$ denotes denotes fluorine, chlorine, bromine, $C_{1-6}$-alkyl, $C_{2-6}$-alkenyl, $C_{2-6}$-alkynyl, hydroxy, $C_{1-4}$-alkyloxy, amino, $C_{1-3}$-alkylamino, di-($C_{1-3}$-alkyl)amino, $C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, $C_{1-3}$-alkyl-sulfonylamino, N-($C_{1-3}$-alkyl)-$C_{1-3}$-alkyl-carbonylamino, N-($C_{1-3}$-alkyl)-$C_{1-3}$-alkyl-sulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfonyl, trifluoromethylsulfonyl, aminosulfonyl, $C_{1-3}$-alkyl-aminosulfonyl, di-($C_{1-3}$-alkyl)-aminosulfonyl, difluoromethyl, trifluoromethyl, difluoromethoxy, trifluoromethoxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, or phenyl or phenoxy that are optionally substituted with one or two identical or different $R^{11}$.

Another preferred embodiment of this invention is described by formula I, wherein $R^7$ denotes fluorine, chlorine, bromine, $C_{1-4}$-alkyl, trifluoromethyl, hydroxy, $C_{1-4}$-alkyloxy, trifluoromethoxy, phenoxy, amino-$C_{1-3}$-alkyl, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, or phenyl.

Another preferred embodiment of this invention is described by formula I, wherein $R^7$ denotes fluorine, chlorine, bromine, methyl, isopropyl, trifluoromethyl, hydroxy, methoxy, trifluoromethoxy, phenoxy, aminomethyl, carboxy, methoxycarbonyl, aminocarbonyl, or phenyl.

The compounds of general formula I according to the invention and the physiologically acceptable salts thereof have valuable pharmacological properties, particularly an inhibitory effect on the enzyme 11β-hydroxysteroid dehydrogenase (HSD) 1.

The first aspect of the invention also relates to the physiologically acceptable salts of the compounds of general formula I with inorganic or organic acids.

In a second aspect this invention relates to pharmaceutical compositions, containing at least one compound of general formula I or a physiologically acceptable salt according to the invention, optionally together with one or more inert carriers and/or diluents.

In a third aspect this invention relates to the compounds according to general formula I or the physiologically acceptable salts thereof for treatment or prevention of diseases or conditions which can be influenced by inhibiting the enzyme 11β-hydroxysteroid dehydrogenase (HSD) 1, such as metabolic disorders.

In a fourth aspect this invention relates to the use of at least one compound according to general formula I or one of the physiologically acceptable salts thereof for preparing a pharmaceutical composition which is suitable for the treatment or prevention of diseases or conditions which can be influenced by inhibiting the enzyme 11β-hydroxysteroid dehydrogenase (HSD) 1, such as metabolic disorders.

In a fifth aspect the invention relates to a process for preparing a pharmaceutical composition according to the invention, characterized in that a compound of general formula I or one of the physiologically acceptable salts thereof is incorporated in one or more inert carriers and/or diluents by a non-chemical method.

In a sixth aspect the present invention relates to a process for preparing the compounds of general formula I, characterized in that in order to prepare compounds of general formula I which are defined as hereinbefore and hereinafter, a compound of general formula II

II wherein the group $R^2$ is defined as hereinbefore and hereinafter;

is reacted with a compound of general formula $R^1$—CO—Y, optionally prepared in situ from the corresponding carboxylic acid, wherein $R^1$ is defined as hereinbefore and hereinafter and Y is a leaving group and in particular denotes fluorine, chlorine, bromine, cyano, $C_{1-4}$-alkoxy, $C_{2-4}$-alkenyloxy, $C_{2-4}$-alkynyloxy, $C_{1-4}$-alkylsulfanyl, arylotriazoloxy, heteroarylotriazoloxy, heteroaryl, succinyl-N-oxy, $C_{1-4}$-alkylcarbonyloxy, di-($C_{1-4}$-alkyl)aminocarbonyloxy, pyrrolylcarbonyloxy, piperidinylcarbonyloxy, morpholinylcarbonyloxy, tri-($C_{1-4}$-alkyl)-carbamimidoyloxy, N,N,N',N'-tetra-($C_{1-4}$-alkyl)uronyl, N,N'-dicyclohexyluronyl, di-($C_{1-4}$-alkyloxy)-phosphoryloxy, di-(di-$C_{1-4}$-alkylamino)-phosphoryloxy, dipyrrolidinylphosphoryloxy, aryloxy, arylsulfanyl, heterosulfanyl, or heteroaryloxy, while the alkyl, alkenyl, and alkynyl groups mentioned in the definition of the above groups optionally are mono- or polysubstituted with fluorine, chlorine, $C_{1-3}$-alkyl, or $C_{1-3}$-alkoxy, while the aryl groups mentioned in the definition of the above groups, either alone or as part of another group, denote phenyl or naphthyl groups and the heteroaryl groups mentioned in the definition of the above groups, either alone or as part of another group, denote pyridinyl, pyrimidinyl, triazinyl, imidazolyl, pyrazolyl, triazolyl, tetrazolyl, whilst both the aryl and heteroaryl groups optionally are independently mono- or polysubstituted with fluorine, chlorine, bromine, $C_{1-3}$-alkyl, $C_{1-3}$-alkyloxy, nitro, cyano, or di-($C_{1-3}$-alkyl)amino groups, optionally in the presence of a base or another additive;

and if necessary any protective group used in the reactions described above is cleaved concurrently or subsequently;

if desired a compound of general formula I thus obtained is resolved into its stereoisomers;

if desired a compound of general formula I thus obtained is converted into the salts thereof, particularly for pharmaceutical use into the physiologically acceptable salts thereof.

DETAILED DESCRIPTION OF THE INVENTION

Unless otherwise stated, the groups, residues, and substituents, particularly $R^1$, $R^2$, $R^4$, $R^5$, $R^6$, $R^7$, and $R^{11}$ are defined as above and hereinafter. If residues, substituents, or groups occur several times in a compound they may have the same or different meanings. Some preferred meanings of groups and substituents of the compounds according to the invention will be given hereinafter.

Preferred embodiments of the invention are characterized by the following definitions:

a) Definitions ($a^i$) for $R^1$ in the order of preference, ascending from preferably ($a^1$) to more preferably ($a^2$) up to most preferably ($a^4$):

($a^1$): Preferably, $R^1$ denotes phenyl, naphthyl, pyrrolyl, furanyl, thienyl, pyridinyl, indolyl, benzofuranyl, benzothiophenyl, quinolinyl, isoquinolinyl, or pyrrolyl, furanyl, thienyl, pyridinyl wherein 1 or 2 CH are replaced by N, or indolyl, benzofuranyl, benzothiophenyl, quinolinyl, isoquinolinyl, wherein 1 or 2 CH are replaced by N, or indolinyl, 2-oxo-2,3-dihydro-indolyl, 1-oxo-2,3-dihydro-isoindolyl, 2-oxo-2,3-dihydro-benzoimidazolyl, pyrazolo[1,5-a]pyrimidinyl, 7-oxo-4,7-dihydro-pyrazolo[1,5-a]pyrimidinyl, [1,2,4]triazolo[1,5-a]pyrimidinyl, 4-oxo-3,4-dihydro-quinazolinyl, tetrahydroquinolinyl, wherein the above-mentioned aromatic and heteroaromatic groups are optionally substituted with one or more, preferably one to four, substituents $R^4$ and wherein 2 adjacent C-atoms are optionally substituted with $R^5$ and $R^6$.

($a^2$): More preferably, $R^1$ denotes phenyl, naphthyl, furanyl, thienyl, pyrazolyl, oxazolyl, thiazolyl, isothiazolyl, [1,2,5]-thiadiazolyl, pyridinyl, pyrimidinyl, pyrazinyl, pyridazinyl, benzofuranyl, indolyl, indolinyl, 2-oxo-2,3-dihydro-indolyl, 1-oxo-2,3-dihydro-isoindolyl, indazolyl, benzimidazolyl, 2-oxo-2,3-dihydro-1H-benzoimidazolyl, benzoxazolyl, benzotriazolyl, benzothiazolyl, pyrazolo[1,5-a]pyrimidinyl, 7-oxo-4,7-dihydro-pyrazolo[1,5-a]pyrimidinyl, quinoxalinyl, quinolinyl, isoquinolinyl, quinazolinyl, 4-oxo-3,4-dihydro-quinazolinyl, naphthyridinyl, and 1,2,3,4-tetrahydroquinolinyl, each of these groups is optionally substituted with one or more, preferably one to four, substituents $R^4$ and/or at 2 adjacent C-atoms with $R^5$ and $R^6$.

($a^3$): Even more preferably, $R^1$ denotes phenyl, furanyl, thienyl, pyrazolyl, thiazolyl, pyridinyl, benzofuranyl, indolyl, indolinyl, 2-oxo-2,3-dihydro-1H-indolyl, 1-oxo-2,3-dihydro-1H-isoindolyl, indazolyl, benzimidazolyl, 2-oxo-2,3-dihydro-1H-benzoimidazolyl, benzotriazolyl, benzothiazolyl, quinoxalinyl, quinolinyl, isoquinolinyl, 4-oxo-3,4-dihydroquinazolinyl, and 1,2,3,4-tetrahydroquinolinyl, each of these groups is optionally substituted with one to four substituents $R^4$ and/or at 2 adjacent C-atoms with $R^5$ and $R^6$.

($a^4$): Most preferably, $R^1$ denotes phenyl, benzofuranyl, indolyl, 2-oxo-2,3-dihydro-1H-indolyl, indazolyl, benzimidazolyl, benzotriazolyl, benzothiazolyl, quinoxalinyl, quinolinyl, and 1,2,3,4-tetrahydroquinolinyl, each of these groups is optionally substituted with one, two, or three substituents $R^4$ or optionally substituted with one or two substituents $R^4$ and/or at 2 adjacent C-atoms with $R^5$ and $R^6$.

b) Definitions ($b^i$) for $R^2$ in the order of preference, ascending from preferably ($b^1$) to more preferably ($b^2$) up to most preferably ($b^4$):

($b^1$): Preferably, $R^2$ denotes phenyl, naphthyl, pyrrolyl, furanyl, thienyl, pyridinyl, indolyl, benzofuranyl, benzothiophenyl, quinolinyl, isoquinolinyl, or pyrrolyl, furanyl, thienyl, pyridinyl wherein 1 or 2 CH are replaced by N, or indolyl, benzofuranyl, benzothiophenyl, quinolinyl, isoquinolinyl, wherein 1 or 2 CH are replaced by N, while the above-mentioned aromatic and heteroaromatic rings are optionally substituted with one to four $R^7$.

($b^2$): More preferably, $R^2$ denotes phenyl, naphthyl, furanyl, pyridinyl, pyrimidinyl, pyrazinyl, pyridazinyl, indoly, benzimidazolyl, benzoxazolyl, quinolinyl, or isoquinolinyl, each of these groups is optionally substituted with one, two, or three $R^7$.

($b^3$): Even more preferably, $R^2$ denotes phenyl, naphthyl, or pyridinyl that are optionally substituted with one, two, or three $R^7$.

($b^4$): Most preferably, $R^2$ denotes phenyl optionally substituted with one or two $R^7$.

c) Definitions ($c^i$) for $R^4$ in the order of preference, ascending from preferably ($c^1$) to more preferably ($c^2$) up to most preferably ($c^4$):

($c^1$): Preferably, $R^4$ denotes fluorine, chlorine, bromine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, N-($C_{1-3}$-alkyl)-(het)aryl-$C_{1-3}$-alkyl-sulfonylamino, oxo-imidazolidinyl, 2,4-dioxo-imidazolidinyl, 2,5-dioxo-imidazolidin-1-yl, 2-oxo-hexahydropyrimidin-1-yl, wherein the nitrogen atom in position 3 of the aforementioned groups is optionally substituted with methyl, 1,1-dioxo-[1,2]thiazinan-2-yl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, thietan-3-yloxy, wherein the above-mentioned (het)aryl groups are phenyl, naphthyl, or pyrrolyl, furanyl, thienyl, pyridyl, indolyl, benzofuranyl, benzothiophenyl, quinolinyl, isoquinolinyl, or pyrrolyl, furanyl, thienyl, imidazolyl, pyridyl wherein 1 or 2 CH are replaced by N, or indolyl, benzofuranyl, benzothiophenyl, quinolinyl, isoquinolinyl wherein 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, 3,4-dihydro-3-oxo-2H-benzo[1,4]oxazinyl, and wherein all the above-mentioned (het)aryl groups are optionally substituted with 1, 2, or 3 $R^{11}$ which may be identical or different.

($c^2$): More preferably $R^4$ denotes fluorine, chlorine, bromine, $C_{1-4}$-alkyl, hydroxy, $C_{1-4}$-alkyloxy, thietan-3-yloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)piperazin-1-yl, $C_{1-3}$-alkyl-carbonylamino, (het)arylcarbonylamino, (het)aryl-$C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, 2-oxo-imidazolidinyl, 1,1-dioxo-[1,2]thiazinanyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, N-($C_{1-3}$-alkyl)-(het)arylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, $C_{1-3}$-alkylsulfonyl, aminosulfonyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, (het)aryl, (het)aryl-$C_{1-3}$-alkyl or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, imidazolyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups may be substituted with 1, 2, or 3 $R^{11}$ which may be identical or different.

($c^3$): Even more preferably, $R^4$ denotes fluorine, chlorine, $C_{1-4}$-alkyl, difluoromethyl, trifluoromethyl, hydroxy, $C_{1-4}$-alkyloxy, difluoromethoxy, trifluoromethoxy, thietan-3-yloxy, amino, $C_{1-3}$-alkylamino, di-($C_{1-3}$-alkyl)amino, pyrrolidin-1-yl, piperidin-1-yl, morpholin-4-yl, $C_{1-3}$-alkylcarbonylamino, $C_{1-4}$-alkylcarbonyl, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, 2-oxo-pyrrolidin-1-yl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, morpholin-4-yl-$C_{1-3}$-alkyl, $C_{1-3}$-alkylcarbonyl-$C_{1-3}$-alkyl, $C_{1-3}$-alkyl-carbonylamino-$C_{1-3}$-alkyl, 1,1-dioxo-

[1,2]thiazinan-2-yl, 2-oxo-imidazolidinyl, $C_{1-3}$-alkylsulfonyl, aminosulfonyl, phenyl, pyrazolyl, oxazolyl, [1,2,4] oxadiazol-3-yl, or tetrazol-1-yl, while the aromatic and heteroaromatic groups listed are optionally substituted with 1, 2, or 3 groups $R^{11}$ which may be identical or different.

($c^4$): Most preferably, $R^4$ denotes fluorine, chlorine, methyl, ethyl, iso-butyl, tert-butyl, difluoromethyl, trifluoromethyl, hydroxy, methoxy, tert-butyloxy, thietan-3-yloxy, amino, methylamino, acetylamino, hydroxymethyl, acetylaminomethyl, carboxy, cyano, methoxycarbonyl, aminocarbonyl, methylaminocarbonyl, 2-oxo-pyrrolidin-1-yl, methylcarbonyl, 2-oxo-imidazolidinyl, methylsulfonyl, aminosulfonyl, phenyl, pyrazol-3-yl, oxazol-5-yl, 5-methyl-[1,2,4]oxadiazol-3-yl, tetrazol-1-yl, or tetrazol-5-yl.

d) Definitions ($d^i$) for $R^5$ and $R^6$, which are linked and bound to adjacent carbon atoms, in the order of preference, ascending from preferably ($d^1$) to more preferably ($d^2$) up to most preferably ($d^3$):

($d^1$): Preferably, $R^5$ and $R^6$ form a methylenedioxy, difluoromethylenedioxy, ethylenedioxy, or $C_{3-5}$-alkylene group.

($d^2$): More preferably, $R^5$ and $R^6$ form a methylenedioxy, difluoromethylenedioxy, ethylenedioxy, propylene, or butylene group.

($d^3$): Most preferably, $R^5$ and $R^6$ form a methylenedioxy, difluoromethylenedioxy, or 1,2-ethylenedioxy group.

e) Definitions ($e^i$) for $R^7$ in the order of preference, ascending from preferably ($e^1$) to more preferably ($e^2$) up to most preferably ($e^4$):

($e^1$): Preferably, $R^7$ denotes halogen, $C_{1-6}$-alkyl, $C_m$-alkenyl, $C_{2-6}$-alkynyl, hydroxy, $C_{1-4}$-alkyloxy,
  nitro, amino, $C_{1-3}$-alkylamino, di-($C_{1-3}$-alkyl)amino, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl,
  $C_{1-3}$-alkyl-carbonylamino, (het)aryl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, $C_{1-3}$-alkyksulfonylamino, $C_{1-3}$-alkyl-amino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, (het)arylsulfonylamino,
  N-($C_{1-3}$-alkyl)-$C_{1-3}$-alkyl-carbonylamino, N-($C_{1-3}$-alkyl)-(het)arylcarbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino,
  N-($C_{1-3}$-alkyl)-$C_{1-3}$-alkyl-sulfonylamino, N-($C_{1-3}$-alkyl)-(het)arylsulfonylamino,
  cyano, carboxy, $C_{1-3}$-alkyloxy-carbonyl, aminocarbonyl, $C_{1-3}$-alkyl-aminocarbonyl, ($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)piperazin-1-yl-carbonyl, (het)arylaminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl,
  $C_{1-4}$-alkyl-carbonyl, (het)aryl-carbonyl,
  carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl,
  pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl,
  carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy,
  hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, 3-oxo-piperazin-1-yl-$C_{1-3}$-alkyl, 3-oxo-4-($C_{1-3}$-alkyl)-piperazin-1-yl-$C_{1-3}$-alkyl,
  $C_{1-3}$-alkylcarbonylamino-$C_{1-3}$-alkyl, arylcarbonylamino-$C_{1-3}$-alkyl,
  hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, 3-oxo-piperazin-1-yl-$C_{1-3}$-alkyloxy, 3-oxo-4-($C_{1-3}$-alkyl)piperazin-1-yl-$C_{1-3}$-alkyloxy,
  $C_{1-3}$-alkylsulfanyl, $C_{1-3}$-alkysulfinyl, $C_{1-3}$-alkylsulfonyl, (het)arylsulfonyl, trifluoromethylsulfinyl, trifluoromethylsulfonyl,
  aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl,
  difluoromethyl, trifluoromethyl, difluoromethoxy, trifluoromethoxy,
  $C_{3-6}$-cycloalkyl, $C_{3-6}$-cycloalkyloxy,
  $C_{3-6}$-cycloalkyl-$C_{1-3}$-alkyl, $C_{3-6}$-cycloalkyl-$C_{1-3}$-alkyloxy,
  (het)aryl, (het)aryloxy, (het)aryl-$C_{1-3}$-alkyl, (het)aryl-$C_{1-3}$-alkyloxy, (het)aryloxy-$C_{1-3}$-alkyl, or
  tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy,
  wherein the above-mentioned (het)aryl is phenyl, naphthyl, pyrrolyl, furanyl, thienyl, pyridyl, or
  pyrrolyl, furanyl, thienyl, imidazolyl, pyridyl in which 1 or 2 CH are replaced by N,
  and wherein the above-mentioned (het)aryl groups are optionally substituted with one or two $R^{11}$ which may be identical or different.

($e^2$): More preferably, $R^7$ denotes fluorine, chlorine, bromine, $C_{1-6}$-alkyl, $C_{2-6}$-alkenyl, $C_{2-6}$-alkynyl, hydroxy, $C_{1-4}$-alkyloxy,
  amino, $C_{1-3}$-alkylamino, di-($C_{1-3}$-alkyl)amino,
  $C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, $C_{1-3}$-alkyl-sulfonylamino,
  N-($C_{1-3}$-alkyl)-$C_{1-3}$-alkyl-carbonylamino, N-($C_{1-3}$-alkyl)-$C_{1-3}$-alkyl-sulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfonyl, trifluoromethylsulfonyl, aminosulfonyl, $C_{1-3}$-alkyl-aminosulfonyl, di-($C_{1-3}$-alkyl)-aminosulfonyl, difluoromethyl, trifluoromethyl, difluoromethoxy, trifluoromethoxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, or phenyl or phenoxy that are optionally substituted with one or two identical or different $R^{11}$.

($e^3$): Even more preferably, $R^7$ denotes fluorine, chlorine, bromine, $C_{1-4}$-alkyl, trifluoromethyl, hydroxy, $C_{1-4}$-alkyloxy, trifluoromethoxy, phenoxy, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, or phenyl.

($e^4$): Most preferably, $R^7$ denotes fluorine, chlorine, bromine, methyl, isopropyl, trifluoromethyl, hydroxy, methoxy, trifluoromethoxy, phenoxy, aminomethyl, carboxy, methoxycarbonyl, aminocarbonyl, or phenyl.

f) Definitions (f) for $R^{11}$ in the order of preference, ascending from preferably ($f^1$) to more preferably ($f^2$) up to most preferably ($f^3$):

($f^1$) Preferably, $R^{11}$ denotes fluorine, chlorine, bromine, $C_{1-3}$-alkyl, difluoromethyl, trifluoromethyl, cyano, nitro, amino, acetylamino, methylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, methylsulfanyl, methylsulfinyl, methylsulfonyl, hydroxy, $C_{1-3}$-alkyloxy, difluoromethoxy, or trifluoromethoxy.

($f^2$) More preferably, $R^{11}$ denotes fluorine, chlorine, methyl, difluoromethyl, trifluoromethyl, cyano, acetylamino, methylsulfonylamino, carboxy, $C_{1-3}$-alkyloxycarbonyl, aminocarbonyl, methylaminocarbonyl, dimethyl-aminocarbonyl, hydroxy, or methoxy.

($f^3$) Most preferably, $R^{11}$ denotes fluorine, methyl, methoxy, cyano, or acetylamino.

Each $a^i, b^i, c^i, d^i, e^i, f^i$ represents a characterized, individual embodiment for the corresponding substituent as described above. So given the above definitions, preferred individual embodiments of the first aspect of the invention are fully characterized by the term ($a^i b^i c^i d^i e^i f^i$) if for each letter i in this term an individual figure is given. Indices i vary independently from each other. All individual embodiments described by the term in brackets with full permutation of indices i, referring to the above definitions, shall be comprised by the present invention.

The following table 1 shows, exemplarily and in the order of increasing preference from the first line to the last line, such embodiments E-1 to E-18 of the invention that are considered preferred. This means that embodiment E-18, represented by the entries in the last row of table 1, is the most preferred embodiment.

TABLE 2

Preferred embodiments E-1 to E-18 of the invention

|      | $R^1$ | $R^2$ | $R^4$ | $R^5/R^6$ | $R^7$ | $R^{11}$ |
|------|-------|-------|-------|-----------|-------|----------|
| E-1  | $a^1$ | $b^1$ | $c^1$ | $d^1$ | $e^1$ | $f^1$ |
| E-2  | $a^2$ | $b^2$ | $c^1$ | $d^2$ | $e^1$ | $f^2$ |
| E-3  | $a^2$ | $b^2$ | $c^2$ | $d^2$ | $e^1$ | $f^3$ |
| E-4  | $a^2$ | $b^2$ | $c^1$ | $d^2$ | $e^2$ | $f^3$ |
| E-5  | $a^2$ | $b^2$ | $c^2$ | $d^2$ | $e^2$ | $f^3$ |
| E-6  | $a^2$ | $b^3$ | $c^2$ | $d^3$ | $e^2$ | $f^3$ |
| E-7  | $a^3$ | $b^3$ | $c^2$ | $d^3$ | $e^2$ | $f^3$ |
| E-8  | $a^3$ | $b^3$ | $c^3$ | $d^3$ | $e^2$ | $f^3$ |
| E-9  | $a^3$ | $b^3$ | $c^2$ | $d^3$ | $e^3$ | $f^3$ |
| E-10 | $a^4$ | $b^3$ | $c^2$ | $d^3$ | $e^2$ | $f^3$ |
| E-11 | $a^4$ | $b^4$ | $c^2$ | $d^3$ | $e^2$ | $f^3$ |
| E-12 | $a^4$ | $b^4$ | $c^3$ | $d^3$ | $e^2$ | $f^3$ |
| E-13 | $a^4$ | $b^4$ | $c^2$ | $d^3$ | $e^3$ | $f^3$ |
| E-14 | $a^3$ | $b^3$ | $c^3$ | $d^3$ | $e^3$ | $f^3$ |
| E-15 | $a^3$ | $b^3$ | $c^3$ | $d^3$ | $e^4$ | $f^3$ |
| E-16 | $a^3$ | $b^3$ | $c^4$ | $d^3$ | $e^3$ | $f^3$ |
| E-17 | $a^3$ | $b^3$ | $c^4$ | $d^3$ | $e^4$ | $f^3$ |
| E-18 | $a^4$ | $b^4$ | $c^4$ | $d^3$ | $e^4$ | $f^3$ | including the tautomers, the stereoisomers, the mixtures, and the salts thereof.

Another preferred embodiment of this invention is described by the formula Ia

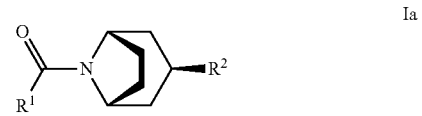

wherein the residue $R^2$ occupies the endo (=trans to the NCOR$^1$ residue and cis to the ethylene bridge) position of the bicyclic structure and wherein $R^1$ and $R^2$ are defined as hereinbefore and hereinafter, the tautomers, the stereoisomers, the mixtures, and the salts thereof.

Some terms used above and hereinafter to describe the compounds according to the invention will now be defined more closely.

The term "substituted" as used herein, means that any one or more hydrogens on the designated atom is replaced with a selection from the indicated group, provided that the designated atom's normal valence is not exceeded, and that the substitution results in a stable compound.

The term "optionally substituted with one or more, preferably one to four, substituents" means that the respective group is unsubstituted or substituted with one, two, three or four substituents.

The term "partially unsaturated" as used herein, means that in the designated group or moiety 1, 2 or more, preferably 1 or 2, double bonds are present. Preferably as used herein, the term "partially unsaturated" does not cover fully unsaturated groups or moieties.

The term halogen denotes an atom selected from the group consisting of F, Cl, Br, and I.

The term $C_{1-n}$-alkyl, wherein n may have a value of 2 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term $C_{3-n}$-cycloalkyl denotes a saturated mono-, bi-, tri- or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc. Preferably the term $C_{3-7}$-cycloalkyl denotes saturated monocyclic groups.

The term $C_{3-n}$-cycloheteroalkyl denotes a saturated mono-, bi-, tri- or spirocarbocyclic group with 3-m to n-m C atoms and wherein n denotes 3 to 10 and m denotes 1 to 3 heteroatoms independently selected from $NR^N$, O, S, SO, and $SO_2$, which in addition may have a carbonyl group. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperid inonyl, piperazinonyl, morpholinonyl. Preferably the term $C_{3-6}$-cycloheteroalkyl denotes saturated monocyclic groups with one or two heteroatoms.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term heteroaromatic denotes an aromatic structure which has at least one carbon atom replaced with a heteroatom such as N, O, or S. Examples of such groups include pyrrolyl, furanyl, thienyl, imidazolyl, pyrazolyl, oxazolyl, thiazolyl, triazolyl, oxadiazolyl, tetrazolyl, pyridinyl, pyrimidinyl, pyridazinyl, pyrazinyl, triazinyl, indolyl, benzimidazolyl, quinolinyl, isoquinolinyl, quinazolinyl, etc.

The term tri-($C_{1-4}$-alkyl)silyl comprises silyl groups which have identical or two or three different alkyl groups.

The term di-($C_{1-3}$-alkyl)amino comprises amino groups which have identical or two different alkyl groups.

If groups or residues are optionally substituted, this applies to any form of the group or residue. For instance, if an alkyl group is optionally mono- or polyfluorinated this comprises also alkyl residues which are part of larger groups, e.g. alkyloxy, alkylcarbonyl, alkoxyalkyl, etc. Accordingly, in cases where $R^4$ or $R^7$ has e.g. the meaning alkyloxy, while alkyl residues are optionally mono- or polyfluorinated, the meanings difluoromethoxy and trifluoromethoxy are also comprised. The same applies to groups or residues in which a $CH_2$ group may be replaced by O, S, NR, CO, or $SO_2$. For instance, a residue having inter alia the meaning hydroxy-$C_{1-3}$-alkyl, in which a $CH_2$ group may be replaced by CO, this comprises carboxy, carboxymethyl, hydroxymethylcarbonyl, carboxyethyl, hydroxymethylcarbonylmethyl, and hydroxyethylcarbonyl.

All atoms/elements, including atoms that are part of a group, described herein comprise all stable isotopic forms of the respective element. For instance, whenever hydrogen is mentioned, either explicitly or as part of a group such as methyl, this includes hydrogen and deuterium as stable isotopic forms of the element hydrogen.

The compounds according to the invention may be obtained using methods of synthesis known in principle. Preferably the compounds are obtained by the following methods according to the invention which are described in more detail hereinafter.

Scheme 1 summarizes different approaches to prepare the nortropane skeleton from butan-1,4-dione or a cyclic congener thereof and 1,3-acetonedicarboxylic acid, acetoacetic acid ester, or derivatives thereof. Reactions 1.) and 3.) represent an example of combining succinaldehyde, 1,3-acetonedicarboxylic acid diester or acetoacetic acid ester and an amine, e.g. a protected ammonia equivalent such as benzylamine or methylamine, to obtain 3-oxo-8-aza-bicyclo[3.2.1] octane-2,4-dicarboxylic acid diesters as intermediates. Reaction 1.) is preferably carried out in an alcohol, such as methanol, ethanol or benzyl alcohol, or an aqueous solvent. Preferred co-solvents are N,N-dimethylformamide, N,N-dimethylacetamide, N-methylpyrrolidinone, dimethylsulfoxide, tetrahydrofuran, 1,4-dioxane, or 1,2-dimethoxyethane (see e.g. *J. Chem. Soc.* 1917, 111, 766; *Tetrahedron Asymmetry* 2002, 21, 2351-2358; U.S. Pat. No. 2,845,427, 1955 and U.S. Pat. No. 2,836,598, 1954; patent, DE 352981 and DE 354950; and references quoted therein). The reactions may also be carried out without an additional solvent or in one of the co-solvents mentioned. The transformation may be conducted without an additive but often the presence of a base, such as sodium hydroxide, methoxide, or tert-butoxide, or an acid, such as hydrochloric acid, is advantageous or even essential. Using a base or an acid as additive may result in the direct formation of the N-substituted nortropanone depending on the alkyl ester used. The reactions are carried out at −30 to 160° C., preferably between −10 and 120° C. The carboxy groups may be removed after basic or acidic hydrolysis of the ester groups at temperatures between 10 and 140° C. Since the same solvents may be applied as for the preceding step, the reaction may be carried out in the same reaction pot. Reaction 3.) may be conducted as described for 1.), preferably in the presence of an alkali metal hydroxide in an aqueous or alcoholic solution (see e.g. patent DE 345759). Equation 2.) shows an example using a dialkoxytetrahydrofuran as a succinaldehyde surrogate to prepare the nortropanone framework (see e.g. *J. Am. Chem. Soc.* 1952, 74, 3825-3828; *Helv. Chim. Acta* 1986, 69, 887-897; *J. Heterocycl. Chem.* 1992, 29, 1541-1544; *Helv. Chim. Acta* 2003, 86, 812-826;

and citations quoted therein). These reactions are preferably carried out with 1,3-acetonedicarboxylic acid and an amine, such as e.g. benzylamine, methylamine, or 4-methoxyaniline, in water that may be combined with alcohols, e.g. methanol or ethanol, N,N-dimethylformamide, N,N-dimethylacetamide, N-methylpyrrolidinone, dimethylsulfoxide, tetrahydrofuran, 1,4-dioxane, or 1,2-dimethoxyethane. The overall transformation consists of three reaction steps: liberation of succinaldehyde from the precursor, reaction of succinaldehyde with the amine followed by the reaction with 1,3-acetonedicarboxylic acid (Mannich reaction) and eventually decarboxylation of the carboxyl groups. Accordingly, the reaction conditions, primarily the pH value of the solution, have to be adjusted over the course of the sequence. Liberation of succinaldehyde from the precursor is preferably done by the treatment with acid, e.g. hydrochloric acid, sulfuric acid, or phosphoric acid, at temperatures of −10 to 60° C. Then, the amine and 1,3-acetonedicarboxylic acid are added and the pH value of the solution is raised by the addition of additives, e.g. alkali metal acetate, citrate, phosphate, or hydrogenphosphate; this step is preferably conducted between −10 and 60° C. The eventual decarboxylation is achieved by increasing the temperature, preferably to 30 to 140° C.; lowering the pH value, using e.g. hydrochloric acid, may be advantageous. Nortropanone may also be prepared from N-protected 2,5-dialkoxypyrrolidine and a diene or an silyl enol ether as exemplified in equations 4.) and 5.) (see e.g. *Chem. Commun.* 2002, 2626-2627; *Synlett* 2004, 143-145; and references quoted therein). These reactions are carried out under anhydrous conditions in an inert solvent such as dichloromethane, 1,2-dichloroethane, fluorinated hydrocarbons, ether, 1,4-dioxane, benzene, toluene, or hexane. The presence of a Lewis acid, such as trimethylsilyl triflate (=trifluoromethanesulfonate), boron trifluoride etherate, or a lanthanide triflate, is essential to promote the reactions. Preferably, the reactions are performed at temperatures between −78 and 100° C.

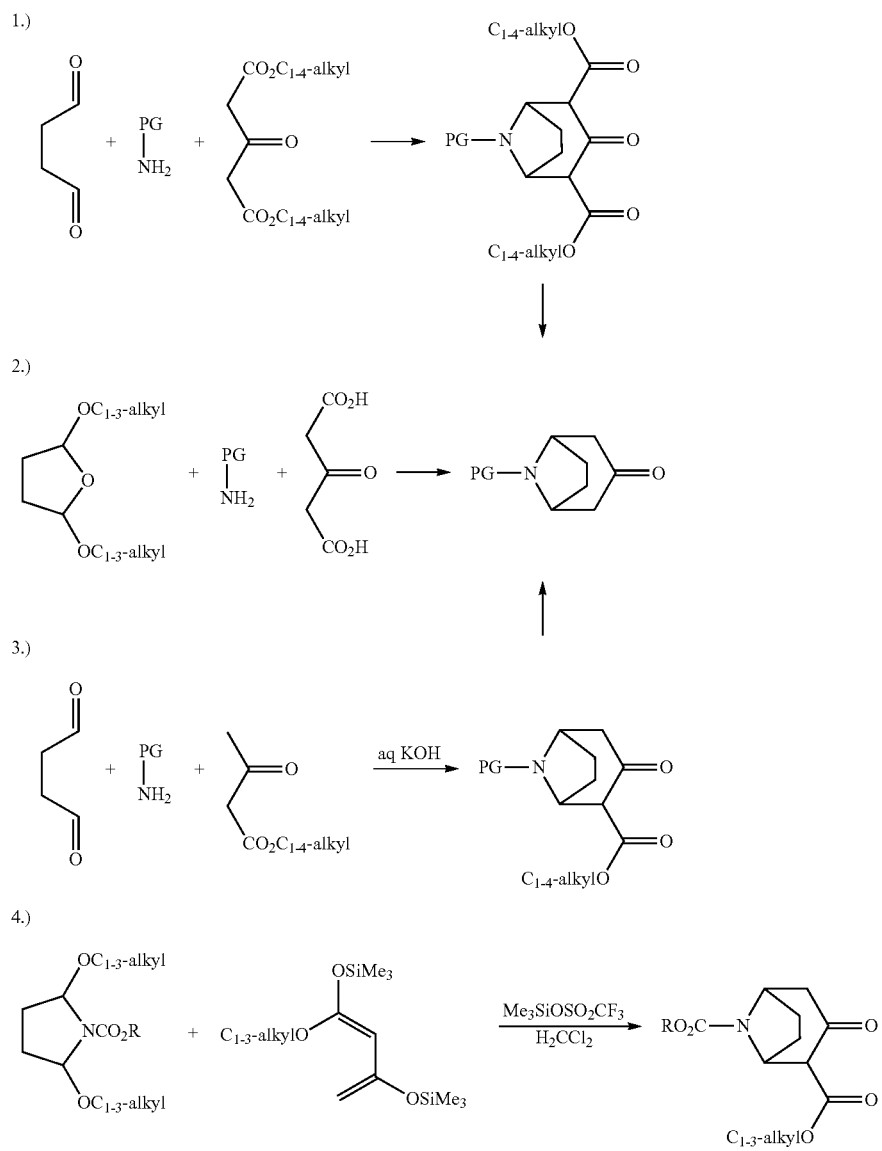

Scheme 1. Synthetic routes to Nortropanones

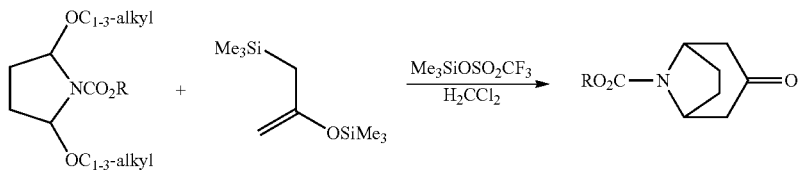

R = e.g. $C_{1-4}$-alkyl, $Me_3SiCH_2CH_2$, $Cl_3CCH_2$, benzyl, allyl
PG = protective group Another viable synthetic route to the nortropanone scaffold is delineated in Scheme 2. Key reaction is the addition of an amine, e.g. benzylamine, methyl amine, 4-methoxyaniline, or hydroxylamine, to cycloheptadienone (see e.g. *J. Am. Chem. Soc.* 1989, 111, 4433-4440; *J. Am. Chem. Soc.* 2002, 124, 2245-2258; and references cited therein). This reaction is preferably carried out in an alcohol, e.g. methanol or ethanol, that may be combined with solvents such as water, N,N-dimethylformamide, N,N-dimethylacetamide, N-methylpyrrolidinone, dimethylsulfoxide, tetrahydrofuran, 1,4-dioxane, ether, or 1,2-dimethoxyethane, at temperatures ranging from 0 to 120° C. Beneficial additives may be bases such as e.g. potassium carbonate, calcium oxide, triethylamine, ethyldiisopropylamine, diazabicycloundecene, or alkali metal alkoxides. Cyclohepta-2,6-dienone may be obtained from cycloheptanone as described (see e.g. *J. Am. Chem. Soc.* 2002, 124, 2245-2258 and references cited therein).

Scheme 2. Synthesis of Nortropanones from Cycloheptadienone

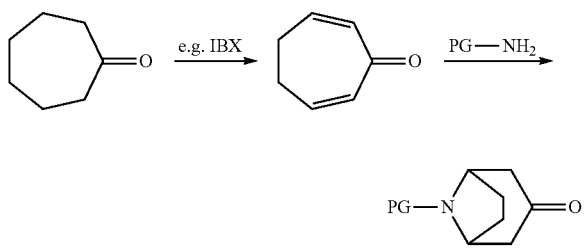

IBX = 2-iodoxybenzoic acid
PG = protective group

Residue $R^2$ or a precursor of it may be introduced as described in Scheme 3; $R^2$ has the meanings as defined hereinbefore and hereinafter. Addition of a magnesium halide or lithium derivative of $R^2$ to an N-protected nortropanone delivers the corresponding nortropanol. This transformation is preferably conducted in ether, 1,4-dioxane, 1,2-dimethoxyethane, benzene, toluene, tetrahydrofuran, hexane, N-methylpyrrolidinone, dimethylsufoxide, or mixtures thereof at temperatures between −80 and 60° C., preferably between −50 and 40° C. The subsequent dehydration reaction to acquire the nortropene derivative may be performed using an acid, e.g. hydrochloric acid, hydrobromic acid, sulfuric acid, or phosphoric acid, a dehydrating reagent such as Burgess' reagent or Martin's sulfurane, or a sulfonyl chloride or anhydride in combination with a base such as methylsulfonyl chloride and triethylamine, thionyl chloride and pyridine, or trifluoromethanesulfonic anhydride and pyridine. The reaction using an acid are preferably conducted in aqueous or alcoholic solutions that may contain co-solvents, e.g. tetrahydrofuran, N,N-dimethylformamide, dimethylsulfoxide, 1,4-dioxane, 1,2-dimethoxyethane, acetonitrile, or N-methylpyrrolidinone, at temperatures between 10 and 140° C. The conversion employing an dehydrating reagent is preferably conducted in an inert solvent such as dichloromethane, 1,2-dichloroethane, benzene, toluene, hexane, tetrahydrofuran, 1,4-dioxane, or 1,2-dimethoxyethane, at −30 to 140° C., preferably at −10 to 120° C. The double bond is subsequently hydrogenated to give the derivatized nortropane. Competent catalysts for the hydrogenation using hydrogen may be e.g. platinum oxide, palladium on carbon, palladium hydroxide, Raney nickel, rhodium, ruthenium, and $ClRh(PPh_3)_3$. The hydrogenation is carried out at temperatures between 0 and 180° C., preferably between 10 and 120° C., and at hydrogen pressures between 1 and 10 bar, preferably between 1 and 6 bar. Suited solvents may be ethyl acetate, alcohols, e.g. methanol or ethanol, tetrahydrofuran, 1,4-dioxane, 1,2-dimethoxyethane, N-methylpyrrolidinone, N,N-dimethylacetamide, N,N-dimethylformamide, dichloromethane, hexanes, toluene, benzene, dimethlylsulfoxide, acetonitrile, acetic acid, or mixtures thereof. Beneficial additives may be acids such as hydrochloric acid, sulfuric acid, methanesulfonic acid, trifluoroacetic acid, or acetic acid. The one-step conversion of the nortropanol derivative to the nortropane may also be feasible. This transformation may be carried out using hydrogen in the presence of a transition metal as described above, preferably in the presence of an acid. Alternatively, the reduction may be performed with a hydride source such as a silane, e.g. triethylsilane, borohydride, e.g. sodium borohydride, triacetoxyborohydride, or cyanoborohydride, aluminum hydride, e.g. lithium aluminumhydride, in the presence of a Lewis acid such as boron trifluoride, trimethylsilyl triflate, aluminum chloride, alkylaluminum dichloride, dialkylaluminum chloride, lanthanide triflates, scandium triflate, trifluoroacetic acid, or triflic acid. Preferred solvents for the latter process may be dichloromethane, 1,2-dichloroethane, 1,4-dioxane, 1,2-dimethoxyethane, hexanes, toluene, benzene, chlorobenzene, and acetonitrile that are preferably used at temperatures between −30 and 180° C., more preferably between 0 and 140° C. The latter conditions are suited for electron-rich aromatic $R^2$ residues.

The reduction from nortropanol or nortropene to nortropane may give mixtures of isomers (endo and exo) depending on the protective group used on the nitrogen and the reaction conditions. Mixtures of isomers can be separated into the pure isomers by chromatography, distillation, or crystallization as described above. The entire sequence sketched in Scheme 3 is concluded by the removal of the protective group that may be accomplished as described hereinbefore.

Scheme 3. Elaboration of Nortropanones I

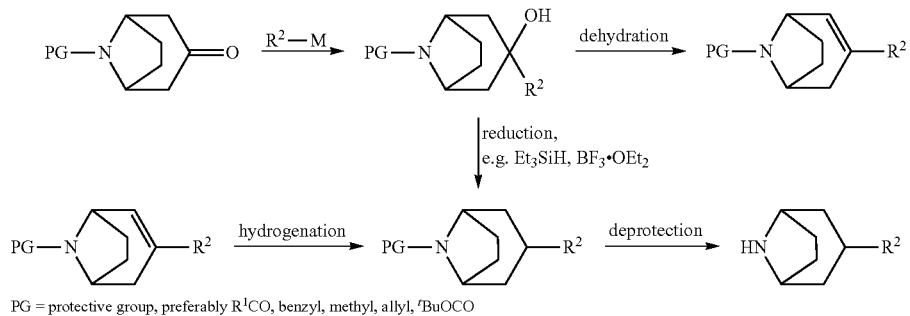

PG = protective group, preferably R$^1$CO, benzyl, methyl, allyl, $^t$BuOCO

Scheme 4 depicts another synthetic route to the respectively derivatized nortropanes; R$^2$ has the meanings as defined hereinbefore and hereinafter. Starting with the N-protected nortropanone the corresponding enol trifluoromethanesulfonates (=triflate) may be accessed by treatment of the ketone with a base such as e.g. alkali metal hexamethyldisilylamide, alkali metal diisopropylamide, lithium 2,2,6,6-tetramethylpiperidide, tert-butyllithium, trityllithium, ethyldiisopropylamine, triethylamine, or 1,8-diazabicyclo[5.4.0]undec-7-ene (DBU) and trapping the enolate with an trifluoromethylsulfonyl electrophile equivalent such as triflic anhydride (F$_3$CSO$_2$OSO$_2$CF$_3$), F$_3$CSO$_2$Cl, PhNTf$_2$, or ArNTf$_2$ (Ar=e.g. pyridyl or chloropyridyl; Tf=F$_3$CSO$_2$). The reaction may be conducted in solvents such as e.g. tetrahydrofuran, 1,4-dioxane, 1,2-dimethoxyethane, ether, dichloromethane, benzene, toluene, hexanes, or mixtures thereof at temperatures between −80 and 80° C., preferably between −70 and 40° C. Additives such as pyridine, 4-dimethylaminopyridine, lithium chloride, 1,3-dimethyl-3,4,5,6-tetrahydro-2(1H)-pyrimidinone, or hexamethylphosphoramide may be beneficial. Attachment of the residue R$^2$ may be accomplished by treatment of the enol triflate with an appropriately derivatized R$^2$ in the presence of a transition metal catalyst. Appropriate R$^2$ are derived from e.g. lithium (R$^2$Li), magnesium, e.g. R$^2$MgCl or Br, zinc, e.g. R$^2$ZnCl/I/Br, boronic acid [R$^2$B(OH)$_2$], boronic esters, e.g. R$^2$B(OMe)$_2$ or R$^2$B(OCMe$_2$CMe$_2$O), trifluoroborates, e.g. R$^2$BF$_3$K, silanes, e.g. R$^2$SiF$_3$, or stannanes, e.g. R$^2$SnBu$_3$ or R$^2$SnMe$_3$. Suited transition metal catalysts may be derived from palladium, copper, iron, and nickel that may be used as e.g. salts, complexes, or elemental modifications. Complexes can be formed in situ or prior to the addition of the transition metal to the reaction mixture. The ligands in the complexes of the transition metal may be e.g. phosphines, e.g. triphenylphosphine, tritolylphospine, trifurylphosphine, substituted (2-phenylphen-1-yl)-dicyclohexylphosphines, substituted (2-phenylphen-1-yl)-di-(tert-butyl)-phosphines, tri-tert-butylphosphine, tri-cyclohexylphosphine, 1,1'-bis(diphenylphosphino)-ferrocene, phosphites, 1,3-disubstituted dihydroimidazolium carbenes, 1,3-disubstituted imidazolium carbenes, nitriles, e.g. acetonitrile or benzonitrile, and alkenes, e.g. benzylideneacetone or allyl. Elemental forms of the transition metals may be e.g. metal on charcoal or nanoparticles of the transition metal. Suitable salts may comprise e.g. halides, trifluoromethanesulfonates, acetates, or trifluoroacetates. The reaction is preferably carried out in an inert organic solvent or mixtures thereof. Suitable solvents may be e.g. tetrahydrofuran, 1,4-dioxane, 1,2-dimethoxyethane, hexane, toluene, benzene, N,N-dimethylformamide, N,N-dimethylacetamide, N-methylpyrrolidinone, acetone, acetonitrile, ethyl acetate, water, methanol, ethanol, propanol, isopropanol, ethylene glycol, and polyethylene glycol. The coupling reactions are preferably carried out between −80 and 180° C., more preferably at −20 to 120° C. Beneficial additives may be alkali metal salts, e.g. lithium chloride, tetraalkylammonium salts, e.g. tetrabutylammonium fluoride or hydroxide, silver salts, e.g. silver trifluoromethanesulfonate, copper salts, e.g. copper iodide or copper thiophenecarboxylate, or bases, e.g. alkali metal hydroxides, potassium carbonate, alkali metal alcoxides, or alkali metal fluorides. The presented coupling approach to introduce R$^2$ is not restricted to enol trifluoromethanesulfonates derived from nortropanones but may also be conducted using the corresponding alkenyl chlorides, bromides, or iodides. The concluding steps in Scheme 4 have been described above.

Scheme 4. Elaboration of Nortropanones II

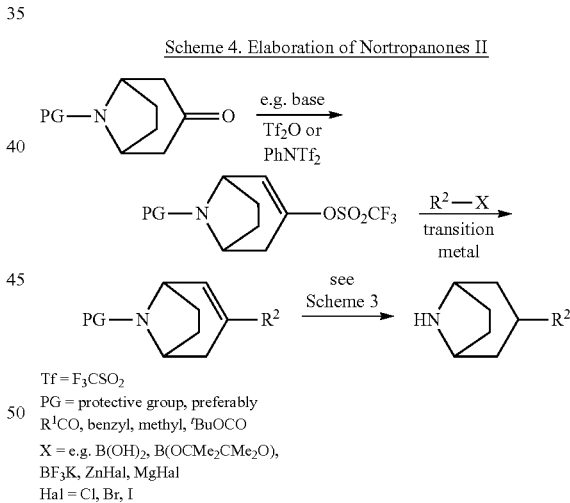

Tf = F$_3$CSO$_2$
PG = protective group, preferably R$^1$CO, benzyl, methyl, $^t$BuOCO
X = e.g. B(OH)$_2$, B(OCMe$_2$CMe$_2$O), BF$_3$K, ZnHal, MgHal
Hal = Cl, Br, I The synthetic routes presented may rely on the use of protecting groups. Suitable protecting groups for the respective functionalities and their removal have been described hereinbefore and may analogously be employed (see also: *Protecting Groups*, Philip J. Kocienski, 3$^{rd}$ edition, Georg Thieme Verlag, Stuttgart, 2004 and references quoted therein).

Compounds according to the invention obtained by the synthetic routes described may be subsequently converted into other compounds of the invention by routine processes applicable for conversion of functional groups. Examples for subsequent conversion processes are provided in the following paragraphs.

If in the process of manufacture according to the invention a compound of general formula I is obtained which contains an amino, alkylamino, or imino group, this may be converted by acylation or sulfonylation into a corresponding acyl or sulfonyl compound of general formula I;

if a compound of general formula I is obtained which contains an amino, alkylamino, or imino group, this may be converted by alkylation or reductive alkylation into a corresponding alkyl compound of general formula I;

if a compound of general formula I is obtained which contains a nitro group, this may be converted by reduction into a corresponding amino compound;

if a compound of general formula I is obtained which contains an imino group, this may be converted by nitrosation and subsequent reduction into a corresponding N-amino-imino compound;

if a compound of general formula I is obtained which contains a $C_{1-3}$-alkyloxycarbonyl group, this may be converted by cleavage of the ester into the corresponding carboxy compound;

if a compound of general formula I is obtained which contains a carboxy group, this may be converted by esterification into a corresponding ester of general formula I;

if a compound of general formula I is obtained which contains a carboxy or ester group, this may be converted by reaction with an amine into a corresponding amide of general formula I;

if a compound of general formula I is obtained which contains a cyano group, this may be converted by hydrolysis into the corresponding carboxy compound;

if a compound of general formula I is obtained which contains an aromatic substructure, this may be derivatized by an electrophilic substitution reaction with a chlorine, bromine, or iodine atom or a nitro, $SO_3H$, or acyl group to a corresponding compound of general formula I;

if a compound of general formula I is obtained which contains an aromatic amino group, this may be transformed into a corresponding cyano, fluoro, chloro, bromo, iodo, hydroxy, mercapto, or azido compound of general formula I by diazotization and subsequent replacement of the diazo group with cyanide, fluoride, chloride, bromide, iodide, hydroxide, alkyl or hydrogen sulfide, or azide, respectively;

if a compound of general formula I is obtained which contains an aromatic amino group, this may be converted into a corresponding aryl derivatized aromatic compound of general formula I by diazotization and subsequent replacement of the diazo group with an appropriate aryl nucleophile mediated by a suited transition metal species;

if a compound of general formula I is obtained which contains an aromatic chloro, bromo, iodo, trifluoromethylsulfonyloxy, mesyloxy, or tosyloxy group, this may be converted into a corresponding aryl, alkenyl, alkynyl, or alkyl derivatized compound of general formula I by replacement of the respective group by aryl, alkenyl, alkynyl, or alkyl using a transition metal species mediated process;

if a compound of general formula I is obtained which contains two heteroatoms at adjacent carbon atoms that are amino and hydroxy, amino, or mercapto, these heteroatoms may be linked via a carboxy carbon atom to form a cyclic amidine, imino ester, or imino thioester substructure that may be part of an aromatic ring;

if a compound of general formula I is obtained which contains a cyano group, this may be converted into an amino alkyl derivatized compound of general formula I by reduction;

if a compound of general formula I is obtained which contains a cyano group, this may be converted into a N-hydroxycarbamimidoyl group by the treatment with hydroxylamine;

if a compound of general formula I is obtained which contains a N-hydroxycarbamimidoyl group, this may be converted to an oxadiazole derivatized compound of general formula I by the treatment with a carboxylic or related group;

if a compound of general formula I is obtained which contains an aminocarbonyl group, this may be converted by dehydration into a corresponding cyano compound of general formula I;

if a compound of general formula I is obtained which contains a keto or aldehydic group, this may be converted by reduction into a corresponding hydroxyl compound of general formula I;

if a compound of general formula I is obtained which contains an aromatic trialkylsilyl group, this may be converted into a corresponding chloro, bromo, or iodo compound of general formula I by electrophilic displacement of the silyl group; and/or if a compound of general formula I is obtained which contains an aromatic alkyloxy group, this may be converted into a corresponding hydroxy compound of general formula I.

The subsequent esterification is optionally carried out in a solvent or mixture of solvents such as methylene chloride, N,N-dimethylformamide, benzene, toluene, chlorobenzene, tetrahydrofuran, benzene/tetrahydrofuran or 1,4-dioxane or particularly advantageously in a corresponding alcohol, optionally in the presence of an acid such as hydrochloric acid, isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclo-hexylcarbodiimide, N,N'-dicyclohexylcarbodiimide/N-hydroxysuccinimide, 1-hydroxy-benzo-triazole, 4-dimethylamino-pyridine, N,N'-carbonyldiimidazole, triphenylphosphine/carbon tetrachloride, or combinations thereof, conveniently at temperatures between 0 and 150° C., preferably at temperatures between 0 and 80° C.

The subsequent ester formation may also be carried out by reacting a compound which contains a carboxy group with a corresponding alkyl halide in the presence of a base such as cesium carbonate, potassium carbonate, triethylamine, sodium hydroxide, or sodium methoxide. Polar solvents such as N,N-dimethylformamide, N-methylpyrrolidinone, alcohol, e.g. methanol or ethanol, water, acetonitrile, or tetrahydrofuran are preferred at temperatures between 10 and 120° C.

The subsequent acylation or sulfonylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with a corresponding acyl or sulfonyl derivative, optionally in the presence of a tertiary organic base or an inorganic base, and/or in the presence of isobutyl chloroformate, thionyl chloride, trimethylchlorosilane, sulfuric acid, methanesulfonic acid, p-toluenesulfonic acid, phosphorus trichloride, $P_2O_5$, N,N'-dicyclohexylcarbodiimide, N,N'-carbonyldiimidazole, N,N'-dicyclohexyl-carbodiimide/N-hydroxysuccinimide, 1-hydroxy-benzotriazole, 4-dimethylamino-pyridine, triphenylphosphine/carbon tetrachloride, or combinations thereof. The transformation is carried out at temperatures between 0 and 150° C., preferably at temperatures between 0 and 80° C.

The subsequent alkylation is optionally carried out in a solvent or mixture of solvents such as methylene chloride, N,N-dimethylformamide, benzene, toluene, chlorobenzene, tetrahydrofuran, benzene/tetrahydrofuran, or 1,4-dioxane with an alkylating agent such as a corresponding halide or sulfonic acid ester, e.g. methyl iodide, ethyl bromide, dimethylsulfate, or benzyl chloride, optionally in the presence of a tertiary organic base or an inorganic base at temperatures between 0 and 150° C., preferably at temperatures between 0 and 100° C.

The subsequent reductive alkylation is carried out with a corresponding carbonyl compound such as e.g. formaldehyde, acetaldehyde, propionaldehyde, acetone, or butyraldehyde in the presence of a complex metal hydride such as sodium borohydride, lithium borohydride, sodium triacetoxyborohydride, or sodium cyanoborohydride conveniently at a pH value of 6-7 and at ambient temperature or in the presence of a hydrogenation catalyst, e.g. with hydrogen in the presence of palladium/charcoal, at a hydrogen pressure of 1 to 5 bar. The methylation may also be carried out in the presence of formic acid or a formate as reducing agent at elevated temperature, e.g. between 60 and 120° C.

The subsequent reduction of a nitro group is carried out, for example, with hydrogen and a metal catalyst such as palladium on carbon, platinum dioxide, or Raney nickel, or using other reducing agents such as iron or zinc in the presence of an acid such as acetic acid.

The subsequent nitrosation of an imino group followed by reduction to obtain the N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-3}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide.

The subsequent amide formation is carried out by reacting a corresponding reactive carboxylic acid derivative with a corresponding amine optionally in a solvent or mixture of solvents such as methylene chloride, N,N-dimethylformamide, benzene, toluene, chlorobenzene, tetrahydrofuran, benzene/tetrahydrofuran, or 1,4-dioxane, while the amine used may simultaneously serve as solvent, optionally in the presence of a tertiary organic base or an inorganic base or with a corresponding carboxylic acid in the presence of a dehydrating agent. Isobutyl chloroformate, thionyl chloride, trimethylchlorosilane, phosphorus trichloride, $P_2O_5$, N,N'-dicyclohexylcarbodiimide, N,N'-dicyclohexylcarbodiimide/N-hydroxysuccinimide, N,N'-carbonyldiimidazole, or triphenylphosphine/carbon tetrachloride alone or in combination with 1-hydroxy-benzotriazole and/or 4-dimethylamino-pyridine may be used at temperatures between 0 and 150° C., preferably between 0 and 80° C.

The subsequent hydrolysis of a cyano group to obtain the carboxy group is carried out by treatment with, for example, an acid such as hydrochloric acid, phosphoric acid, or sulfuric acid or an alkali metal hydroxide such as lithium hydroxide, sodium hydroxide, or potassium hydroxide in an aqueous solution at elevated temperatures, preferably between 20 and 160° C.

The subsequent introduction of a chlorine, bromine, or iodine atom onto an aromatic substructure may be carried out by reacting the aromatic compound with an appropriate electrophile of the halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr/ceric ammonium nitrate, KCl or KBr with Oxone®, or KBr/sodium perborate. Suited iodine electrophiles may be generated from iodine combined with an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles may be used without an additive or in the presence of an acid such as e.g. acetic acid, trifluoroacetic acid, or sulfuric acid, or a Lewis acid such as borontrifluoride hydrate, or copper salts. If a nitro group is to be introduced appropriate nitro electrophiles may be generated from, for example, nitric acid, acetyl nitrate, ceric ammonium nitrate, sodium nitrate, $N_2O_5$, alkyl nitrate, and nitronium tetrafluoroborate. Some of these reagents may be used without an additive though several of them are better used in combination with an acid, e.g. sulfuric acid or triflic acid, acetic anhydride, trifluoroacetic anhydride, Lewis acids, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Acylation of the aromatic part is conducted using an acyl electrophile that may be generated from the respective acyl halide, e.g. chloride, or acyl anhydride and a Lewis acid such as e.g. aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is best introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, dichloroethane, chlorobenzene, dichlorobenzene, ether, fluorinated hydrocarbons, hexanes, quinoline, or acetonitrile. The temperatures preferably applied range from 0 and 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, dichloroethane, N,N-dimethylformamide, N-methylpyrrolidinone, benzene, toluene, chlorobenzene, tetrahydrofuran, water, ethyl acetate, alcohol, ether, dimethoxyethane, dioxane, or mixtures thereof at temperatures between −10° C. and 100° C. (diazotization of amino groups is detailed in, for example, *Angew. Chem. Int. Ed.* 1976, 15, 251). The subsequent displacement of the diazo group by a cyano group, bromine, or chlorine atom using cuprous cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10° C. and 120° C. in one of the solvents or mixtures mentioned above. The replacement of the diazo group by a fluorine atom may be achieved with a tetrafluoroborate salt or tetrafluoroboric acid and heating to 20 to 160° C.; the transformation is called Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180°

C. The reaction often works without further additives but the addition of cuprous oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be carried out via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from e.g. palladium, nickel, rhodium, copper, or iron, preferably palladium. The active catalyst may be a complex of the transition metal with ligands such as e.g. phosphines, phosphites, imidazole carbenes, imidazolidine carbenes, dibenzylideneacetone, allyl, nitriles, an elemental form of the transition metal such as palladium on carbon or nanoparticles, or salts such as chloride, bromide, acetate, or trifluoroacetate. In these reactions the diazo compound is preferably employed as its tetrafluoroborate salt optionally in methylene chloride, N,N-dimethylformamide, N-methylpyrrolidinone, benzene, toluene, tetrahydrofuran, water, ethyl acetate, alcohol, ether, dimethylsulfoxide, 1,2-dimethoxyethane, 1,4-dioxane, or mixtures thereof at temperatures between 10 and 180° C., preferably between 20 and 140° C.

The subsequent replacement of an aromatic chloro, bromo, or iodo atom or an aromatic trifluoromethylsulfonyloxy, mesyloxy, or tosyloxy group by an aryl, alkenyl, alkynyl, or alkyl residue is preferably mediated by a transition metal species derived from palladium, nickel, rhodium, copper, or iron. The active catalyst may be a complex of the transition metal with ligands such as e.g. phosphines [e.g. tri-tert-butylphosphine, tricyclohexylphosphine, substituted biphenyl-dicyclohexyl-phosphines, substituted (2-phenyl-phenyl)-di-tert-butyl-phosphines, substituted (2-phenyl-phenyl)-dicyclohexyl-phosphines, triphenylphosphine, tritolylphosphine, trifurylphosphine, 1,1'-bis(diphenylphosphino)ferrocene], phosphites, imidazole carbenes, imidazolidine carbenes, dibenzylideneacetone, allyl, nitriles, an elemental form of the transition metal such as palladium on carbon or nanoparticles of iron or palladium, or salts such as fluoride, chloride, bromide, acetate, triflate, or trifluoroacetate. The replacement is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), or magnesium halide (Kumada or Kumada-type reaction) of the aryl, alkenyl, or alkyl residue to be introduced. The terminal alkyne is preferably used as it is or as zinc acetylide derivative. Depending on the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, copper salts such as copper chloride or copper thiophenecarboxylate may be advantageous or even essential. Copper iodide is a preferred additive in the coupling with a terminal alkyne group (Sonogashira reaction). The coupling reactions are optionally conducted in methylene chloride, N,N-dimethylformamide, N-methylpyrrolidinone, benzene, toluene, tetrahydrofuran, water, ethyl acetate, alcohol, ether, dimethylsulfoxide, 1,2-dimethoxyethane, 1,4-dioxane, or mixtures thereof, though, depending on the nucleophile some of them are less or not suited at all. Preferred temperatures are in the range from −10 to 180° C.

The subsequent cyclization of two heteroatoms at adjacent carbon atoms is optionally conducted with a carboxy equivalent such as a nitrile, carboxylic chloride or fluoride, carboxylic acid, ketene, carboxylic ester, or carboxylic thioester. The overall transformation consists of two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tert-butoxide. The use of dehydrating reagents such as anhydrides, e.g. acetic anhydride, orthoesters, e.g. trimethyl orthoformate, thionyl chloride, phosgene, diphosgene, triphosgene, phosphorus oxychloride, phosphorus pentachloride, dialkylcarbodiimides, combinations of phosphines, e.g. triphenylphosphine or trialkylphosphine, with dialkyl azodicarboxylates, bromine, iodine, or 1,2-dihaloethanes, e.g. 1,2-dibromotetrafluoroethane, is also possible. The reactions are preferably carried out in inert solvents such as methylene chloride, dichloroethane, benzene, toluene, tetrahydrofuran, ether, or combinations thereof, though, cyclization in the presence of an acid or a base may also be conducted in water or alcohol, e.g. methanol, ethanol, iso-propanol, or tert-butanol, or combinations with these solvents. The reactions are carried out at temperatures between 0 and 200° C., preferably between 20 and 140° C.

The subsequent reduction of a cyano group to obtain an aminomethyl group is optionally conducted with hydrogen in the presence of a transition metal species or with a hydride. Suited transition metals may be derived from palladium, nickel, platinum, rhodium, or ruthenium such as, for example, palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar, preferably between 1 and 5 bar, and at temperatures between 0 and 180° C., preferably between 20 and 120° C. Additives such as acids, e.g. hydrochloric acid, methanesulfonic acid, sulfuric acid, or acetic acid, may be beneficial for the hydrogenation. Appropriate hydride sources may be selected from e.g. borohydrides, e.g. sodium borohydride, potassium tri-sec-butylborohydride, borane, or lithium triethylborohydride, or alanates, e.g. lithium aluminum hydride, or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic solutions. Preferred reaction temperatures range from −80 to 160° C., more preferably, from −40 to 60° C.

The subsequent formation of an N-hydroxycarbamimidoyl group from a cyano group may be carried out by the treatment of the cyano compound with hydroxylamine. The reaction is preferably conducted in aqueous or alcoholic solvents at temperatures between 0° C. and 140° C.

The subsequent formation of an oxadiazole from an N-hydroxycarbamimidoyl is optionally conducted with a carboxy equivalent such as nitrile, carboxylic chloride or fluoride, carboxylic acid, ketene, carboxylic ester, or carboxylic thioester. The transformation is related to the formation of a ring starting from two adjacent heteroatoms described above and may be carried out analogously.

The subsequent formation of a cyano group from an amino carbonyl group is optionally conducted by using a dehydrating reagent such as e.g. anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenyl phosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0 and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydide, or lithium aluminum hydride. The reductions may be conducted in e.g. dichloromethane, 1,2-dichloroethane, hexanes, ether, dioxane, tetrahydrofuran, N,N-dimethylformamide, N-methylpyrrolidinone, benzene, toluene, alcohols, e.g. methanol, water, or mixtures thereof, though, not all reducing agents are compatible with all of these solvents. Preferred temperatures are between −80 and 140° C. depending on the reducing power of the reagent. Alternatively, hydrogen in the presence of a transition metal catalyst may be used for the reduction.

The subsequent introduction of a chlorine, bromine, or iodine atom by displacement of an aromatic silyl group may be carried out by reacting the aromatic compound with an appropriate electrophile of the halogen atom. For example, N-chloro-, N-bromo-, or N-iodo-succinimide, iodine chloride, or bromine are suitable electrophiles for introducing the respective halogen atoms. Dichloromethane, 1,2-dichloroethane, acetonitrile, and acetic acid are among the usable solvents that are employed at temperatures between 0 and 100° C.

The subsequent cleavage of an alkoxyaryl ether is carried out, for example, by treatment with boron tribromide in an inert solvent such as dichloromethane or 1,2-dichloroethane at 0 to 80° C. Hydrobromic acid in acetic acid between 0 and 120° C. is another suitable method to cleave aromatic ethers.

In the reactions described hereinbefore, any reactive group present such as hydroxy, carboxy, amino, alkylamino, or imino may be protected during the reaction by conventional protecting groups which are cleaved again after the reaction.

For example, a protecting group for a hydroxy group may be a trimethylsilyl, tert-butyldimethylsilyl, triisopropylsilyl, acetyl, pivaloyl, benzoyl, methyl, ethyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be a trimethylsilyl, methyl, ethyl, tert-butyl, allyl, benzyl, or tetrahydropyranyl group, protecting groups for an amino, alkylamino, or imino group may be a methyl, formyl, acetyl, trifluoroacetyl, ethoxycarbonyl, tert-butoxycarbonyl, benzyloxycarbonyl, benzyl, methoxy-benzyl, or 2,4-dimethoxybenzyl group and additionally, for the amino group, a phthalyl or tetrachlorophthalyl group, and protecting groups for a terminal alkyne may be trimethylsilyl, triisopropylsilyl, tertbutyldimethylsilyl, or 2-hydroxy-isopropyl.

Any acyl protecting group may be cleaved, for example, hydrolytically in an aqueous solvent, e.g. in water, isopropanol/water, acetic acid/water, tetrahydrofuran/water, or dioxane/water, in the presence of an acid such as trifluoroacetic acid, hydrochloric acid, or sulfuric acid or in the presence of an alkali metal base such as lithium hydroxide, sodium hydroxide, or potassium hydroxide or aprotically, e.g. in the presence of iodotrimethylsilane, at temperatures between 0 and 120° C., preferably between 10 and 100° C. A trifluoroacetyl group is preferably cleaved by treating with an acid such as hydrochloric acid, optionally in a solvent such as acetic acid, at temperatures between 50 and 120° C. or by treating with sodium hydroxide solution, optionally in an additional solvent such as tetrahydrofuran or methanol, at temperatures between 0 and 80° C.

Any acetal or ketal protecting group used may be cleaved, for example, hydrolytically in an aqueous solvent, e.g. in water, isopropanol/water, acetic acid/water, tetrahydrofuran/water, or dioxane/water, in the presence of an acid such as trifluoroacetic acid, hydrochloric acid, or sulfuric acid or aprotically, e.g. in the presence of iodotrimethylsilane, at temperatures between 0 and 120° C., preferably between 10 and 100° C.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° C. Silyl groups other than trimethylsilyl are preferentially cleaved in the presence of an acid, e.g. trifluoroacetic acid, hydrochloric acid, or sulfuric acid, at temperatures between 0 and 100° C. A particularly suited cleaving method for silyl groups is based on the use of fluoride salts, e.g. tetrabutylammonium fluoride, hydrogen fluoride, or potassium fluoride, in organic solvents, such as for example diethylether, tetrahydrofuran, 1,4-dioxane, 1,2-dimethoxyethane, toluene, benzene, 1,2-dichloroethane, or dichloromethane, at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon, palladium hydroxide, or platinum oxide in a solvent such as methanol, ethanol, ethyl acetate, or glacial acetic acid, optionally in the presence of an acid, such as hydrochloric acid, at temperatures between 0 and 100° C., preferably between 20 and 60° C., and at hydrogen pressures of 1 to 7 bar, preferably 3 to 5 bar. Trimethylsilyl iodide, boron trichloride, or boron trifluoride in the presence of a scavenger such as anisol, thioanisol, or pentamethylbenzene may be used with benzylether derivatives. An electron-rich benzyl residue, such as methoxybenzyl, may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tert-butyl or tert-butyloxycarbonyl group is preferably cleaved by treating with an acid such as trifluoroacetic acid, sulfuric acid, or hydrochloric acid or by treating with iodotrimethylsilane, optionally using a solvent such as methylene chloride, 1,4-dioxane, methanol, isopropanol, water, or diethylether.

A methyl group at a tertiary amine may be cleaved by the treatment with 1-chloroethyl chloroformate. Hydrobromic acid and boron tribromide are particularly suited for the cleavage of methylethers.

The compounds of general formula I may be resolved into their enantiomers and/or diastereomers, as mentioned before. Thus, for example, cis/trans mixtures may be resolved into their cis and trans isomers, and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes. Diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallisation from an optically active solvent or by reacting with an optically active substance which forms salts or derivatives, such as e.g. esters or amides, with the racemic compound. Salts may be formed with enantiopure acids for basic compounds and with enantiopure bases for acidic compounds. Diastereomeric derivatives are formed with enantiopure auxiliary compounds such as e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, di-o-tolyltartaric acid, malic acid, mandelic acid, camphorsulfonic acid, glutamic acid, aspartic acid, or quinic acid. Optically active alcohols applicable as auxiliary may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the physiologically acceptable salts with inorganic or organic acids provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue like, for example, a carboxy group, they may be converted into the salts thereof with inorganic or organic bases, particularly for pharmaceutical use into the physiologically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine and triethanolamine, N-methyl-D-glucamine, L-lysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly an inhibitory effect on the enzyme 11β-hydroxysteroid dehydrogenase (HSD) 1.

The biological properties of the new compounds may be investigated as follows:

In vitro inhibition of 11β-HSD 1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 µM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol is determined by reading the time-resolved fluorescence of the wells (Ex 320/75 nm; Em 615/8.5 nm and 665/7.5 nm). The ratio of the two emission signals is then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal. In Table 2 the 11β-HSD 1 inhibitory activities at 1 µM concentration of test compound, determined as described above, of the compounds listed in Table 3 are compiled, wherein 100% indicates no inhibition and a value of zero or below zero indicates complete inhibition.

TABLE 2

Inhibitory activity on 11β-HSD 1 of the examples (=Ex.) listed in Table 3 determined as described above

| Ex. | % CTL |
|---|---|
| 1 | −18 |
| 2 | −27 |
| 3 | −32 |
| 4 | 87 |
| 6 | 88 |
| 7 | 68 |
| 8 | 87 |
| 9 | 87 |
| 11 | 82 |
| 12 | 85 |
| 13 | 62 |
| 15 | 56 |
| 17 | 93 |
| 18 | 97 |
| 20 | 87 |
| 23 | 83 |
| 29 | 97 |
| 30 | 88 |
| 31 | 86 |
| 32 | 94 |
| 33 | 88 |
| 34 | 75 |
| 35 | 62 |
| 36 | −28 |
| 37 | 39 |
| 38 | 12 |
| 39 | 43 |
| 40 | 98 |
| 42 | 93 |
| 43 | 95 |
| 44 | 57 |
| 45 | 82 |
| 46 | 97 |
| 47 | −17 |

TABLE 2-continued

Inhibitory activity on 11β-HSD 1 of the examples (=Ex.) listed in Table 3 determined as described above

| Ex. | % CTL |
|---|---|
| 48 | 1 |
| 49 | 67 |
| 50 | 6 |
| 51 | 41 |
| 52 | 82 |
| 53 | −55 |
| 54 | −56 |
| 55 | 31 |
| 57 | 63 |
| 58 | 68 |
| 59 | 95 |
| 60 | 63 |
| 61 | 94 |
| 62 | −47 |
| 63 | 91 |
| 64 | 99 |
| 65 | 33 |
| 66 | 77 |
| 67 | 85 |
| 68 | 66 |
| 69 | 93 |
| 70 | 19 |
| 71 | 41 |
| 73 | 90 |
| 74 | 69 |
| 75 | 92 |
| 76 | 76 |
| 77 | 47 |
| 78 | 49 |
| 79 | 90 |
| 81 | −9 |
| 82 | 5 |
| 83 | −30 |
| 84 | 41 |
| 87 | −2 |
| 88 | 98 |
| 90 | 42 |
| 91 | 69 |
| 93 | 38 |
| 94 | 12 |
| 95 | 92 |
| 96 | 33 |
| 98 | 74 |
| 99 | −39 |
| 100 | 61 |
| 101 | 4 |
| 102 | 47 |
| 103 | 32 |
| 104 | 43 |
| 105 | 58 |
| 106 | 75 |
| 107 | −38 |
| 108 | 1 |
| 109 | −33 |
| 110 | 87 |
| 111 | 61 |
| 112 | 40 |
| 113 | −23 |
| 114 | −10 |
| 115 | 33 |
| 117 | 53 |
| 118 | −28 |
| 119 | 95 |
| 120 | 25 |
| 121 | −28 |
| 122 | 63 |
| 123 | −17 |
| 124 | 59 |
| 125 | 7 |
| 126 | 63 |
| 127 | 85 |
| 128 | 79 |
| 129 | −1 |
| 130 | −47 |
| 131 | −20 |
| 132 | −36 |
| 133 | −28 |
| 134 | −5 |
| 135 | −35 |
| 136 | 17 |
| 137 | 16 |
| 138 | 4 |
| 139 | 21 |
| 140 | −5 |
| 141 | 29 |
| 142 | 31 |
| 143 | 58 |
| 144 | −59 |
| 145 | −37 |
| 146 | 96 |
| 147 | 99 |
| 148 | −48 |
| 149 | 30 |
| 150 | 62 |
| 151 | −44 |
| 152 | 5 |
| 153 | −4 |
| 154 | 59 |
| 155 | −17 |
| 156 | −13 |
| 157 | 38 |
| 158 | 86 |
| 159 | −55 |
| 160 | −26 |
| 161 | −30 |
| 162 | 96 |
| 163 | −7 |
| 164 | −29 |
| 165 | 2 |
| 166 | −33 |
| 167 | −22 |
| 168 | 6 |
| 169 | −25 |
| 170 | −34 |
| 171 | −26 |
| 172 | 0 |
| 173 | −46 |
| 174 | −40 |
| 175 | −37 |
| 176 | −42 |
| 177 | −44 |
| 178 | −22 |
| 179 | −11 |
| 180 | −41 |
| 181 | 18 |
| x | x |

In view of their ability to inhibit enzyme 11β-hydroxysteroid dehydrogenase (HSD) 1, the compounds of general formula I according to the invention and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia. These substances may also be suitable for preventing beta-cell degeneration such as e.g. apoptosis or necrosis of pancreatic beta cells. The substances are potentially also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor, and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety or depression.

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an 11β-hydroxysteroid dehydrogenase (HSD) 1 antagonist according to the invention with respect to one of the indications mentioned and/or which allow the dosage of an 11β-hydroxysteroid dehydrogenase (HSD) 1 antagonist according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, sergliflozin, canagliflozin, remogliflozin etabonate), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to ¹/₁ of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

LC-MS Method 1:

| Column | Merck Cromolith Speed ROD, RP18e, 50 × 4.6 mm |
| --- | --- |
| Mobile Phase | A: water + 0.1% HCO$_2$H |
| | B: acetonitrile + 0.1% HCO$_2$H |
| | TIME (min) | A % | B % |
| | 0.00 | 90 | 10 |
| | 4.50 | 10 | 90 |
| | 5.00 | 10 | 90 |
| | 5.50 | 90 | 10 |
| Flow Rate | 1.5 mL/min |
| Wavelength | UV 220, 230, or 254 nm |

LC-MS Method 2:

| Column | YMC.Pack Pro C18, 50 × 4.6 mm, 3 μm |
| --- | --- |
| Mobile Phase | A: water + 0.1% HCO$_2$H |
| | B: acetonitrile + 0.1% HCO$_2$H |
| | TIME (min) | A % | B % |
| | 0.00 | 90 | 10 |
| | 3.00 | 1 | 99 |
| | 4.30 | 1 | 99 |
| | 5.00 | 90 | 10 |
| Flow Rate | 1.2 mL/min |
| Wavelength | UV 220, 230, or 254 nm |

LC-MS Method 3:

| Column | Sunfire C18, 50 × 4.6 mm, 3.5 μm, 40° C. |
| --- | --- |
| Mobile Phase | A: water + 0.1% F$_3$CCO$_2$H |
| | B: acetonitrile + 0.1% F$_3$CCO$_2$H |
| | TIME (min) | A % | B % |
| | 0.00 | 95 | 5 |
| | 2.00 | 0 | 100 |
| | 2.50 | 0 | 100 |
| | 2.60 | 95 | 5 |
| Flow Rate | 1.5 mL/min |
| Wavelength | UV 210-500 nm |

LC-MS Method 4:

| Column | Sunfire C18, 50 × 4.6 mm, 3.5 μm, 40° C. |
| --- | --- |
| Mobile Phase | A: water + 0.1% F$_3$CCO$_2$H |
| | B: acetonitrile + 0.08% F$_3$CCO$_2$H |
| | TIME (min) | A % | B % |
| | 0.00 | 95 | 5 |
| | 2.00 | 0 | 100 |
| | 3.00 | 0 | 100 |
| | 3.40 | 95 | 5 |
| Flow Rate | 1.5 mL/min |
| Wavelength | UV 210-500 nm |

Preparation of the Starting Compounds

Example I

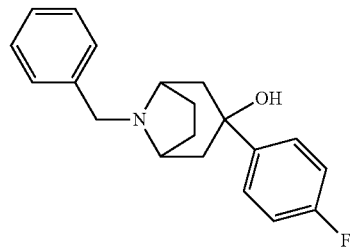 [SMILES: OC1(c2ccc(F)cc2)CC2CCC(C1)N2Cc1ccccc1]

8-Benzyl-3-(4-fluoro-phenyl)-8-aza-bicyclo[3.2.1]octan-3-ol

1-Bromo-4-fluoro-benzene (22.7 g) dissolved in diethylether (100 mL) is added to a solution of n-butyllithium (1.7 mol/L in pentane, 86.8 mL) in diethylether (200 mL) cooled to −35° C. The combined solutions are stirred at −35-−40° C. for 1 h, before 8-benzyl-8-aza-bicyclo[3.2.1]octan-3-one (22.5 g) dissolved in diethylether (150 mL) is added quickly. The solution is warmed to −10° C. within 1 h and then quenched by the addition of aqueous NH$_4$Cl solution. The resulting mixture is extracted with ethyl acetate, the combined extracts are washed with brine, and then 4 M hydrochloric acid is added to the extract phase. The organic phase is separated from the aqueous phase and an oily precipitation formed after the addition. The oily and aqueous phase are basified with 4 M aqueous NaOH solution and the resulting mixture is extracted with ethyl acetate. The organic extracts are dried (Na$_2$SO$_4$) and the solvent is evaporated to give the title compound.

Yield: 21.0 g (75% of theory)

Mass spectrum (ESI$^+$): m/z=312 [M+H]$^+$

Example II

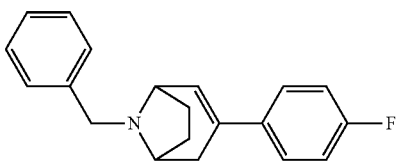 [SMILES: Fc1ccc(C2=CC3CCC(C2)N3Cc2ccccc2)cc1]

8-Benzyl-3-(4-fluoro-phenyl)-8-aza-bicyclo[3.2.1]oct-2-ene

A solution of 8-benzyl-3-(4-fluoro-phenyl)-8-aza-bicyclo[3.2.1]octan-3-ol (21.0 g) in concentrated aqueous hydrochloric acid (80 mL) is stirred at reflux temperature for 1 h. After cooling to ambient temperature, the solution is basified by the addition of 4 M aqueous NaOH solution. The resulting mixture is extracted with ethyl acetate and the combined extracts are dried ($Na_2SO_4$). The solvent is evaporated and the residue is dissolved in ether. Methanesulfonic acid (4.3 mL) is added and the solvent is removed under reduced pressure to give the methanesulfonic acid salt of the title compound.

Yield: 19.1 g (73% of theory)

Example III

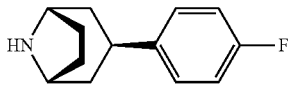

endo-3-(4-Fluoro-phenyl)-8-aza-bicyclo[3.2.1]octane

A mixture of the methanesulfonic acid salt of 8-benzyl-3-(4-fluoro-phenyl)-8-aza-bicyclo[3.2.1]oct-2-ene (from Example II; 19.1 g) and 5% palladium on carbon (2 g) in methanol (170 mL) is shaken under hydrogen atmosphere (5 bar) at 55° C. overnight. Then, the catalyst is separated by filtration and the filtrate is concentrated. The residue is taken up in ethyl acetate and washed with saturated aqueous $K_2CO_3$ solution. The organic phase is concentrated again and the residue is purified by chromatography on silica gel ($CH_2Cl_2$/MeOH 99:1→9:1).

Yield: 3.5 g (35% of theory)

LC (method 1): $t_R$=1.82 min; Mass spectrum (ESI$^+$): m/z=206 [M+H]$^+$

Example IV

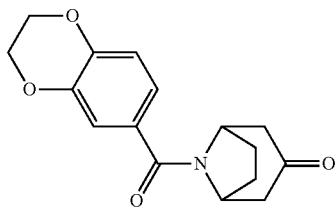 [SMILES: O=C1CC2CCC(C1)N2C(=O)c1ccc2c(c1)OCCO2]

8-(2,3-Dihydro-benzo[1,4]dioxine-6-carbonyl)-8-aza-bicyclo[3.2.1]octan-3-one

Oxalyl chloride (10 mL) is added to 2,3-dihydro-benzo[1,4]dioxine-6-carboxylic acid (14.9 g) dissolved in dichloromethane (100 mL). After the addition of N,N-dimethylformamide (0.5 mL), the mixture is stirred at room temperature overnight and then concentrated. The residue is taken up in dichloromethane (100 mL) and added to a mixture of nortropinone hydrochloride (10.0 g) and potassium carbonate (12.0 g) in dichloromethane (50 mL). Then, pyridine (18 mL) is added and the mixture is stirred at room temperature overnight. The mixture is concentrated and the residue is taken up in dichloromethane and washed with 1 M aqueous hydrochloric acid, 1 M aqueous NaOH solution, and brine. After drying ($Na_2SO_4$), the solvent is removed under reduced pressure to yield the title compound.

Yield: 17.3 g (75% of theory)

Mass spectrum (ESI$^+$): m/z=288 [M+H]$^+$

Example V

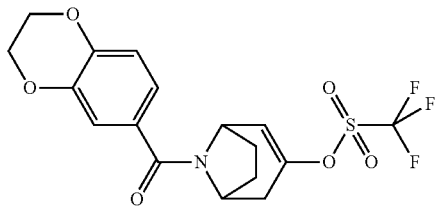 [SMILES: O=C(c1ccc2c(c1)OCCO2)N1C2C=C(OS(=O)(=O)C(F)(F)F)CC1CC2]

Trifluoro-methanesulfonic acid 8-(2,3-dihydro-benzo[1,4]dioxine-6-carbonyl)-8-aza-bicyclo[3.2.1]oct-2-en-3-yl ester Lithium bis(trimethylsilyl)amide (1 mol/L in tetrahydrofuran, 44 mL) is added to a solution of 8-(2,3-dihydro-benzo[1,4]dioxine-6-carbonyl)-8-aza-bicyclo[3.2.1]octan-3-one (11.2 g) in tetrahydrofuran (200 mL) cooled to −78° C. The solution is stirred at −78° C. for 1 h, before 2-[N,N-(bistrifluoromethylsulfonyl)amino]-5-chloropyridine (17.8 g) dissolved in tetrahydrofuran (200 mL) is added dropwise over a period of 1 h. The resulting solution is stirred for another 0.5 h at this temperature and then warmed to room temperature by removing the cooling bath. Aqueous $NaHCO_3$ solution is added, the resulting mixture is extracted with ethyl acetate, and the combined extracts are dried ($Na_2SO_4$). After removal of the solvent under reduced pressure, the residue is purified by chromatography on silica gel (cyclohexane/ethyl acetate 1:0→1:1).

Yield: 11.7 g (72% of theory)

Mass spectrum (ESI$^+$): m/z=420 [M+H]$^+$

The following compounds are obtained analogously to Example V:

(1) Trifluoro-methanesulfonic acid 8-methyl-8-aza-bicyclo[3.2.1]oct-2-en-3-yl ester

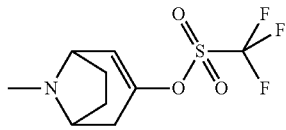 [SMILES: CN1C2C=C(OS(=O)(=O)C(F)(F)F)CC1CC2]

Mass spectrum (ESI$^+$): m/z=272 [M+H]$^+$

Alternatively, the title compound is obtained from 8-methyl-8-aza-bicyclo[3.2.1]octan-3-one using potassium bis(trimethylsilyl)amide as base and N,N-bis(trifluoromethylsulfonyl)aniline as sulfonylating agent.

(2) Trifluoro-methanesulfonic acid 8-benzyl-8-aza-bicyclo[3.2.1]oct-2-en-3-yl ester

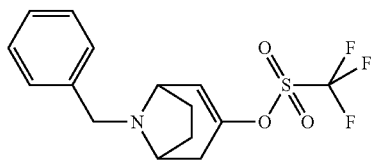 [SMILES: O=S(=O)(OC1=CC2CCC(C1)N2Cc1ccccc1)C(F)(F)F]

Mass spectrum (ESI$^+$): m/z=348 [M+H]$^+$

Alternatively, the title compound is obtained from 8-benzyl-8-aza-bicyclo[3.2.1]octan-3-one using sodium bis(trimethylsilyl)amide as base and N,N-bis(trifluoromethylsulfonyl)aniline as sulfonylating agent.

Example VI

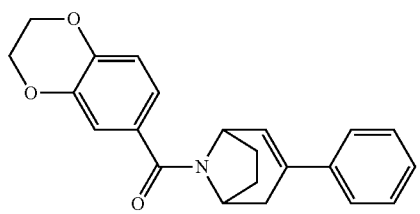 [SMILES: O=C(c1ccc2c(c1)OCCO2)N1C2C=C(c3ccccc3)CC1CC2]

(2,3-Dihydro-benzo[1,4]dioxin-6-yl)-(3-phenyl-8-aza-bicyclo[3.2.1]oct-2-en-8-yl)-methanone 2 M aqueous Na$_2$CO$_3$ solution (1.0 mL) is added to a flask charged with a stir bar, trifluoro-methanesulfonic acid 8-(2,3-dihydro-benzo[1,4]dioxine-6-carbonyl)-8-aza-bicyclo[3.2.1]oct-2-en-3-yl ester (0.40 g), phenylboronic acid (0.13 g), lithium chloride (87 mg), Pd(PPh$_3$)$_4$ (60 mg), water (2 mL), and 1,2-dimethoxyethane (10 mL) in argon atmosphere. The resulting mixture is stirred at reflux temperature for 4 h. After cooling to ambient temperature, brine is added and the mixture is extracted with ethyl acetate. The combined extracts are dried (Na$_2$SO$_4$) and the solvent is removed under reduced pressure. The residue is purified by chromatography on silica gel (cyclohexane/ethyl acetate 1:0→2:1).

Yield: 0.31 g (95% of theory)

Mass spectrum (ESI$^+$): m/z=348 [M+H]$^+$

The following compounds are obtained analogously to Example VI:

(1) 3-[8-(2,3-Dihydro-benzo[1,4]dioxine-6-carbonyl)-8-aza-bicyclo[3.2.1]oct-2-en-3-yl]-4-fluoro-benzonitrile

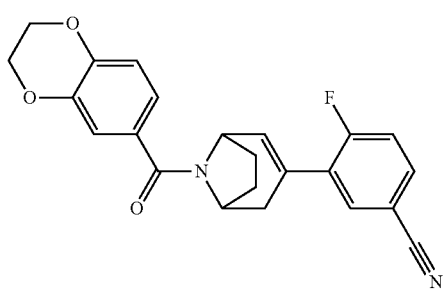 [SMILES: N#Cc1ccc(F)c(C2=CC3CCC(C2)N3C(=O)c2ccc3c(c2)OCCO3)c1]

(2) 4-[8-(2,3-Dihydro-benzo[1,4]dioxine-6-carbonyl)-8-aza-bicyclo[3.2.1]oct-2-en-3-yl]-benzonitrile

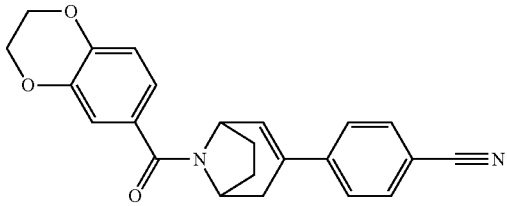 [SMILES: N#Cc1ccc(C2=CC3CCC(C2)N3C(=O)c2ccc3c(c2)OCCO3)cc1]

Mass spectrum (ESI$^+$): m/z=373 [M+H]$^+$ (3) 3-[8-(2,3-Dihydro-benzo[1,4]dioxine-6-carbonyl)-8-aza-bicyclo[3.2.1]oct-2-en-3-yl]-benzonitrile

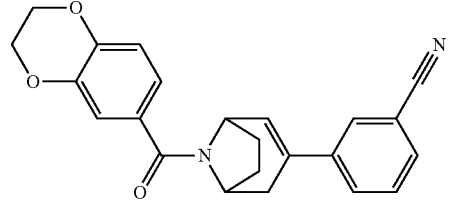 [SMILES: N#Cc1cccc(C2=CC3CCC(C2)N3C(=O)c2ccc3c(c2)OCCO3)c1]

Mass spectrum (ESI$^+$): m/z=373 [M+H]$^+$ (4) (2,3-Dihydro-benzo[1,4]dioxin-6-yl)-(3-pyridin-4-yl-8-aza-bicyclo[3.2.1]oct-2-en-8-yl)-methanone

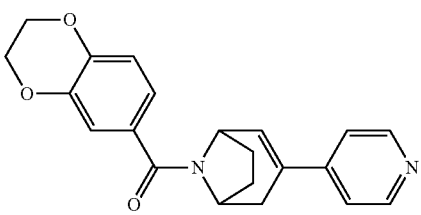 [SMILES: O=C(c1ccc2c(c1)OCCO2)N1C2C=C(c3ccncc3)CC1CC2]

Mass spectrum (ESI$^+$): m/z=349 [M+H]$^+$ (5) (3-Biphenyl-3-yl-8-aza-bicyclo[3.2.1]oct-2-en-8-yl)-(2,3-dihydro-benzo[1,4]dioxin-6-yl)-methanone

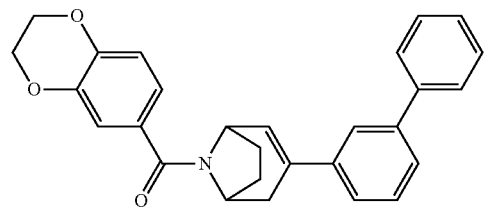 [SMILES: O=C(c1ccc2c(c1)OCCO2)N1C2C=C(c3cccc(-c4ccccc4)c3)CC1CC2]

Mass spectrum (ESI$^+$): m/z=424 [M+H]$^+$ (6) [3-(3-Chloro-4-fluoro-phenyl)-8-aza-bicyclo[3.2.1]oct-2-en-8-yl]-(2,3-dihydro-benzo[1,4]dioxin-6-yl)-methanone

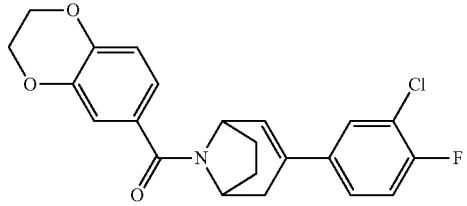 [SMILES: O=C(c1ccc2c(c1)OCCO2)N1C2C=C(c3ccc(F)c(Cl)c3)CC1CC2]

Mass spectrum (ESI$^+$): m/z=400/402 (Cl) [M+H]$^+$ (7) [3-(4-Chloro-phenyl)-8-aza-bicyclo[3.2.1]oct-2-en-8-yl]-(2,3-dihydro-benzo[1,4]dioxin-6-yl)-methanone

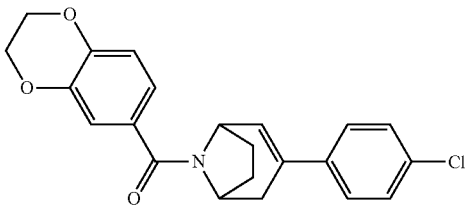 [SMILES: O=C(c1ccc2c(c1)OCCO2)N1C2C=C(c3ccc(Cl)cc3)CC1CC2]

Mass spectrum (ESI$^+$): m/z=382/384 (Cl) [M+H]$^+$ (8) 3-[8-(2,3-Dihydro-benzo[1,4]dioxine-6-carbonyl)-8-aza-bicyclo[3.2.1]oct-2-en-3-yl]-benzamide

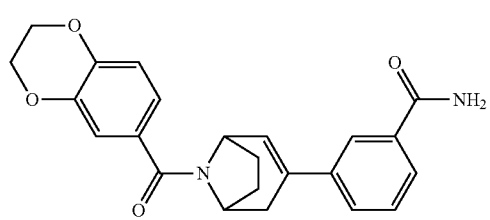 [SMILES: NC(=O)c1cccc(C2=CC3CCC(C2)N3C(=O)c2ccc3c(c2)OCCO3)c1]

Mass spectrum (ESI$^+$): m/z=391 [M+H]$^+$ (9) 3-(4-Fluoro-phenyl)-8-methyl-8-aza-bicyclo[3.2.1]oct-2-ene

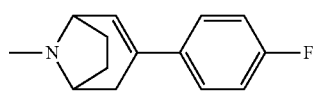 [SMILES: CN1C2C=C(c3ccc(F)cc3)CC1CC2]

Mass spectrum (ESI$^+$): m/z=218 [M+H]$^+$

(10) 8-Benzyl-3-(3,4-difluoro-phenyl)-8-aza-bicyclo[3.2.1]oct-2-ene

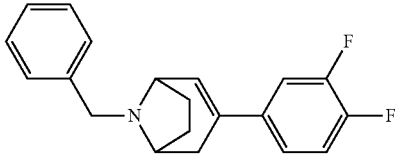

Mass spectrum (ESI$^+$): m/z=312 [M+H]$^+$

(11) 8-Benzyl-3-(4-methoxy-phenyl)-8-aza-bicyclo[3.2.1]oct-2-ene

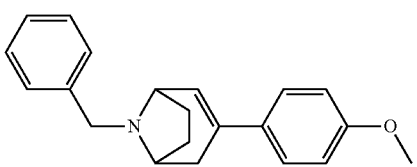 [SMILES: COc1ccc(C2=CC3CCC(C2)N3Cc2ccccc2)cc1]

(12) 8-Benzyl-3-(3-methoxy-phenyl)-8-aza-bicyclo[3.2.1]oct-2-ene

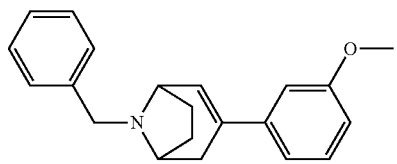

(13) 8-Benzyl-3-p-tolyl-8-aza-bicyclo[3.2.1]oct-2-ene

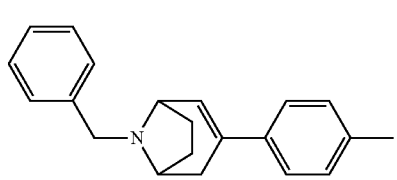 [SMILES: Cc1ccc(C2=CC3CCC(C2)N3Cc2ccccc2)cc1]

(14) 8-Benzyl-3-(4-isopropyl-phenyl)-8-aza-bicyclo[3.2.1]oct-2-ene

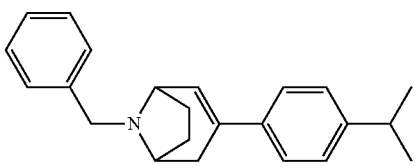 [SMILES: CC(C)c1ccc(C2=CC3CCC(C2)N3Cc2ccccc2)cc1]

Mass spectrum (ESI$^+$): m/z=318 [M+H]$^+$

(15) 8-Benzyl-3-(4-trifluoromethoxy-phenyl)-8-aza-bicyclo[3.2.1]oct-2-ene

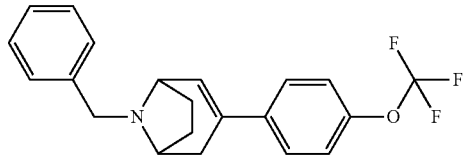 [SMILES: FC(F)(F)Oc1ccc(C2=CC3CCC(C2)N3Cc2ccccc2)cc1]

Mass spectrum (ESI⁺): m/z=360 [M+H]⁺

(16) 8-Benzyl-3-(4-phenoxy-phenyl)-8-aza-bicyclo[3.2.1]oct-2-ene

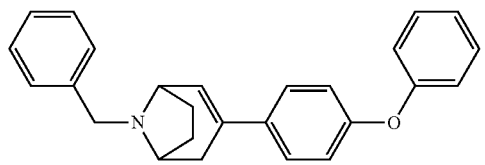 [SMILES: C1=C(c2ccc(Oc3ccccc3)cc2)CC2CCC1N2Cc1ccccc1]

(17) 8-Benzyl-3-(4-trimethylsilanyl-phenyl)-8-aza-bicyclo[3.2.1]oct-2-ene

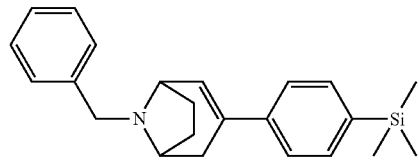 [SMILES: C[Si](C)(C)c1ccc(C2=CC3CCC(C2)N3Cc2ccccc2)cc1]

(18) 4-(8-Benzyl-8-aza-bicyclo[3.2.1]oct-2-en-3-yl)-benzoic acid methyl ester

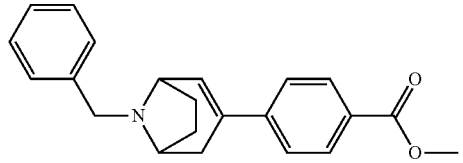 [SMILES: COC(=O)c1ccc(C2=CC3CCC(C2)N3Cc2ccccc2)cc1]

(19) 8-Benzyl-3-(4-methoxymethyl-phenyl)-8-aza-bicyclo[3.2.1]oct-2-ene

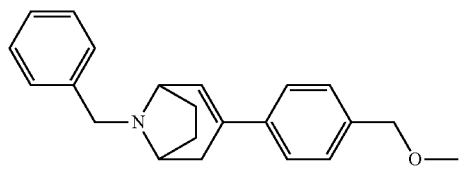 [SMILES: COCc1ccc(C2=CC3CCC(C2)N3Cc2ccccc2)cc1]

(20) 8-Benzyl-3-thiophen-2-yl-8-aza-bicyclo[3.2.1]oct-2-ene

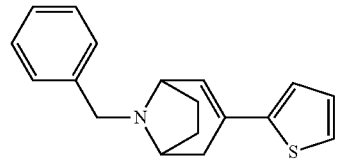 [SMILES: C1=C(c2cccs2)CC2CCC1N2Cc1ccccc1]

(21) 8-Benzyl-3-thiophen-3-yl-8-aza-bicyclo[3.2.1]oct-2-ene

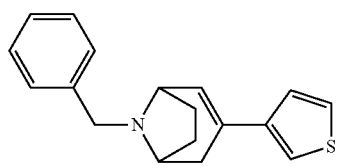 [SMILES: C1=C(c2ccsc2)CC2CCC1N2Cc1ccccc1]

(22) 8-Benzyl-3-pyridin-3-yl-8-aza-bicyclo[3.2.1]oct-2-ene

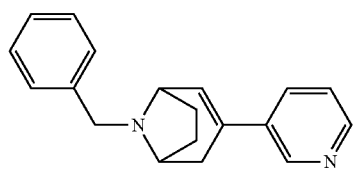

(23) 8-Benzyl-3-pyridin-3-yl-8-aza-bicyclo[3.2.1]oct-2-ene

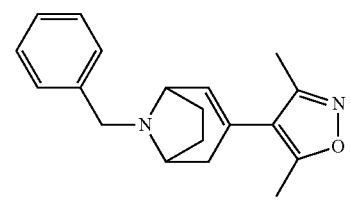 [SMILES: Cc1noc(C)c1C1=CC2CCC(C1)N2Cc1ccccc1]

(24) 8-Benzyl-3-o-tolyl-8-aza-bicyclo[3.2.1]oct-2-ene

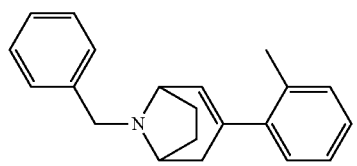 [SMILES: Cc1ccccc1C1=CC2CCC(C1)N2Cc1ccccc1]

Mass spectrum (ESI⁺): m/z=290 [M+H]⁺

(25) 8-Benzyl-3-(2-methoxy-phenyl)-8-aza-bicyclo[3.2.1]oct-2-ene

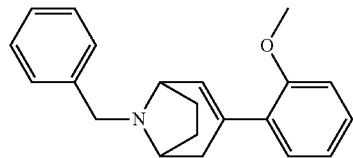 [SMILES: COc1ccccc1C1=CC2CCC(C1)N2Cc1ccccc1]

Mass spectrum (ESI$^+$): m/z=306 [M+H]$^+$

(26) 8-Benzyl-3-(2,6-difluoro-phenyl)-8-aza-bicyclo[3.2.1]oct-2-ene

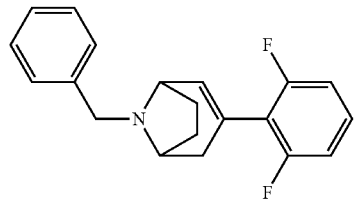 [SMILES: Fc1cccc(F)c1C1=CC2CCC(C1)N2Cc1ccccc1]

Mass spectrum (ESI$^+$): m/z=312 [M+H]$^+$

(27) 8-Benzyl-3-(2,4-difluoro-phenyl)-8-aza-bicyclo[3.2.1]oct-2-ene

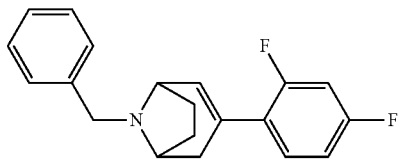

Mass spectrum (ESI$^+$): m/z=312 [M+H]$^+$

(28) 8-Benzyl-3-naphthalen-2-yl-8-aza-bicyclo[3.2.1]oct-2-ene

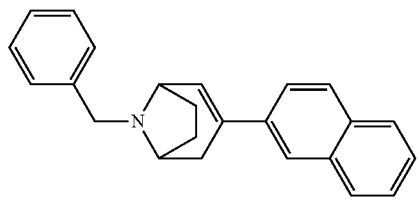 [SMILES: C1=C(c2ccc3ccccc3c2)CC2CCC1N2Cc1ccccc1]

Mass spectrum (ESI$^+$): m/z=326 [M+H]$^+$

(29) 8-Benzyl-3-pyrimidin-5-yl-8-aza-bicyclo[3.2.1]oct-2-ene

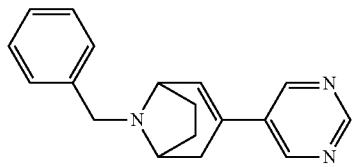 [SMILES: C1=C(c2cncnc2)CC2CCC1N2Cc1ccccc1]

Mass spectrum (ESI$^+$): m/z=278 [M+H]$^+$

(30) 8-Benzyl-3-furan-3-yl-8-aza-bicyclo[3.2.1]oct-2-ene

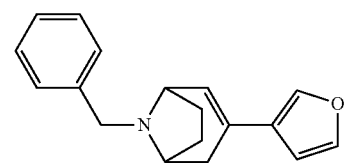 [SMILES: C1=C(c2ccoc2)CC2CCC1N2Cc1ccccc1]

Mass spectrum (ESI$^+$): m/z=266 [M+H]$^+$

(31) 8-Benzyl-3-pyrimidin-5-yl-8-aza-bicyclo[3.2.1]oct-2-ene

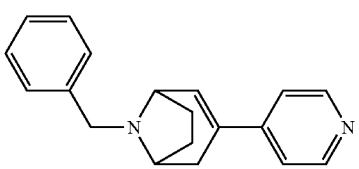 [SMILES: C1=C(c2ccncc2)CC2CCC1N2Cc1ccccc1]

(32) [3-(4-Chloro-2-fluoro-phenyl)-8-aza-bicyclo[3.2.1]oct-2-en-8-yl]-(2,3-dihydro-benzo[1,4]dioxin-6-yl)-methanone

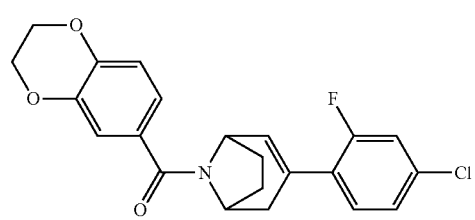 [SMILES: O=C(c1ccc2c(c1)OCCO2)N1C2C=C(c3ccc(Cl)cc3F)CC1CC2]

Mass spectrum (ESI$^+$): m/z=400/402 (Cl) [M+H]$^+$

(33) [3-(4-Chloro-2-fluoro-phenyl)-8-aza-bicyclo[3.2.1]oct-2-en-8-yl]-(2,3-dihydro-benzo[1,4]dioxin-6-yl)-methanone

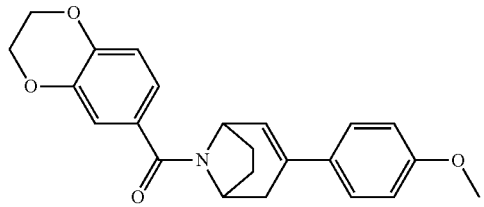 [SMILES: COc1ccc(C2=CC3CCC(C2)N3C(=O)c2ccc3c(c2)OCCO3)cc1]

Example VII

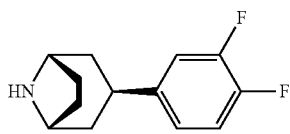

endo-3-(3,4-Difluoro-phenyl)-8-aza-bicyclo[3.2.1]octane

A mixture of 8-benzyl-3-(3,4-difluoro-phenyl)-8-aza-bicyclo[3.2.1]oct-2-ene (0.30 g) and 5% palladium on carbon (40 mg) in ethanol (5 mL) containing acetic acid (0.15 mL) is shaken under hydrogen atmosphere (5 bar) at 60° C. overnight. Then, the catalyst is separated by filtration and the filtrate is concentrated. The residue is purified by chromatography on silica gel (dichloromethane/methanol 99:1→9:1).

Yield: 0.16 g (74% of theory)

The following compounds are obtained analogously to Example VII:

(1) endo-3-(4-Methoxy-phenyl)-8-aza-bicyclo[3.2.1]octane

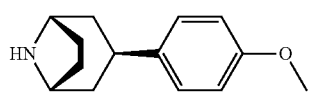

(2) endo-3-p-Tolyl-8-aza-bicyclo[3.2.1]octane

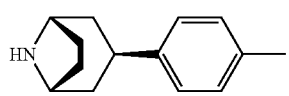

(3) endo-3-(3-Methoxy-phenyl)-8-aza-bicyclo[3.2.1]octane

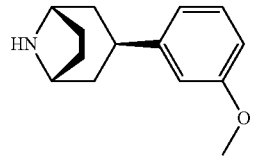

(4) endo-3-(4-Trifluoromethoxy-phenyl)-8-aza-bicyclo[3.2.1]octane

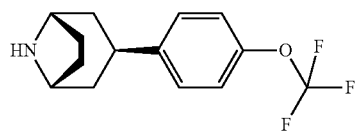

(5) endo-3-(4-Isopropyl-phenyl)-8-aza-bicyclo[3.2.1]octane

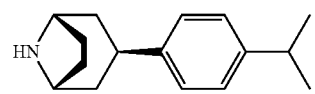

(6) endo-3-(4-Phenoxy-phenyl)-8-aza-bicyclo[3.2.1]octane

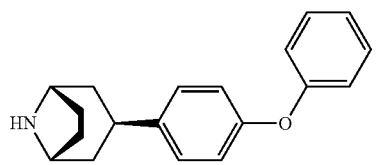

(7) endo-3-(4-Trimethylsilanyl-phenyl)-8-aza-bicyclo[3.2.1]octane

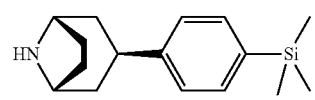

(8) endo-4-(8-Aza-bicyclo[3.2.1]oct-3-yl)-benzoic acid methyl ester

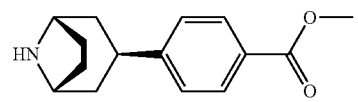

(9) endo-3-(4-Methoxymethyl-phenyl)-8-aza-bicyclo[3.2.1]octane

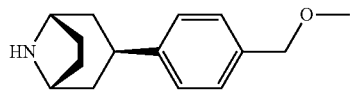

(10) endo-3-Pyridin-3-yl-8-aza-bicyclo[3.2.1]octane

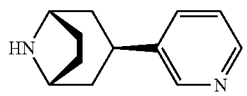

(11) endo-3-(3,5-Dimethyl-isoxazol-4-yl)-8-aza-bicyclo[3.2.1]octane

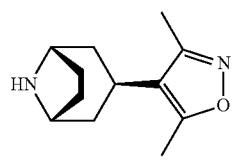

(12) endo-3-(2-Methoxy-phenyl)-8-aza-bicyclo[3.2.1]octane

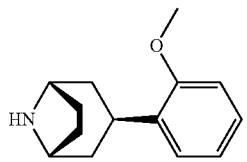

Mass spectrum (ESI$^+$): m/z=218 [M+H]$^+$

(13) endo-3-o-Tolyl-8-aza-bicyclo[3.2.1]octane

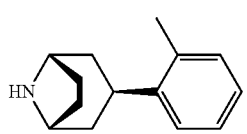

(14) endo-3-(2,6-Difluoro-phenyl)-8-aza-bicyclo[3.2.1]octane

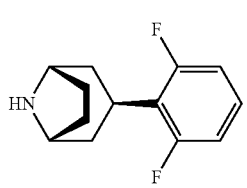

Mass spectrum (ESI$^+$): m/z=224 [M+H]$^+$

(15) endo-3-(2,4-Difluoro-phenyl)-8-aza-bicyclo[3.2.1]octane

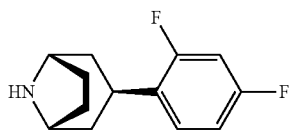

Mass spectrum (ESI$^+$): m/z=224 [M+H]$^+$

(16)
endo-3-Naphthalen-2-yl-8-aza-bicyclo[3.2.1]octane

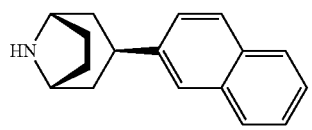

Mass spectrum (ESI$^+$): m/z=238 [M+H]$^+$

Remark: The products obtained in analogy to the procedure described above mostly have high isomeric purity (endo/exo in most cases >9:1).

Example VIII

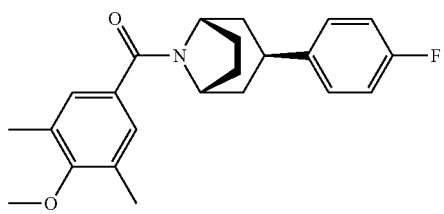

endo-[3-(4-Fluoro-phenyl)-8-aza-bicyclo[3.2.1]oct-8-yl]-(4-methoxy-3,5-dimethyl-phenyl)-methanone 2-(1H-Benzotriazol-1-yl)-1,1,3,3-tetramethyluronium tetrafluoroborate (TBTU; 96 mg) is added to a solution of 4-methoxy-3,5-dimethyl-benzoic acid (80 mg) and ethyl-di-isopropyl-amine (0.10 mL) in N,N-dimethylformamide (3 mL) at room temperature. The resulting solution is stirred for 30 min, before endo-3-(4-fluoro-phenyl)-8-aza-bicyclo[3.2.1]octane (0.13 g) is added. The solution is stirred at room temperature overnight. Then, water is added and the resulting mixture is extracted with ethyl acetate. The combined extracts are dried (Na$_2$SO$_4$) and concentrated. The residue is purified by chromatography on silica gel (caclohexane/ethyl acetate 1:1) to afford the title compound.

Yield: 70 mg (72% of theory)

LC (method 1): t$_R$=4.50 min; Mass spectrum (ESI$^+$): m/z=368 [M+H]$^+$

Example IX

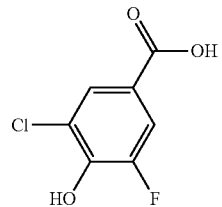 [SMILES: O=C(O)c1cc(F)c(O)c(Cl)c1]

3-Chloro-5-fluoro-4-hydroxy-benzoic acid

Sulfuryl chloride (4.7 mL) is added to a solution of 3-fluoro-4-hydroxy-benzoic acid (2.97 g) in acetic acid (20 mL) stirred at 50° C. in N,N-dimethylformamide (3 mL) at room temperature. The resulting solution is stirred for 2 h, prior to the addition of another portion of sulfuryl chloride (1.0 mL). The solution is stirred at 60° C. for another 1.5 h and then cooled to ambient temperature. The solution is poured into ice-cold water and the precipitate formed is separated by filtration, washed with ice-cold water, and dried at 50° C. to afford the title compound as a beige solid.

Yield: 2.15 g (57% of theory)

LC (method 1): $t_R$=2.11 min; Mass spectrum (ESI$^-$): m/z=189 [M−H]$^-$

Preparation of the End Compounds

Procedure A (Described for Example 1, Table 3)

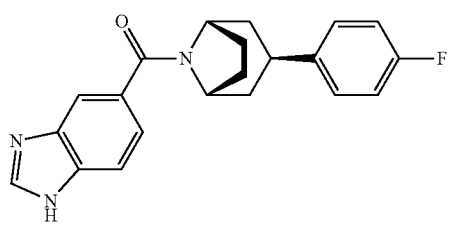

endo-(1H-Benzoimidazol-5-yl)-[3-(4-fluoro-phenyl)-8-aza-bicyclo[3.2.1]oct-8-yl]-methanone 2-(1H-Benzotriazol-1-yl)-1,1,3,3-tetramethyluronium tetrafluoroborate (0.20 g; alternatively, 2-(7-aza-1H-benzotriazol-1-yl)-1,1,3,3-tetramethyluronium hexafluorophosphate may be used) is added to a solution of 1H-benzoimidazole-5-carboxylic acid (0.10 g) and ethyl-diisopropyl-amine (0.40 mL) in N,N-dimethylformamide (4 mL) chilled in an ice bath. The resulting solution is stirred for 15 min, before endo-3-(4-fluoro-phenyl)-8-aza-bicyclo[3.2.1]octane (0.13 g) is added. The resulting solution is warmed to room temperature and stirred overnight. Then, water is added and the resulting mixture is extracted with ethyl acetate. The combined extracts are dried (Na$_2$SO$_4$) and concentrated. The residue is purified by HPLC on reversed phase (H$_2$O/MeCN) to give the title compound.

Yield: 85 mg (39% of theory)

LC (method 2): $t_R$=2.34 min; Mass spectrum (ESI$^+$): m/z=350 [M+H]$^+$

Procedure B (Described for Example 133, Table 3)

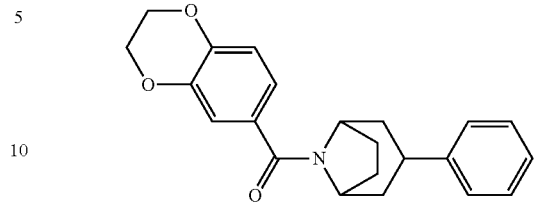

(2,3-Dihydro-benzo[1,4]dioxin-6-yl)-(3-phenyl-8-aza-bicyclo[3.2.1]oct-8-yl)-methanone, 1:1 mixture of endo and exo isomer PtO$_2$ (40 mg) is added to a solution of (2,3-dihydro-benzo[1,4]dioxin-6-yl)-(3-phenyl-8-aza-bicyclo[3.2.1]oct-2-en-8-yl)-methanone (0.40 g) in methanol (5 mL). The resulting mixture is shaken in hydrogen atmosphere (1 bar) at room temperature for 6 h. Then, the mixture is filtered and the filtrate is concentrated under reduced pressure. The residue is purified by chromatography on silica gel (dichloromethane/methanol 1:0→9:1) to give the title product as a ca. 1:1 mixture of endo and exo isomer.

Yield: 0.15 g (37% of theory)

Mass spectrum (ESI$^+$): m/z=350 [M+H]$^+$

Procedure C (Described for Example 141, Table 3)

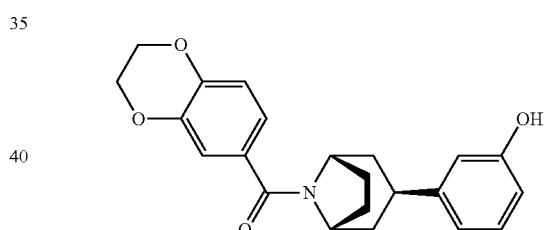

endo-(2,3-Dihydro-benzo[1,4]dioxin-6-yl)-[3-(3-hydroxy-phenyl)-8-aza-bicyclo[3.2.1]oct-8-yl]-methanone Boron tribromide (1 mol/L in dichloromethane, 0.38 mL) is added to a solution of endo-(2,3-dihydro-benzo[1,4]dioxin-6-yl)-[3-(3-methoxy-phenyl)-8-aza-bicyclo[3.2.1]oct-8-yl]-methanone (0.15 g) in dichloromethane (3 mL) chilled in an ice bath. The resulting solution is warmed to ca. 45° C. and stirred at this temperature for 1 h. Then, another portion of boron tribromide (1 mol/L in dichloromethane, 0.35 mL) is added and the solution is further stirred for another 2 h. After cooling to room temperature, aqueous K$_2$CO$_3$ solution is added, the resulting mixture is acidified with 1 M hydrochloric acid, and extracted with ethyl acetate. The combined extracts are dried (Na$_2$SO$_4$) and the solvent is evaporated. Depending on the purity of the product obtained thereafter, the compound is further purified by chromatography on silica gel (dichloromethane/methanol).

Yield: 0.14 g (99% of theory)

Mass spectrum (ESI$^+$): m/z=366 [M+H]$^+$

Procedure D (Described for Example 155, Table 3)

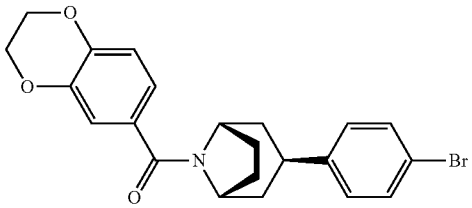

endo-[3-(4-Bromo-phenyl)-8-aza-bicyclo[3.2.1]oct-8-yl]-(2,3-dihydro-benzo[1,4]dioxin-6-yl)-methanone Bromine (1 mol/L in dichloromethane, 0.5 mL) is added to a solution of endo-(2,3-dihydro-benzo[1,4]dioxin-6-yl)-[3-(4-trimethylsilyl-phenyl)-8-aza-bicyclo[3.2.1]oct-8-yl]-methanone (82 mg) in dichloromethane (2 mL) chilled in an ice bath. The ice bath is removed and the solution is stirred at room temperature for 1 h. Then, aqueous solutions of $Na_2S_2O_3$ and $NaHCO_3$ are added and the mixture is extracted with ethyl acetate. The combined extracts are dried ($Na_2SO_4$) and the solvent is evaporated. The residue is purified by chromatography on silica gel (dichloromethane/methanol 1:0→19:1).

Yield: 50 mg (52% of theory)
Mass spectrum (ESI$^+$): m/z=428/430 (Br) [M+H]$^+$ Procedure E (Described for Example 158, Table 3)

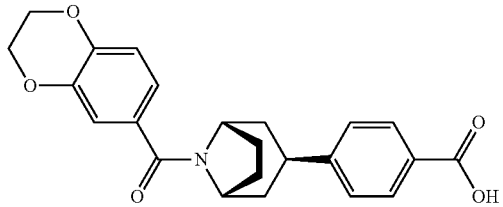

endo-4-[8-(2,3-Dihydro-benzo[1,4]dioxine-6-carbonyl)-8-aza-bicyclo[3.2.1]oct-3-yl]-benzoic acid 4 M aqueous KOH solution (0.25 mL) is added to a solution of endo-4-[8-(2,3-dihydro-benzo[1,4]dioxine-6-carbonyl)-8-aza-bicyclo[3.2.1]oct-3-yl]-benzoic acid methyl ester (80 mg) in methanol (3 mL). The resulting solution is stirred at room temperature for 3 h and is then acidified using 1 M hydrochloric acid. Ethyl acetate is added and the precipitate formed is separated by filtration and dried to give the title compound.

Yield: 37 mg (48% of theory)
Mass spectrum (ESI$^+$): m/z=394 [M+H]$^+$

Procedure F (Described for Example 180, Table 3)

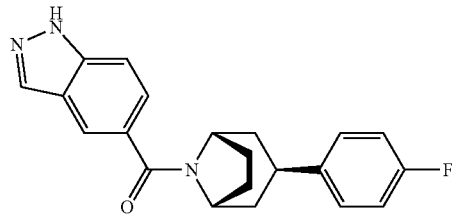

endo-[3-(4-Fluoro-phenyl)-8-aza-bicyclo[3.2.1]oct-8-yl]-(1H-indazol-5-yl)-methanone 1-Propanephosphonic acid cyclic anhydride (0.63 mL) is added to a solution of endo-3-(4-fluoro-phenyl)-8-aza-bicyclo[3.2.1]octane (methanesulfonic acid salt, 80 mg), 1H-indazole-5-carboxylic acid (43 mg), and triethylamine (0.19 mL) in tetrahydrofuran (3 mL) at room temperature. The resulting solution is stirred at room temperature for 4 h, prior to the addition of another protion of 1-propanephosphonic acid cyclic anhydride (0.30 mL) and triethylamine (0.09 mL). The solution is further stirred overnight and then acidified using 1 M hydrochloric acid. The resulting mixture is extracted with ethyl acetate and the combined extracts are dried ($Na_2SO_4$). The solvent is evaporated and the residue is purified by chromatography on siilica gel (dichloromethane/methanol 1:0→9:1) to afford the title compound.

Yield: 30 mg (32% of theory)
LC (method 1): $t_R$=3.44 min; Mass spectrum (ESI$^+$): m/z=350 [M+H]$^+$

TABLE 3

Compilation of synthesized end compounds

| Example No. | Chemical Name/Structure/Remarks | Prepared in analogy to Procedure | Characterization |
|---|---|---|---|
| 1 | endo-(1H-Benzoimidazol-5-yl)-[3-(4-fluoro-phenyl)-8-aza-bicyclo[3.2.1]oct-8-yl]-methanone | A | LC (method 2): $t_R$ = 2.34 min; MS (ESI$^+$): m/z = 350 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 2 | endo-4-[3-(4-Fluoro-phenyl)-8-aza-bicyclo[3.2.1]octane-8-carbonyl]-benzamide | A | LC (method 2): tR = 3.00 min; MS (ESI$^+$): m/z = 353 [M + H]$^+$ |
| 3 | endo-(2,3-Dihydro-benzo[1,4]dioxin-6-yl)-[3-(4-fluoro-phenyl)-8-aza-bicyclo[3.2.1]oct-8-yl]-methanone | A | Mass spectrum (ESI$^+$): m/z = 368 [M + H]$^+$ |
| 4 | endo-(7-Difluoromethyl-5-methyl-pyrazolo[1,5-a]pyrimidin-3-yl)-[3-(4-fluoro-phenyl)-8-aza-bicyclo[3.2.1]oct-8-yl]-methanone | A | Mass spectrum (ESI$^+$): m/z = 415 [M + H]$^+$ |
| 5 | endo-(3,5-Dimethyl-isoxazol-4-yl)-[3-(4-fluoro-phenyl)-8-aza-bicyclo[3.2.1]oct-8-yl]-methanone | A | Mass spectrum (ESI$^+$): m/z = 329 [M + H]$^+$ |
| 6 | endo-[3-(4-Fluoro-phenyl)-8-aza-bicyclo[3.2.1]oct-8-yl]-(1,4,5,6-tetrahydro-cyclopentapyrazol-3-yl)-methanone | A | Mass spectrum (ESI$^+$): m/z = 340 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 7 | endo-[3-(4-Fluoro-phenyl)-8-aza-bicyclo[3.2.1]oct-8-yl]-thiophen-2-yl-methanone | A | Mass spectrum (ESI$^+$): m/z = 316 [M + H]$^+$ |
| 8 | endo-3-[3-(4-Fluoro-phenyl)-8-aza-bicyclo[3.2.1]octane-8-carbonyl]-5-methyl-4H-pyrazolo[1,5-a]pyrimidin-7-one | A | Mass spectrum (ESI$^+$): m/z = 381 [M + H]$^+$ |
| 9 | endo-5-(3-p-Tolyl-8-aza-bicyclo[3.2.1]octane-8-carbonyl)-thiophene-2-carboxylic acid methyl ester | A | Mass spectrum (ESI$^+$): m/z = 370 [M + H]$^+$ |
| 10 | endo-[3-(4-Fluoro-phenyl)-8-aza-bicyclo[3.2.1]oct-8-yl]-pyridin-3-yl-methanone | A | Mass spectrum (ESI$^+$): m/z = 311 [M + H]$^+$ |
| 11 | endo-(5-tert-Butyl-2H-pyrazol-3-yl)-[3-(4-fluoro-phenyl)-8-aza-bicyclo[3.2.1]oct-8-yl]-methanone | A | Mass spectrum (ESI$^+$): m/z = 356 [M + H]$^+$ |
| 12 | endo-(3,5-Difluoro-phenyl)-[3-(4-fluoro-phenyl)-8-aza-bicyclo[3.2.1]oct-8-yl]-methanone | A | Mass spectrum (ESI$^+$): m/z = 346 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 13 | endo-Thiazol-4-yl-(3-p-tolyl-8-aza-bicyclo[3.2.1]oct-8-yl)-methanone 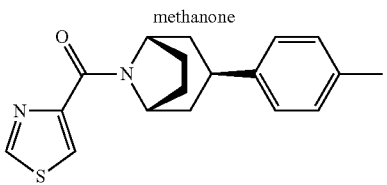 | A | Mass spectrum (ESI+): m/z = 313 [M + H]+ |
| 14 | endo-[5-(4-Chloro-pyrazol-1-ylmethyl)-furan-2-yl]-(3-p-tolyl-8-aza-bicyclo[3.2.1]oct-8-yl)-methanone 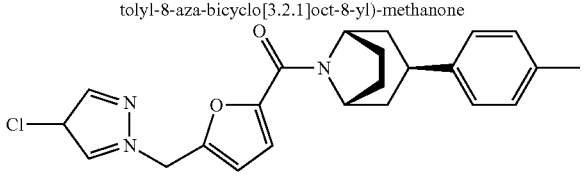 | A | Mass spectrum (ESI+): m/z = 410/412 (Cl) [M + H]+ |
| 15 | endo-Thiophen-2-yl-(3-p-tolyl-8-aza-bicyclo[3.2.1]oct-8-yl)-methanone 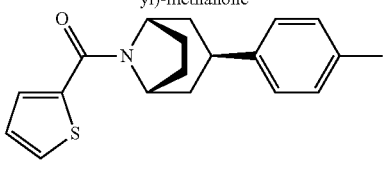 | A | Mass spectrum (ESI+): m/z = 312 [M + H]+ |
| 16 | endo-[3-(4-Fluoro-phenyl)-8-aza-bicyclo[3.2.1]oct-8-yl]-(2-hydroxy-6-methyl-pyridin-3-yl)-methanone 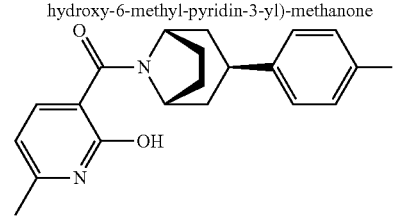 | A | Mass spectrum (ESI+): m/z = 341 [M + H]+ |
| 17 | endo-Furan-2-yl-(3-p-tolyl-8-aza-bicyclo[3.2.1]oct-8-yl)-methanone 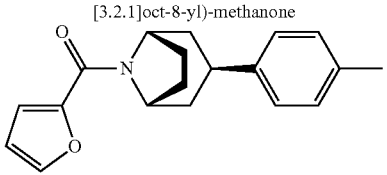 | A | Mass spectrum (ESI+): m/z = 296 [M + H]+ |
| 18 | endo-[3-(4-Fluoro-phenyl)-8-aza-bicyclo[3.2.1]oct-8-yl]-pyridin-2-yl-methanone 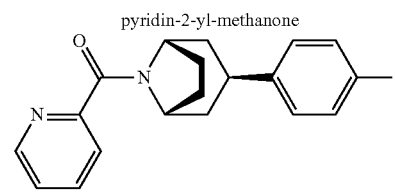 | A | Mass spectrum (ESI+): m/z = 311 [M + H]+ |

TABLE 3-continued

Compilation of synthesized end compounds

| Example No. | Chemical Name/Structure/Remarks | Prepared in analogy to Procedure | Characterization |
|---|---|---|---|
| 19 | endo-(4-Amino-5-chloro-2-methoxy-phenyl)-[3-(4-fluoro-phenyl)-8-aza-bicyclo[3.2.1]oct-8-yl]-methanone | A | Mass spectrum (ESI+): m/z = 389/391 (Cl) [M + H]+ |
| 20 | endo-[3-(4-Fluoro-phenyl)-8-aza-bicyclo[3.2.1]oct-8-yl]-(1-methanesulfonyl-2,3-dihydro-1H-indol-5-yl)-methanone | A | Mass spectrum (ESI+): m/z = 429 [M + H]+ |
| 21 | endo-[3-(4-Fluoro-phenyl)-8-aza-bicyclo[3.2.1]oct-8-yl]-pyridin-4-yl-methanone | A | Mass spectrum (ESI+): m/z = 311 [M + H]+ |
| 22 | endo-[3-(4-Fluoro-phenyl)-8-aza-bicyclo[3.2.1]oct-8-yl]-(4-methyl-thiazol-5-yl)-methanone | A | Mass spectrum (ESI+): m/z = 331 [M + H]+ |
| 23 | endo-[3-(4-Fluoro-phenyl)-8-aza-bicyclo[3.2.1]oct-8-yl]-(4,5,6,7-tetrahydro-1H-indazol-3-yl)-methanone | A | Mass spectrum (ESI+): m/z = 354 [M + H]+ |
| 24 | endo-[3-(4-Fluoro-phenyl)-8-aza-bicyclo[3.2.1]oct-8-yl]-(4-methyl-[1,2,3]thiadiazol-5-yl)-methanone | A | Mass spectrum (ESI+): m/z = 332 [M + H]+ |

TABLE 3-continued

Compilation of synthesized end compounds

| Example No. | Chemical Name/Structure/Remarks | Prepared in analogy to Procedure | Characterization |
|---|---|---|---|
| 25 | endo-[3-(4-Fluoro-phenyl)-8-aza-bicyclo[3.2.1]oct-8-yl]-[3-(1H-tetrazol-5-yl)-phenyl]-methanone | A | Mass spectrum (ESI+): m/z = 378 [M + H]+ |
| 26 | endo-[3-(4-Fluoro-phenyl)-8-aza-bicyclo[3.2.1]oct-8-yl]-(5-hydroxy-pyridin-3-yl)-methanone | A | Mass spectrum (ESI+): m/z = 327 [M + H]+ |
| 27 | endo-(4,7-Dimethoxy-1H-indol-2-yl)-[3-(4-fluoro-phenyl)-8-aza-bicyclo[3.2.1]oct-8-yl]-methanone | A | Mass spectrum (ESI+): m/z = 409 [M + H]+ |
| 28 | endo-5-[3-(4-Fluoro-phenyl)-8-aza-bicyclo[3.2.1]octane-8-carbonyl]-1-(2-methoxy-ethyl)-1,3-dihydro-benzoimidazol-2-one | A | Mass spectrum (ESI+): m/z = 424 [M + H]+ |
| 29 | endo-7-[3-(4-Fluoro-phenyl)-8-aza-bicyclo[3.2.1]octane-8-carbonyl]-2-isobutyl-2,3-dihydro-isoindol-1-one | A | Mass spectrum (ESI+): m/z = 421 [M + H]+ |

TABLE 3-continued

Compilation of synthesized end compounds

| Example No. | Chemical Name/Structure/Remarks | Prepared in analogy to Procedure | Characterization |
|---|---|---|---|
| 30 | endo-(4,5-Dichloro-isothiazol-3-yl)-[3-(4-fluoro-phenyl)-8-aza-bicyclo[3.2.1]oct-8-yl]-methanone | A | Mass spectrum (ESI$^+$): 385/387/389 (2Cl) [M + H]$^+$ |
| 31 | endo-[3-(4-Fluoro-phenyl)-8-aza-bicyclo[3.2.1]oct-8-yl]-[4-(thietan-3-yloxy)-phenyl]-methanone | A | Mass spectrum (ESI$^+$): m/z = 398 [M + H]$^+$ |
| 32 | endo-[4-(Thietan-3-yloxy)-phenyl]-(3-p-tolyl-8-aza-bicyclo[3.2.1]oct-8-yl)-methanone | A | Mass spectrum (ESI+): m/z = 394 [M + H]$^+$ |
| 33 | endo-[3-(4-Fluoro-phenyl)-8-aza-bicyclo[3.2.1]oct-8-yl]-isoquinolin-1-yl-methanone | A | Mass spectrum (ESI$^+$): m/z = 361 [M + H]$^+$ |
| 34 | endo-[3-(4-Fluoro-phenyl)-8-aza-bicyclo[3.2.1]oct-8-yl]-furan-2-yl-methanone | A | Mass spectrum (ESI$^+$): m/z = 300 [M + H]$^+$ |
| 35 | endo-[3-(4-Fluoro-phenyl)-8-aza-bicyclo[3.2.1]oct-8-yl]-pyrazolo[1,5-a]pyrimidin-3-yl-methanone | A | Mass spectrum (ESI$^+$): m/z = 351 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 36 | endo-3-Fluoro-4-[3-(4-fluoro-phenyl)-8-aza-bicyclo[3.2.1]octane-8-carbonyl]-benzamide | A | Mass spectrum (ESI$^+$): m/z = 371 [M + H]$^+$ |
| 37 | endo-[3-(4-Fluoro-phenyl)-8-aza-bicyclo[3.2.1]oct-8-yl]-quinolin-5-yl-methanone | A | Mass spectrum (ESI$^+$): m/z = 361 [M + H]$^+$ |
| 38 | endo-(1-Ethyl-5-methyl-1H-pyrazol-4-yl)-(3-p-tolyl-8-aza-bicyclo[3.2.1]oct-8-yl)-methanone | A | Mass spectrum (ESI$^+$): m/z = 338 [M + H]$^+$ |
| 39 | endo-5-[3-(4-Fluoro-phenyl)-8-aza-bicyclo[3.2.1]octane-8-carbonyl]-1,3-dimethyl-1,3-dihydro-benzoimidazol-2-one | A | Mass spectrum (ESI$^+$): m/z = 394 [M + H]$^+$ |
| 40 | endo-[3-(1,1-Dioxo-1lambda*6*-[1,2]thiazinan-2-yl)-phenyl-[3-(4-fluoro-phenyl)-8-aza-bicyclo[3.2.1]oct-8-yl]-methanone | A | Mass spectrum (ESI$^+$): m/z = 443 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 41 | endo-[4-(3,5-Dimethyl-pyrazol-1-yl)-phenyl]-[3-(4-fluoro-phenyl)-8-aza-bicyclo[3.2.1]oct-8-yl]-methanone | A | Mass spectrum (ESI$^+$): m/z = 404 [M + H]$^+$ |
| 42 | endo-[3-(4-Fluoro-phenyl)-8-aza-bicyclo[3.2.1]oct-8-yl]-(5-methyl-7-trifluoromethyl-pyrazolo[1,5-a]pyrimidin-2-yl)-methanone | A | Mass spectrum (ESI$^+$): m/z = 433 [M + H]$^+$ |
| 43 | endo-[3-(4-Fluoro-phenyl)-8-aza-bicyclo[3.2.1]oct-8-yl]-thiazol-4-yl-methanone | A | Mass spectrum (ESI$^+$): m/z = 317 [M + H]$^+$ |
| 44 | endo-[3-(4-Fluoro-phenyl)-8-aza-bicyclo[3.2.1]oct-8-yl]-(3,4,5-trimethoxy-phenyl)-methanone | A | Mass spectrum (ESI$^+$): m/z = 400 [M + H]$^+$ |
| 45 | endo-(3-tert-Butoxy-phenyl)-[3-(4-fluoro-phenyl)-8-aza-bicyclo[3.2.1]oct-8-yl]-methanone | A | LC (method 4): t$_R$ = 2.74 min; MS (ESI$^+$): m/z = 382 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 46 | endo-6-[3-(4-Fluoro-phenyl)-8-aza-bicyclo[3.2.1]octane-8-carbonyl]-1,3-dihydro-indol-2-one | A | LC (method 4): $t_R$ = 2.24 min; MS (ESI$^+$): m/z = 365 [M + H]$^+$ |
| 47 | endo-5-[3-(4-Fluoro-phenyl)-8-aza-bicyclo[3.2.1]octane-8-carbonyl]-1,3-dihydro-indol-2-one | A | LC (method 4): $t_R$ = 2.22 min; MS (ESI$^+$): m/z = 365 [M + H]$^+$ |
| 48 | endo-(2-Amino-1H-benzoimidazol-5-yl)-[3-(4-fluoro-phenyl)-8-aza-bicyclo[3.2.1]oct-8-yl]-methanone<br><br>is isolated as its trifluoroacetic acid salt | A | LC (method 4): $t_R$ = 1.86 min; MS (ESI$^+$): m/z = 365 [M + H]$^+$ |
| 49 | endo-(4-tert-Butoxy-phenyl)-[3-(4-fluoro-phenyl)-8-aza-bicyclo[3.2.1]oct-8-yl]-methanone | A | LC (method 4): $t_R$ = 2.86 min; MS (ESI$^+$): m/z = 382 [M + H]$^+$ |
| 50 | endo-[3-(4-Fluoro-phenyl)-8-aza-bicyclo[3.2.1]oct-8-yl]-(2-methyl-1H-indol-5-yl)-methanone | A | LC (method 4): $t_R$ = 2.86 min; MS (ESI$^+$): m/z = 363 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 51 | endo-(1-Ethyl-1H-indol-6-yl)-[3-(4-fluoro-phenyl)-8-aza-bicyclo[3.2.1]oct-8-yl]-methanone<br><br>is isolated as its trifluoroacetic acid salt | A | LC (method 4):<br>$t_R$ = 2.67 min;<br>MS (ESI$^+$):<br>m/z = 377<br>[M + H]$^+$ |
| 52 | endo-(2,3-Dimethyl-1H-indol-6-yl)-[3-(4-fluoro-phenyl)-8-aza-bicyclo[3.2.1]oct-8-yl]-methanone<br><br>is isolated as its trifluoroacetic acid salt | A | LC (method 4):<br>$t_R$ = 2.67 min;<br>MS (ESI$^+$):<br>m/z = 377<br>[M + H]$^+$ |
| 53 | endo-[3-(4-Fluoro-phenyl)-8-aza-bicyclo[3.2.1]oct-8-yl]-(1-methyl-1H-indol-6-yl)-methanone<br><br>is isolated as its trifluoroacetic acid salt | A | LC (method 4):<br>$t_R$ = 2.61 min;<br>MS (ESI$^+$):<br>m/z = 363<br>[M + H]$^+$ |
| 54 | endo-[3-(4-Fluoro-phenyl)-8-aza-bicyclo[3.2.1]oct-8-yl]-(1,2,3,4-tetrahydro-quinolin-6-yl)-methanone<br><br>is isolated as its trifluoroacetic acid salt | A | LC (method 4):<br>$t_R$ = 2.20 min;<br>MS (ESI$^+$):<br>m/z = 365<br>[M + H]$^+$ |
| 55 | endo-[3-(4-Fluoro-phenyl)-8-aza-bicyclo[3.2.1]oct-8-yl]-(3-hydroxy-4-methyl-phenyl)-methanone | A | LC (method 3):<br>$t_R$ = 2.36 min;<br>MS (ESI$^+$):<br>m/z = 340<br>[M + H]$^+$ |

TABLE 3-continued

Compilation of synthesized end compounds

| Example No. | Chemical Name/Structure/Remarks | Prepared in analogy to Procedure | Characterization |
|---|---|---|---|
| 56 | endo-N-{2-[3-(4-Fluoro-phenyl)-8-aza-bicyclo[3.2.1]octane-8-carbonyl]-phenyl}-acetamide | A | LC (method 3): $t_R$ = 1.73 min; MS (ESI$^+$): m/z = 367 [M + H]$^+$ |
| 57 | endo-(2-Fluoro-phenyl)-[3-(4-fluoro-phenyl)-8-aza-bicyclo[3.2.1]oct-8-yl]-methanone | A | LC (method 3): $t_R$ = 2.49 min; MS (ESI$^+$): m/z = 328 [M + H]$^+$ |
| 58 | endo-1-{4-[3-(4-Fluoro-phenyl)-8-aza-bicyclo[3.2.1]octane-8-carbonyl]-phenyl}-propan-2-one | A | LC (method 3): $t_R$ = 2.32 min; MS (ESI$^+$): m/z = 366 [M + H]$^+$ |
| 59 | endo-5-[3-(4-Fluoro-phenyl)-8-aza-bicyclo[3.2.1]octane-8-carbonyl]-1-methyl-1,3-dihydro-benzoimidazol-2-one | A | LC (method 3): $t_R$ = 2.08 min; MS (ESI$^+$): m/z = 380 [M + H]$^+$ |
| 60 | endo-1-{3-[3-(4-Fluoro-phenyl)-8-aza-bicyclo[3.2.1]octane-8-carbonyl]-phenyl}-imidazolidin-2-one | A | LC (method 3): $t_R$ = 2.15 min; MS (ESI$^+$): m/z = 394 [M + H]$^+$ |
| 61 | endo-3-[3-(4-Fluoro-phenyl)-8-aza-bicyclo[3.2.1]octane-8-carbonyl]-benzoic acid methyl ester | A | LC (method 3): $t_R$ = 2.47 min; MS (ESI$^+$): m/z = 368 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 62 | endo-[3-(4-Fluoro-phenyl)-8-aza-bicyclo[3.2.1]oct-8-yl]-(1H-indol-6-yl)-methanone<br />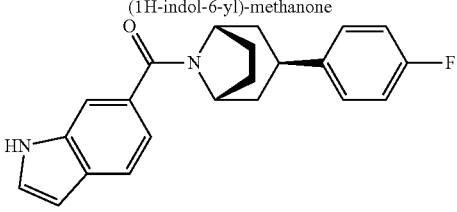<br />is isolated as its trifluoroacetic acid salt | A | LC (method 3):<br />$t_R$ = 2.40 min;<br />MS (ESI$^+$):<br />m/z = 349<br />[M + H]$^+$ |
| 63 | endo-2-[3-(4-Fluoro-phenyl)-8-aza-bicyclo[3.2.1]octane-8-carbonyl]-benzonitrile<br />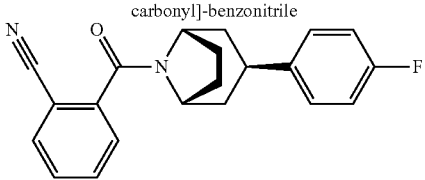 | A | LC (method 3):<br />$t_R$ = 2.39 min;<br />MS (ESI$^+$):<br />m/z = 335<br />[M + H]$^+$ |
| 64 | endo-N-{3-[3-(4-Fluoro-phenyl)-8-aza-bicyclo[3.2.1]octane-8-carbonyl]-phenyl}-acetamide<br />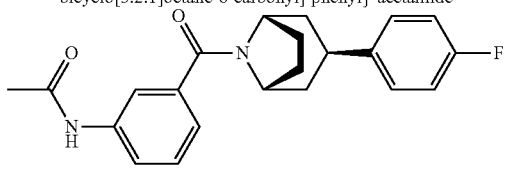 | A | LC (method 3):<br />$t_R$ = 2.18 min;<br />MS (ESI$^+$):<br />m/z = 367<br />[M + H]$^+$ |
| 65 | endo-1-{4-[3-(4-Fluoro-phenyl)-8-aza-bicyclo[3.2.1]octane-8-carbonyl]-phenyl}-pyrrolidin-2-one<br />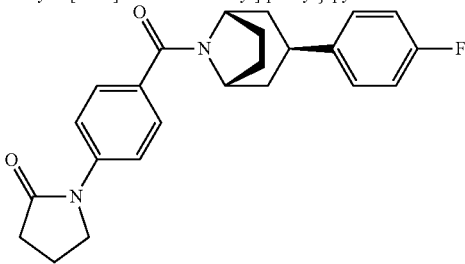 | A | LC (method 3):<br />$t_R$ = 2.27 min;<br />MS (ESI$^+$):<br />m/z = 393<br />[M + H]$^+$ |
| 66 | endo-[3-(4-Fluoro-phenyl)-8-aza-bicyclo[3.2.1]oct-8-yl]-(1-methyl-1H-benzoimidazol-5-yl)-methanone<br />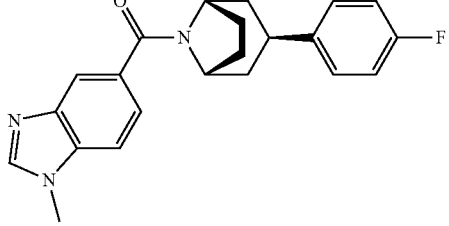<br />is isolated as its trifluoroacetic acid salt | A | LC (method 3):<br />$t_R$ = 1.70 min;<br />MS (ESI$^+$):<br />m/z = 364<br />[M + H]$^+$ |

TABLE 3-continued

Compilation of synthesized end compounds

| Example No. | Chemical Name/Structure/Remarks | Prepared in analogy to Procedure | Characterization |
|---|---|---|---|
| 67 | Endo-[3-(4-Fluoro-phenyl)-8-aza-bicyclo[3.2.1]oct-8-yl]-(3-methanesulfonyl-phenyl)-methanone | A | LC (method 3): $t_R$ = 2.23 min; MS (ESI$^+$): m/z = 388 [M + H]$^+$ |
| 68 | endo-[3-(4-Fluoro-phenyl)-8-aza-bicyclo[3.2.1]oct-8-yl]-(1-methyl-1H-benzotriazol-5-yl)-methanone<br><br>is isolated as its trifluoroacetic acid salt | A | LC (method 3): $t_R$ = 2.21 min; MS (ESI$^+$): m/z = 365 [M + H]$^+$ |
| 69 | endo-7-[3-(4-Fluoro-phenyl)-8-aza-bicyclo[3.2.1]octane-8-carbonyl]-2-methyl-3H-quinazolin-4-one<br><br>is isolated as its trifluoroacetic acid salt | A | LC (method 3): $t_R$ = 1.85 min; MS (ESI$^+$): m/z = 392 [M + H]$^+$ |
| 70 | endo-[3-(4-Fluoro-phenyl)-8-aza-bicyclo[3.2.1]oct-8-yl]-quinoxalin-6-yl-methanone<br><br>is isolated as its trifluoroacetic acid salt | A | LC (method 3): $t_R$ = 2.27 min; MS (ESI$^+$): m/z = 362 [M + H]$^+$ |
| 71 | endo-N-{4-[3-(4-Fluoro-phenyl)-8-aza-bicyclo[3.2.1]octane-8-carbonyl]-benzyl}-acetamide | A | LC (method 3): $t_R$ = 2.07 min; MS (ESI$^+$): m/z = 381 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 72 | endo-1-{2-[3-(4-Fluoro-phenyl)-8-aza-bicyclo[3.2.1]octane-8-carbonyl]-phenyl}-pyrrolidin-2-one | A | LC (method 3): $t_R$ = 2.20 min; MS (ESI$^+$): m/z = 393 [M + H]$^+$ |
| 73 | endo-(1H-Benzoimidazol-4-yl)-[3-(4-fluoro-phenyl)-8-aza-bicyclo[3.2.1]oct-8-yl]-methanone | A | LC (method 3): $t_R$ = 1.72 min; MS (ESI$^+$): m/z = 350 [M + H]$^+$ |
| 74 | is isolated as its trifluoroacetic acid salt<br>endo-[3-(4-Fluoro-phenyl)-8-aza-bicyclo[3.2.1]oct-8-yl]-(2-methyl-3H-benzoimidazol-5-yl)-methanone | A | LC (method 3): tR = 1.71 min; MS (ESI$^+$): m/z = 364 [M + H]$^+$ |
| 75 | is isolated as its trifluoroacetic acid salt<br>endo-1-{3-[3-(4-Fluoro-phenyl)-8-aza-bicyclo[3.2.1]octane-8-carbonyl]-phenyl}-pyrrolidin-2-one | A | LC (method 3): $t_R$ = 2.28 min; MS (ESI+): m/z = 393 [M + H]+ |
| 76 | endo-(2,2-Difluoro-benzo[1,3]dioxol-5-yl)-[3-(4-fluoro-phenyl)-8-aza-bicyclo[3.2.1]oct-8-yl]-methanone | A | LC (method 3): $t_R$ = 2.62 min; MS (ESI$^+$): m/z = 390 [M + H]$^+$ |
| 77 | endo-(3,4-Difluoro-phenyl)-[3-(4-fluoro-phenyl)-8-aza-bicyclo[3.2.1]oct-8-yl]methanone | A | LC (method 3): $t_R$ = 2.52 min; MS (ESI$^+$): m/z = 346 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 78 | endo-5-3-(4-Fluoro-phenyl)-8-aza-bicyclo[3.2.1]octane-8-carbonyl]-1-methyl-1,3-dihydro-indol-2-one | A | LC (method 3): $t_R$ = 2.20 min; MS (ESI$^+$): m/z = 379 [M + H]$^+$ |
| 79 | endo-4-[3-(4-Fluoro-phenyl)-8-aza-bicyclo[3.2.1]octane-8-carbonyl]N-methyl-benzamide | A | LC (method 3): $t_R$ = 2.09 min; MS (ESI$^+$): m/z = 367 [M + H]$^+$ |
| 80 | endo-3-[3-(4-Fluoro-phenyl)-8-aza-bicyclo[3.2.1]octane-8-carbonyl]-N-methyl-benzamide | A | LC (method 3): $t_R$ = 2.11 min; MS (ESI$^+$): m/z = 367 [M + H]$^+$ |
| 81 | endo-4-[3-(4-Fluoro-phenyl)-8-aza-bicyclo[3.2.1]octane-8-carbonyl]-benzamide | A | LC (method 3): $t_R$ = 2.01 min; MS (ESI$^+$): m/z = 353 [M + H]$^+$ |
| 82 | endo-[3-(4-Fluoro-phenyl)-8-aza-bicyclo[3.2.1]oct-8-yl]-(3-hydroxymethyl-phenyl)-methanone | A | LC (method 3): $t_R$ = 2.16 min; MS (ESI$^+$): m/z = 340 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 83 | endo-[3-(4-Fluoro-phenyl)-8-aza-bicyclo[3.2.1]oct-8-yl]-(3-methylamino-phenyl)-methanone<br><br>is isolated as its trifluoroacetic acid salt | A | LC (method 3): $t_R$ = 1.89 min; MS (ESI$^+$): m/z = 393 [M + H]$^+$ |
| 84 | endo-3-[3-(4-Fluoro-phenyl)-8-aza-bicyclo[3.2.1]octane-8-carbonyl]-benzamide | A | LC (method 3): $t_R$ = 2.03 min; MS (ESI$^+$): m/z = 353 [M + H]$^+$ |
| 85 | endo-[3-(4-Fluoro-phenyl)-8-aza-bicyclo[3.2.1]oct-8-yl]-[4-(1H-tetrazol-5-yl)-phenyl]-methanone<br><br>is isolated as its trifluoroacetic acid salt | A | LC (method 3): $t_R$ = 2.15 min; MS (ESI$^+$): m/z = 378 [M + H]$^+$ |
| 86 | endo-[3-(4-Fluoro-phenyl)-8-aza-bicyclo[3.2.1]oct-8-yl]-[3-(1H-tetrazol-5-yl)-phenyl]-methanone<br><br>was isolated as its trifluoroacetic acid salt | A | LC (method 3): $t_R$ = 2.18 min; MS (ESI$^+$): m/z = 378 [M + H]$^+$ |
| 87 | endo-[3-(4-Fluoro-phenyl)-8-aza-bicyclo[3.2.1]oct-8-yl]-(4-oxazol-5-yl-phenyl)-methanone<br><br>was isolated as its trifluoroacetic acid salt | A | LC (method 3): $t_R$ = 2.36 min; MS (ESI$^+$): m/z = 377 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 88 | endo-[3-(4-Fluoro-phenyl)-8-aza-bicyclo[3.2.1]oct-8-yl]-[3-(5-methyl-[1,2,4]oxadiazol-3-yl)-phenyl]-methanone<br><br>was isolated as its trifluoroacetic acid salt | A | LC (method 3):<br>$t_R$ = 2.50 min;<br>MS (ESI$^+$):<br>m/z = 392<br>[M + H]$^+$ |
| 89 | endo-[3-(4-Fluoro-phenyl)-8-aza-bicyclo[3.2.1]oct-8-yl]-[4-(5-methyl-[1,2,4]oxadiazol-3-yl)-phenyl]-methanone<br><br>was isolated as its trifluoroacetic acid salt | A | LC (method 3):<br>$t_R$ = 2.48 min;<br>MS (ESI$^+$):<br>m/z = 392<br>[M + H]$^+$ |
| 90 | endo-[3-(4-Fluoro-phenyl)-8-aza-bicyclo[3.2.1]oct-8-yl]-[3-(1H-pyrazol-3-yl)-phenyl]-methanone<br><br>was isolated as its trifluoroacetic acid salt | A | LC (method 3):<br>$t_R$ = 2.24 min;<br>MS (ESI$^+$):<br>m/z = 376<br>[M + H]$^+$ |
| 91 | endo-[3-(4-Fluoro-phenyl)-8-aza-bicyclo[3.2.1]oct-8-yl]-(3-oxazol-5-yl-phenyl)-methanone<br><br>was isolated as its trifluoroacetic acid salt | A | LC (method 3):<br>$t_R$ = 2.37 min;<br>MS (ESI$^+$):<br>m/z = 377<br>[M + H]$^+$ |
| 92 | endo-[3-(4-Fluoro-phenyl)-8-aza-bicyclo[3.2.1]oct-8-yl]-(6-hydroxy-pyridin-2-yl)-methanone<br><br>was isolated as its trifluoroacetic acid salt | A | LC (method 3):<br>$t_R$ = 1.98 min;<br>MS (ESI$^+$):<br>m/z = 327<br>[M + H]$^+$ |

TABLE 3-continued

Compilation of synthesized end compounds

| Example No. | Chemical Name/Structure/Remarks | Prepared in analogy to Procedure | Characterization |
|---|---|---|---|
| 93 | endo-Benzothiazol-5-yl-[3-(4-fluoro-phenyl)-8-aza-bicyclo[3.2.1]oct-8-yl]-methanone<br><br>was isolated as its trifluoroacetic acid salt | A | LC (method 3):<br>$t_R$ = 2.36 min;<br>MS (ESI$^+$):<br>m/z = 367<br>[M + H]$^+$ |
| 94 | endo-Benzothiazol-6-yl-[3-(4-fluoro-phenyl)-8-aza-bicyclo[3.2.1]oct-8-yl]-methanone | A | LC (method 3):<br>$t_R$ = 2.35 min;<br>MS (ESI$^+$):<br>m/z = 367<br>[M + H]$^+$ |
| 95 | endo-7-[3-(4-Fluoro-phenyl)-8-aza-bicyclo[3.2.1]octane-8-carbonyl]-2,3-dihydro-isoindol-1-one | A | LC (method 3):<br>$t_R$ = 2.05 min;<br>MS (ESI$^+$):<br>m/z = 365<br>[M + H]$^+$ |
| 96 | endo-[3-(4-Fluoro-phenyl)-8-aza-bicyclo[3.2.1]oct-8-yl]-phenyl-methanone | A | LC (method 3):<br>$t_R$ = 2.48 min;<br>MS (ESI$^+$):<br>m/z = 310<br>[M + H]$^+$ |
| 97 | endo-[3-(4-Fluoro-phenyl)-8-aza-bicyclo[3.2.1]oct-8-yl]-pyridin-3-yl-methanone<br><br>was isolated as its trifluoroacetic acid salt | A | LC (method 3):<br>$t_R$ = 1.78 min;<br>MS (ESI$^+$):<br>m/z = 311<br>[M + H]$^+$ |
| 98 | endo-[3-(4-Fluoro-phenyl)-8-aza-bicyclo[3.2.1]oct-8-yl]-pyridin-2-yl-methanone<br><br>was isolated as its trifluoroacetic acid salt | A | LC (method 3):<br>$t_R$ = 2.22 min;<br>MS (ESI$^+$):<br>m/z = 311<br>[M + H]$^+$ |

TABLE 3-continued

Compilation of synthesized end compounds

| Example No. | Chemical Name/Structure/Remarks | Prepared in analogy to Procedure | Characterization |
|---|---|---|---|
| 99 | endo-[3-(4-Fluoro-phenyl)-8-aza-bicyclo[3.2.1]oct-8-yl]-m-tolyl-methanone | A | LC (method 3): $t_R$ = 2.58 min; MS (ESI$^+$): m/z = 324 [M + H]$^+$ |
| 100 | endo-[3-(4-Fluoro-phenyl)-8-aza-bicyclo[3.2.1]oct-8-yl]-o-tolyl-methanone | A | LC (method 3): $t_R$ = 2.54 min; MS (ESI$^+$): m/z = 324 [M + H]$^+$ |
| 101 | endo-[3-(4-Fluoro-phenyl)-8-aza-bicyclo[3.2.1]oct-8-yl]-p-tolyl-methanone | A | LC (method 3): $t_R$ = 2.58 min; MS (ESI$^+$): m/z = 324 [M + H]$^+$ |
| 102 | endo-[3-(4-Fluoro-phenyl)-8-aza-bicyclo[3.2.1]oct-8-yl]-(6-hydroxy-pyridin-3-yl)-methanone | A | LC (method 3): $t_R$ = 1.91 min; MS (ESI$^+$): m/z = 327 [M + H]$^+$ |
| 103 | was isolated as its trifluoroacetic acid salt endo-(4-Fluoro-phenyl)-[3-(4-fluoro-phenyl)-8-aza-bicyclo[3.2.1]oct-8-yl]-methanone | A | LC (method 3): $t_R$ = 2.51 min; MS (ESI$^+$): m/z = 328 [M + H]$^+$ |
| 104 | endo-(3-Fluoro-phenyl)-[3-(4-fluoro-phenyl)-8-aza-bicyclo[3.2.1]oct-8-yl]-methanone | A | LC (method 3): $t_R$ = 2.52 min; MS (ESI$^+$): m/z = 328 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 105 | endo-4-[3-(4-Fluoro-phenyl)-8-aza-bicyclo[3.2.1]octane-8-carbonyl]-benzonitrile | A | LC (method 3): $t_R$ = 2.40 min; MS (ESI$^+$): m/z = 335 [M + H]$^+$ |
| 106 | endo-3-[3-(4-Fluoro-phenyl)-8-aza-bicyclo[3.2.1]octane-8-carbonyl]-benzonitrile | A | LC (method 3): $t_R$ = 2.41 min; MS (ESI$^+$): m/z = 335 [M + H]$^+$ |
| 107 | endo-(3,4-Dimethyl-phenyl)-[3-(4-fluoro-phenyl)-8-aza-bicyclo[3.2.1]oct-8-yl]-methanone | A | LC (method 3): $t_R$ = 2.66 min; MS (ESI$^+$): m/z = 338 [M + H]$^+$ |
| 108 | endo-[3-(4-Fluoro-phenyl)-8-aza-bicyclo[3.2.1]oct-8-yl]-(4-methoxy-phenyl)-methanone | A | LC (method 3): $t_R$ = 2.47 min; MS (ESI$^+$): m/z = 340 [M + H]$^+$ |
| 109 | endo-[3-(4-Fluoro-phenyl)-8-aza-bicyclo[3.2.1]oct-8-yl]-(3-methoxy-phenyl)-methanone | A | LC (method 3): $t_R$ = 2.48 min; MS (ESI$^+$): m/z = 340 [M + H]$^+$ |
| 110 | endo-[3-(4-Fluoro-phenyl)-8-aza-bicyclo[3.2.1]oct-8-yl]-(2-methoxy-phenyl)-methanone | A | LC (method 3): $t_R$ = 2.45 min; MS (ESI$^+$): m/z = 340 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 111 | endo-(2-Chloro-phenyl)-[3-(4-fluoro-phenyl)-8-aza-bicyclo[3.2.1]oct-8-yl]-methanone 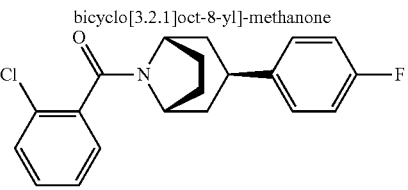 | A | LC (method 3): $t_R$ = 2.55 min; MS (ESI$^+$): m/z = 344/346 (Cl) [M + H]$^+$ |
| 112 | endo-(4-Chloro-phenyl)-[3-(4-fluoro-phenyl)-8-aza-bicyclo[3.2.1]oct-8-yl]-methanone 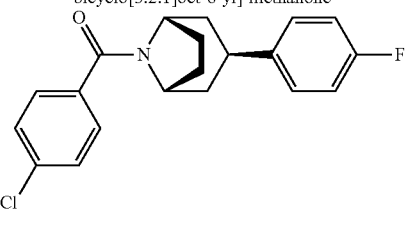 | A | LC (method 3): $t_R$ = 2.62 min; MS (ESI$^+$): m/z = 344/346 (Cl) [M + H]$^+$ |
| 113 | endo-[3-(4-Fluoro-phenyl)-8-aza-bicyclo[3.2.1]oct-8-yl]-(1H-indol-5-yl)-methanone 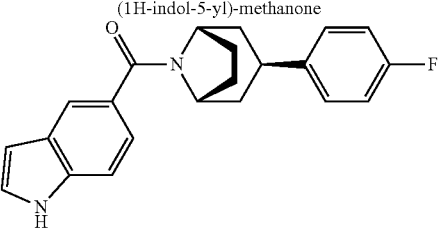 was isolated as its trifluoroacetic acid salt | A | LC (method 3): tR = 2.36 min; MS (ESI$^+$): m/z = 349 [M + H]$^+$ |
| 114 | endo-Benzo[1,3]dioxol-5-yl-[3-(4-fluoro-phenyl)-8-aza-bicyclo[3.2.1]oct-8-yl]-methanone 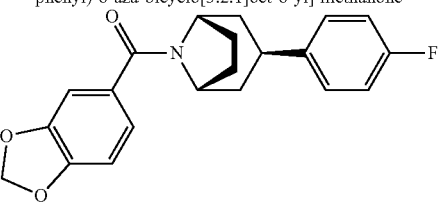 | A | LC (method 3): $t_R$ = 2.44 min; MS (ESI$^+$): m/z = 354 [M + H]$^+$ |
| 115 | endo-N-{4-[3-(4-Fluoro-phenyl)-8-aza-bicyclo[3.2.1]octane-8-carbonyl]-phenyl}-acetamide 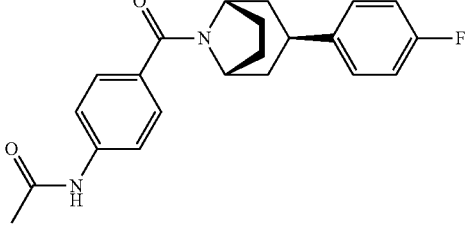 | A | LC (method 3): $t_R$ = 2.16 min; MS (ESI$^+$): m/z = 367 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 116 | endo-4-[3-(4-Fluoro-phenyl)-8-aza-bicyclo[3.2.1]octane-8-carbonyl]-benzoic acid methyl ester | A | LC (method 3): $t_R$ = 2.47 min; MS (ESI$^+$): m/z = 368 [M + H]$^+$ |
| 117 | endo-(2,4-Dimethoxy-phenyl)-[3-(4-fluoro-phenyl)-8-aza-bicyclo[3.2.1]oct-8-yl]-methanone | A | LC (method 3): $t_R$ = 2.45 min; MS (ESI$^+$): m/z = 370 [M + H]$^+$ |
| 118 | endo-(3,4-Dimethoxy-phenyl)-[3-(4-fluoro-phenyl)-8-aza-bicyclo[3.2.1]oct-8-yl]-methanone | A | LC (method 3): $t_R$ = 2.39 min; MS (ESI$^+$): m/z = 370 [M + H]$^+$ |
| 119 | endo-4-[3-(4-Fluoro-phenyl)-8-aza-bicyclo[3.2.1]octane-8-carbonyl]-benzenesulfonamide | A | LC (method 3): $t_R$ = 2.13 min; MS (ESI$^+$): m/z = 389 [M + H]$^+$ |
| 120 | endo-(3H-Benzotriazol-5-yl)-[3-(4-fluoro-phenyl)-8-aza-bicyclo[3.2.1]oct-8-yl]-methanone | A | LC (method 3): $t_R$ = 2.12 min; MS (ESI$^+$): m/z = 351 [M + H]$^+$ | was isolated as its trifluoroacetic acid salt

TABLE 3-continued

Compilation of synthesized end compounds

| Example No. | Chemical Name/Structure/Remarks | Prepared in analogy to Procedure | Characterization |
|---|---|---|---|
| 121 | endo-[3-(4-Fluoro-phenyl)-8-aza-bicyclo[3.2.1]oct-8-yl]-(4-hydroxymethyl-phenyl)-methanone | A | LC (method 3): $t_R$ = 2.16 min; MS (ESI$^+$): m/z = 340 [M + H]$^+$ |
| 122 | endo-(2,4-Dimethyl-phenyl)-[3-(4-fluoro-phenyl)-8-aza-bicyclo[3.2.1]oct-8-yl]-methanone | A | LC (method 3): $t_R$ = 2.67 min; MS (ESI$^+$): m/z = 338 [M + H]$^+$ |
| 123 | endo-(3,5-Dimethoxy-phenyl)-[3-(4-fluoro-phenyl)-8-aza-bicyclo[3.2.1]oct-8-yl]-methanone | A | LC (method 3): $t_R$ = 2.51 min; MS (ESI$^+$): m/z = 370 [M + H]$^+$ |
| 124 | endo-1-{3-[3-(4-Fluoro-phenyl)-8-aza-bicyclo[3.2.1]octane-8-carbonyl]-phenyl}-ethanone | A | LC (method 3): $t_R$ = 2.40 min; MS (ESI$^+$): m/z = 352 [M + H]$^+$ |
| 125 | endo-(3-Chloro-phenyl)-[3-(4-fluoro-phenyl)-8-aza-bicyclo[3.2.1]oct-8-yl]-methanone | A | Mass spectrum (ESI$^+$): m/z = 344/346 (Cl) [M + H]$^+$ |
| 126 | endo-1-{2-[3-(4-Fluoro-phenyl)-8-aza-bicyclo[3.2.1]octane-8-carbonyl]-phenyl}-ethanone | A | Mass spectrum (ESI$^+$): m/z = 352 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 127 | endo-(2,3-Dimethoxy-phenyl)-[3-(4-fluoro-phenyl)-8-aza-bicyclo[3.2.1]oct-8-yl]-methanone | A | Mass spectrum (ESI+): m/z = 370 [M + H]+ |
| 128 | endo-1-{4-[3-(4-Fluoro-phenyl)-8-aza-bicyclo[3.2.1]octane-8-carbonyl]-phenyl}-ethanone | A | Mass spectrum (ESI+): m/z = 352 [M + H]+ |
| 129 | endo-[3-(4-Fluoro-phenyl)-8-aza-bicyclo[3.2.1]oct-8-yl]-(3-hydroxy-phenyl)-methanone | A | LC (method 4): $t_R$ = 2.37 min; MS (ESI+): m/z = 326 [M + H]+ |
| 130 | endo-[3-(4-Fluoro-phenyl)-8-aza-bicyclo[3.2.1]oct-8-yl]-(4-hydroxy-phenyl)-methanone | A | LC (method 4): $t_R$ = 2.34 min; MS (ESI+): m/z = 326 [M + H]+ |
| 131 | endo-[3-(4-Fluoro-phenyl)-8-aza-bicyclo[3.2.1]oct-8-yl]-(1-methyl-1H-indol-5-yl)-methanone | A | LC (method 4): $t_R$ = 2.65 min; MS (ESI+): m/z = 363 [M + H]+ |
| 132 | endo-(2,3-Dimethyl-1H-indol-5-yl)-[3-(4-fluoro-phenyl)-8-aza-bicyclo[3.2.1]oct-8-yl]-methanone | A | LC (method 4): $t_R$ = 2.68 min; MS (ESI+): m/z = 377 [M + H]+ |

TABLE 3-continued

Compilation of synthesized end compounds

| Example No. | Chemical Name/Structure/Remarks | Prepared in analogy to Procedure | Characterization |
|---|---|---|---|
| 133 | (2,3-Dihydro-benzo[1,4]dioxin-6-yl)-(3-phenyl-8-aza-bicyclo[3.2.1]oct-8-yl)-methanone<br>1:1 mixture of endo and exo isomer | B | Mass spectrum (ESI$^+$): m/z = 350 [M + H]$^+$ |
| 134 | endo-(2,3-Dihydro-benzo[1,4]dioxin-6-yl)-[3-(4-methoxy-phenyl)-8-aza-bicyclo[3.2.1]oct-8-yl]-methanone | A or B | Mass spectrum (ESI$^+$): m/z = 380 [M + H]$^+$ |
| 135 | using procedure B requires separation from the exo isomer by HPLC on chiral phase<br>exo-(2,3-Dihydro-benzo[1,4]dioxin-6-yl)-[3-(4-methoxy-phenyl)-8-aza-bicyclo[3.2.1]oct-8-yl]-methanone<br>was separated from the endo isomer by HPLC on chiral phase | B | Mass spectrum (ESI$^+$): m/z = 380 [M + H]$^+$ |
| 136 | endo-(2,3-Dihydro-benzo[1,4]dioxin-6-yl)-[3-(4-isopropyl-phenyl)-8-aza-bicyclo[3.2.1]oct-8-yl]-methanone | A | Mass spectrum (ESI$^+$): m/z = 392 [M + H]$^+$ |
| 137 | endo-[3-(3,4-Difluoro-phenyl)-8-aza-bicyclo[3.2.1]oct-8-yl]-(2,3-dihydro-benzo[1,4]dioxin-6-yl)-methanone | A | Mass spectrum (ESI$^+$): m/z = 392 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 138 | endo-(2,3-Dihydro-benzo[1,4]dioxin-6-yl)-(3-p-tolyl-8-aza-bicyclo[3.2.1]oct-8-yl)-methanone | A | Mass spectrum (ESI$^+$): m/z = 364 [M + H]$^+$ |
| 139 | endo-(2,3-Dihydro-benzo[1,4]dioxin-6-yl)-[3-(3-methoxy-phenyl)-8-aza-bicyclo[3.2.1]oct-8-yl]-methanone | A | Mass spectrum (ESI$^+$): m/z = 380 [M + H]$^+$ |
| 140 | endo-(2,3-Dihydro-benzo[1,4]dioxin-6-yl)-[3-(4-trifluoromethoxy-phenyl)-8-aza-bicyclo[3.2.1]oct-8-yl]-methanone | A | Mass spectrum (ESI$^+$): m/z =434 [M + H]$^+$ |
| 141 | endo-(2,3-Dihydro-benzo[1,4]dioxin-6-yl)-[3-(3-hydroxy-phenyl)-8-aza-bicyclo[3.2.1]oct-8-yl]-methanone | C | Mass spectrum (ESI$^+$): m/z = 366 [M + H]$^+$ |
| 142 | endo-(2,3-Dihydro-benzo[1,4]dioxin-6-yl)-[3-(4-hydroxy-phenyl)-8-aza-bicyclo[3.2.1]oct-8-yl]-methanone | C | Mass spectrum (ESI$^+$): m/z = 366 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 143 | endo-(2,3-Dihydro-benzo[1,4]dioxin-6-yl)-[3-(4-trimethyl-silyl-phenyl)-8-aza-bicyclo[3.2.1]oct-8-yl]-methanone | A | Mass spectrum (ESI$^+$): m/z =422 [M + H]$^+$ |
| 144 | [3-(4-Chloro-2-fluoro-phenyl)-8-aza-bicyclo[3.2.1]oct-8-yl]-(2,3-dihydro-benzo[1,4]dioxin-6-yl)-methanone | B | Mass spectrum (ESI$^+$): m/z =402/404 (Cl) [M + H]$^+$ |
| 145 | ca. 1.3:1 mixture of exo and endo isomer (2,3-Dihydro-benzo[1,4]dioxin-6-yl)-[3-(2-fluoro-phenyl)-8-aza-bicyclo[3.2.1]oct-8-yl]-methanone | B | Mass spectrum (ESI$^+$): m/z = 368 [M + H]$^+$ |
| 146 | ca. 1.1:1 mixture of exo and endo isomer, the compound was obtained as side product from the preparation of example 144<br>[3-(4-Aminomethyl-phenyl)-8-aza-bicyclo[3.2.1]oct-8-yl]-(2,3-dihydro-benzo[1,4]dioxin-6-yl)-methanone | B | Mass spectrum (ESI$^+$): m/z = 368 [M + H]$^+$ |
| 147 | ca. 2.5:1 mixture of exo and endo isomer, the compound was obtained from 4-[8-(2,3-dihydro-benzo[1,4]dioxine-6-carbonyl)-8-aza-bicyclo[3.2.1]oct-2-en-3-yl]-benzonitrile using procedure B<br>exo-[3-(3-Aminomethyl-phenyl)-8-aza-bicyclo[3.2.1]oct-8-yl]-(2,3-dihydro-benzo[1,4]dioxin-6-yl)-methanone | B | Mass spectrum (ESI$^+$): m/z = 379 [M + H]$^+$ |
| | the compound was obtained from 3-[8-(2,3-dihydro-benzo[1,4]dioxine-6-carbonyl)-8-aza-bicyclo[3.2.1]oct-2-en-3-yl]-benzonitrile using procedure B | | |

TABLE 3-continued

Compilation of synthesized end compounds

| Example No. | Chemical Name/Structure/Remarks | Prepared in analogy to Procedure | Characterization |
|---|---|---|---|
| 148 | [3-(3-Chloro-4-fluoro-phenyl)-8-aza-bicyclo[3.2.1]oct-8-yl]-(2,3-dihydro-benzo[1,4]dioxin-6-yl)-methanone<br><br>ca. 1.7:1 mixture of exo and endo isomer | B | Mass spectrum (ESI+):<br>m/z =402/404 (Cl) [M + H]+ |
| 149 | 3-[8-(2,3-Dihydro-benzo[1,4]dioxine-6-carbonyl)-8-aza-bicyclo[3.2.1]oct-3-yl]-benzamide<br><br>ca. 2.4:1 mixture of exo and endo isomer | B | Mass spectrum (ESI+):<br>m/z = 393 [M + H]+ |
| 150 | (3-Biphenyl-3-yl-8-aza-bicyclo[3.2.1]oct-8-yl)-(2,3-dihydro-benzo[1,4]dioxin-6-yl)-methanone<br><br>ca. 1:1 mixture of exo and endo isomer | B | Mass spectrum (ESI+):<br>m/z =426 [M + H]+ |
| 151 | [3-(4-Chloro-phenyl)-8-aza-bicyclo[3.2.1]oct-8-yl]-(2,3-dihydro-benzo[1,4]dioxin-6-yl)-methanone<br><br>ca. 2.6:1 mixture of exo and endo isomer | B | Mass spectrum (ESI+):<br>m/z = 384/386 (Cl) [M + H]+ |
| 152 | endo-(2,3-Dihydro-benzo[1,4]dioxin-6-yl)-[3-(4-phenoxy-phenyl)-8-aza-bicyclo[3.2.1]oct-8-yl]-methanone | A | Mass spectrum (ESI+):<br>m/z =442 [M + H]+ |

TABLE 3-continued

Compilation of synthesized end compounds

| Example No. | Chemical Name/Structure/Remarks | Prepared in analogy to Procedure | Characterization |
|---|---|---|---|
| 153 | endo-(2,3-Dihydro-benzo[1,4]dioxin-6-yl)-(3-pyridin-3-yl-8-aza-bicyclo[3.2.1]oct-8-yl)-methanone | A | Mass spectrum (ESI+): m/z = 351 [M + H]+ |
| 154 | endo-448-(2,3-Dihydro-enzo[1,4]dioxine-6-carbonyl)-8-aza-bicyclo[3.2.1]oct-3-yl]-benzoic acid methyl ester | A | Mass spectrum (ESI+): m/z = 408 [M + H]+ |
| 155 | endo-[3-(4-Bromo-phenyl)-8-aza-icyclo[3.2.1]oct-8-yl]-(2,3-dihydro-benzo[1,4]dioxin-6-yl)-methanone | D | Mass spectrum (ESI+): m/z = 428/430 (Br) [M + H]+ |
| 156 | endo-(2,3-Dihydro-benzo[1,4]dioxin-6-yl)-[3-(2-methoxy-phenyl)-8-aza-bicyclo[3.2.1]oct-8-yl]-methanone | A | Mass spectrum (ESI+): m/z = 380 [M + H]+ |
| 157 | endo-(2,3-Dihydro-benzo[1,4]dioxin-6-yl)-(3-naphthalen-2-yl-8-aza-bicyclo[3.2.1]oct-8-yl)-methanone | A | Mass spectrum (ESI+): m/z = 400 [M + H]+ |

TABLE 3-continued

Compilation of synthesized end compounds

| Example No. | Chemical Name/Structure/Remarks | Prepared in analogy to Procedure | Characterization |
|---|---|---|---|
| 158 | endo-4-[8-(2,3-Dihydro-enzo[1,4]dioxine-6-carbonyl)-8-aza-bicyclo[3.2.1]oct-3-yl]-benzoic acid | E | Mass spectrum (ESI+): m/z =408 [M + H]+ |
| 159 | endo-(2,3-Dihydro-benzo[1,4]dioxin-6-yl)-[3-(2-hydroxy-phenyl)-8-aza-bicyclo[3.2.1]oct-8-yl]-methanone | C | Mass spectrum (ESI+): m/z = 366 [M + H]+ |
| 160 | endo-[3-(2,4-Difluoro-phenyl)-8-aza-bicyclo[3.2.1]oct-8-yl]-(2,3-dihydro-benzo[1,4]dioxin-6-yl)-methanone | A | Mass spectrum (ESI+): m/z = 386 [M + H]+ |
| 161 | endo-[3-(2,6-Difluoro-phenyl)-8-aza-bicyclo[3.2.1]oct-8-yl]-(2,3-dihydro-benzo[1,4]dioxin-6-yl)-methanone | A | Mass spectrum (ESI+): m/z = 386 [M + H]+ |
| 162 | endo-(7-Difluoromethyl-5-methyl-[1,2,4]triazolo[1,5-a]pyrimidin-2-yl)-[3-(4-fluoro-phenyl)-8-aza-bicyclo[3.2.1]oct-8-yl]-methanone | A | Mass spectrum (ESI+): m/z =416 [M + H]+ |

TABLE 3-continued

Compilation of synthesized end compounds

| Example No. | Chemical Name/Structure/Remarks | Prepared in analogy to Procedure | Characterization |
|---|---|---|---|
| 163 | endo-(3,5-Dichloro-4-hydroxy-phenyl)-[3-(4-fluoro-phenyl)-8-aza-bicyclo[3.2.1]oct-8-yl]-methanone 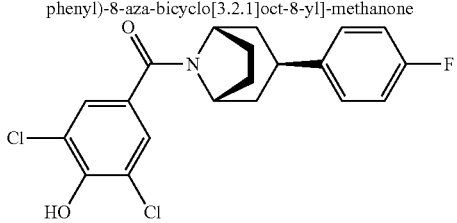 | A | LC (method 1):<br>$t_R$ = 4.07 min;<br>MS (ESI$^+$):<br>m/z = 394/396/398<br>(2Cl) [M + H]$^+$ |
| 164 | endo-[3-(4-Fluoro-phenyl)-8-aza-bicyclo[3.2.1]oct-8-yl]-(4-hydroxy-3,5-dimethyl-phenyl)-methanone 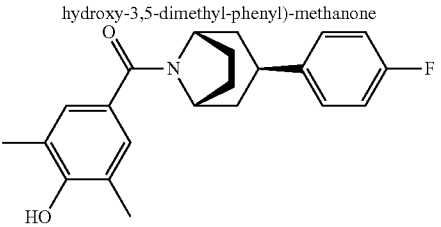 | C | LC (method 1):<br>$t_R$ = 3.91 min;<br>MS (ESI$^+$):<br>m/z = 354<br>[M + H]$^+$ |
| 165 | endo-(3-Chloro-4-methoxy-phenyl)-[3-(4-fluoro-phenyl)-8-aza-bicyclo[3.2.1]oct-8-yl]-methanone 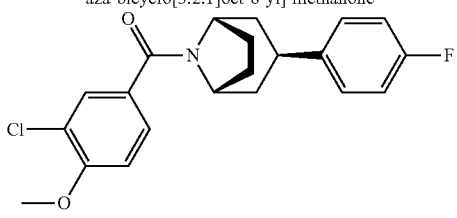 | A | LC (method 1):<br>$t_R$ = 4.34 min;<br>MS (ESI$^+$):<br>m/z = 374/376<br>(Cl) [M + H]$^+$ |
| 166 | endo-[3-(4-Fluoro-phenyl)-8-aza-bicyclo[3.2.1]oct-8-yl]-(4-hydroxy-3-methyl-phenyl)-methanone 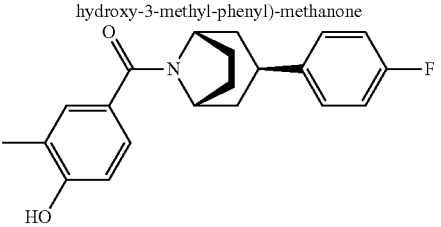 | A | LC (method 1):<br>$t_R$ = 3.71 min;<br>MS (ESI$^+$):<br>m/z = 340<br>[M + H]$^+$ |
| 167 | endo-(3-Chloro-4-hydroxy-phenyl)-[3-(4-fluoro-phenyl)-8-aza-bicyclo[3.2.1]oct-8-yl]-methanone 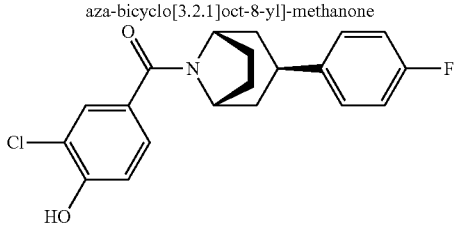 | C | LC (method 1):<br>$t_R$ = 3.79 min;<br>MS (ESI$^+$):<br>m/z = 360/362<br>(Cl) [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 168 | endo-(3,5-Difluoro-4-methoxy-phenyl)-[3-(4-fluoro-phenyl)-8-aza-bicyclo[3.2.1]oct-8-yl]-methanone | A | LC (method 1): $t_R$ = 4.01 min; MS (ESI$^+$): m/z = 376 [M + H]$^+$ |
| 169 | endo-(3-Fluoro-4-hydroxy-phenyl)-[3-(4-fluoro-phenyl)-8-aza-bicyclo[3.2.1]oct-8-yl]-methanone | A | LC (method 1): $t_R$ = 2.73 min; MS (ESI$^+$): m/z = 344 [M + H]$^+$ |
| 170 | endo-[3-(4-Fluoro-phenyl)-8-aza-bicyclo[3.2.1]oct-8-yl]-(4-methoxy-3-methyl-phenyl)-methanone | A | LC (method 1): $t_R$ = 4.43 min; MS (ESI$^+$): m/z = 354 [M + H]$^+$ |
| 171 | endo-[3-(4-Fluoro-phenyl)-8-aza-bicyclo[3.2.1]oct-8-yl]-(4-hydroxy-3-methoxy-phenyl)-methanone | A | LC (method 1): $t_R$ = 3.54 min; MS (ESI$^+$): m/z = 356 [M + H]$^+$ |
| 172 | endo-(3,5-Difluoro-4-hydroxy-phenyl)-[3-(4-fluoro-phenyl)-8-aza-bicyclo[3.2.1]oct-8-yl]-methanone | C | LC (method 1): $t_R$ = 3.72 min; MS (ESI$^+$): m/z = 362 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 173 | endo-(4-Amino-3-chloro-phenyl)-[3-(4-fluoro-phenyl)-8-aza-bicyclo[3.2.1]oct-8-yl]-methanone | A | LC (method 1): $t_R$ = 3.93 min; MS (ESI$^+$): m/z = 359/361 (Cl) [M + H]$^+$ |
| 174 | endo-[3-(4-Fluoro-phenyl)-8-aza-bicyclo[3.2.1]oct-8-yl]-(4-hydroxy-3-trifluoromethyl-phenyl)-methanone | A | LC (method 1): $t_R$ = 3.99 min; MS (ESI$^+$): m/z = 394 [M + H]$^+$ |
| 175 | endo-(3-Chloro-4-hydroxy-5-methoxy-phenyl)-[3-(4-fluoro-phenyl)-8-aza-bicyclo[3.2.1]oct-8-yl]-methanone | A | LC (method 1): $t_R$ = 3.88 min; MS (ESI$^+$): m/z = 390/392 (Cl) [M + H]$^+$ |
| 176 | endo-(4-Amino-3-fluoro-phenyl)-[3-(4-fluoro-phenyl)-8-aza-bicyclo[3.2.1]oct-8-yl]-methanone | A | LC (method 1): $t_R$ = 3.70 min; MS (ESI$^+$): m/z = 343 [M + H]$^+$ |
| 177 | endo-(4-Amino-phenyl)-[3-(4-fluoro-phenyl)-8-aza-bicyclo[3.2.1]oct-8-yl]-methanone | A | LC (method 1): $t_R$ = 3.67 min; MS (ESI$^+$): m/z = 325 [M + H]$^+$ |

TABLE 3-continued

Compilation of synthesized end compounds

| Example No. | Chemical Name/Structure/Remarks | Prepared in analogy to Procedure | Characterization |
|---|---|---|---|
| 178 | endo-(4-Amino-3,5-dichloro-phenyl)-[3-(4-fluoro-phenyl)-8-aza-bicyclo[3.2.1]oct-8-yl]-methanone 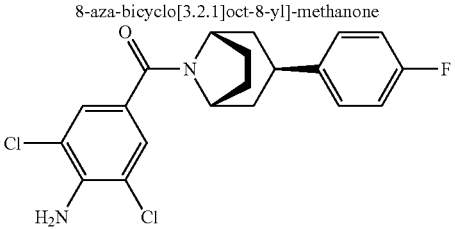 | A | LC (method 1): $t_R$ = 4.29 min; MS (ESI$^+$): m/z = 393/395/397 (2 Cl) [M + H]$^+$ |
| 179 | endo-(3-Chloro-5-fluoro-4-hydroxy-phenyl)-[3-(4-fluoro-phenyl)-8-aza-bicyclo[3.2.1]oct-8-yl]-methanone 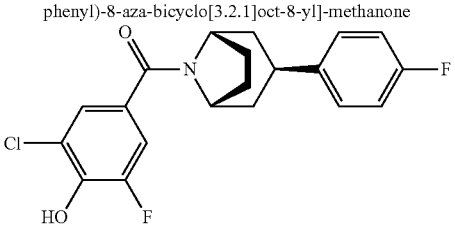 | A | LC (method 1): $t_R$ = 3.87 min; MS (ESI$^+$): m/z = 376/378 (Cl) [M + H]$^+$ |
| 180 | endo-[3-(4-Fluoro-phenyl)-8-aza-bicyclo[3.2.1]oct-8-yl]-(1H-indazol-5-yl)-methanone 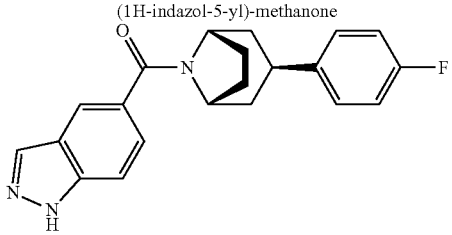 | F | LC (method 1): $t_R$ = 3.44 min; MS (ESI$^+$): m/z = 350 [M + H]$^+$ |
| 181 | endo-[3-(4-Fluoro-phenyl)-8-aza-bicyclo[3.2.1]oct-8-yl]-(4-hydroxy-3,5-dimethoxy-phenyl)-methanone 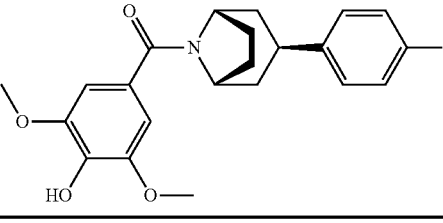 | F | LC (method 1): $t_R$ = 3.50 min; MS (ESI$^+$): m/z = 386 [M + H]$^+$ |

Some examples of formulations will now be described in which the term "active substance" denotes one or more compounds according to the invention, including the salts thereof. In the case of one of the combinations with one or additional active substances as described previously, the term "active substance" also includes the additional active substances.

Example A

Tablets Containing 100 mg of Active Substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example B

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Example C

Hard Gelatine Capsules Containing 150 mg of Active Substance

Composition:

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories Containing 150 mg of Active Substance

Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

Ampoules Containing 10 mg Active Substance

Composition:

| active substance | 10.0 mg |
|---|---|
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

Example F

Ampoules Containing 50 mg of Active Substance

Composition:

| active substance | 50.0 mg |
|---|---|
| 0.01N hydrochloric acid | q.s. |
| double-distilled water | ad 10.0 mL |

Preparation:

The active substance is dissolved in the necessary amount of 0.01 N HCl, made isotonic with common salt, filtered sterile and transferred into 10 mL ampoules.

The invention claimed is:

1. A compound of formula (I)

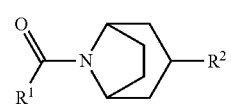

I wherein
R$^1$ denotes
pyrrolyl, furanyl, thienyl, pyridinyl, indolyl, benzofuranyl, benzothiophenyl, quinolinyl, isoquinolinyl,
pyrrolyl, imidazolyl, furanyl, thienyl, pyridinyl, in each of which one or two CH groups are replaced by N,
indolyl, benzofuranyl, benzothiophenyl, quinolinyl, isoquinolinyl, in each of which 1 to 3 CH groups are replaced by N, or
pyrazolopyrimidinyl, triazolopyrimidinyl,
while in the above-mentioned N-heteroaromatic groups one or two —N=CH— groups are optionally replaced by —NH—CO— and/or —N($C_{1-4}$-alkyl)-CO—, and
while the above-mentioned polycyclic heteroaromatic groups may be partially saturated, though, retaining an aromatic or heteroaromatic substructure that is attached to the carbonyl group in formula I,
where in the partially saturated rings one or two CH$_2$ groups are optionally replaced independently by oxygen, sulfur, NH, N($C_{1-4}$-alkyl), carbonyl, or sulfonyl,
wherein the above-mentioned heteroaromatic and partially saturated heteroaromatic groups are optionally substituted with one or more, preferably one to four, substituents R$^4$, and wherein 2 adjacent C-atoms of each of said rings are optionally substituted with R$^5$ and R$^6$, and
wherein all heteroaromatic rings are attached to the carbonyl group in formula I via a carbon atom,
R$^2$ denotes phenyl, naphthyl,
while the above-mentioned aromatic groups are optionally substituted with one or more, preferably one to four, substituents R$^7$,
R$^4$ independently of each other denotes halogen, $C_{1-6}$-alkyl, $C_{2-6}$-alkenyl, $C_{2-6}$-alkynyl, hydroxy, $C_{1-4}$-alkyloxy,
nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyl-oxy-carbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl,
$C_{1-3}$-alkyl-carbonylamino, (het)aryl-carbonylamino, (het)aryl-$C_{1-3}$-alkyl-carbonyl-amino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonyl-amino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonyl-amino) carbonylamino, (het)arylsulfonylamino, (het)aryl-$C_{1-3}$-alkyl-sulfonylamino,
N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino,
N-($C_{1-3}$-alkyl)-$C_{1-3}$-alkyl-sulfonylamino, N-($C_{1-3}$-alkyl)-(het)arylsulfonylamino, N-($C_{1-3}$-alkyl)-(het)aryl-$C_{1-3}$-alkyl-sulfonylamino,
oxo-imidazolidin-1-yl, 2,4-dioxo-imidazolidin-1-yl, 2,5-dioxo-imidazolidin-1-yl, 2-oxo-hexahydropyrimidin-1-yl, wherein the nitrogen atom in position 3 of the aforementioned groups is optionally substituted with methyl or ethyl,
1,1-dioxothiazinanyl,
cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)aryl-aminocarbonyl, N-($C_{1-3}$-alkyl)-(het)arylaminocarbonyl, (het)aryl-$C_{1-3}$-alkylaminocarbonyl, N ($C_{1-3}$-alkyl)-(het)aryl-$C_{1-3}$-alkylaminocarbonyl,
$C_{1-4}$-alkyl-carbonyl, (het)aryl-carbonyl,
$C_{1-3}$-alkylcarbonyl-$C_{1-3}$-alkyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl,
carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyl-oxy, piperazin-1-yl-carbonyl-$C_{1-3}$-alkyloxy, 4-($C_{1-3}$-alkyl)-piperazin-1-yl-carbonyl-$C_{1-3}$-alkyloxy,
hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl,
$C_{1-3}$-alkylcarbonylamino-$C_{1-3}$-alkyl, arylcarbonylamino-$C_{1-3}$-alkyl,
hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkylsulfinyl, $C_{1-3}$-alkylsulfonyl, $C_{1-3}$-alkylsulfonyloxy, (het)arylsulfonyl, (het)arylsulfonyloxy, trifluoromethylsulfanyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, thietan-3-yloxy, while the above-mentioned $C_{3-n}$-cycloalkyl and $C_{3-n}$-cycloheteroalkyl groups are optionally substituted with one or two groups selected from fluorine, $C_{1-3}$-alkyl, $C_{1-3}$-alkoxy, $C_{1-3}$-alkoxy-$C_{1-3}$-alkyl, or hydroxy, and wherein one $CH_2$ group is optionally replaced by CO or $SO_2$, and $R^5$ and $R^6$ are linked to each other and bound to adjacent carbon atoms and form together a methylenedioxy, ethylenedioxy, or $C_{3-5}$-alkylene bridging group, which is optionally mono- or disubstituted with fluorine and/or methyl; or $R^5$ and $R^6$ may form combined with the carbon atoms they are attached to a benzo, pyrido, pyrimido, pyrrolo, furano, thieno, pyrazolo, imidazo, oxazolo, thiazolo, isoxazolo, or isothiazolo ring, wherein each of said rings is optionally substituted with one or more, preferably one to four, substituents independently of each other selected from halogen, $C_{1-3}$-alkyl, trifluoromethyl, amino, $C_{1-3}$-alkylamino, di-($C_{1-3}$-alkyl)amino, $C_{1-3}$-alkylcarbonylamino, hydroxy, cyano, carboxy, $C_{1-3}$-alkyloxycarbonyl and $C_{1-3}$-alkyloxy, $R^7$ independently of each other denotes halogen, nitro, cyano, hydroxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, (het)aryl, (het)aryloxy, $C_{1-6}$-alkyl, $C_{2-6}$-alkenyl, $C_{2-6}$-alkynyl, $C_{1-4}$-alkyloxy, where in each group optionally one $CH_2$ group is replaced by carbonyl or sulfonyl and each of which is optionally mono- or polyfluorinated and optionally mono- or disubstituted with hydroxy, chlorine, $C_{1-3}$-alkyloxy, amino, $C_{1-3}$-alkylamino, di-($C_{1-3}$-alkyl)-amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 2-oxo-4-($C_{1-3}$-alkyl)-piperazin-1-yl, 3-oxo-4-($C_{1-3}$-alkyl)-piperazin-1-yl, carboxy, $C_{1-3}$-alkyloxy-carbonyl, cyano, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, $C_{1-3}$-alkyl-carbonylamino, arylcarbonylamino, $C_{1-3}$-alkylsulfanyl, $C_{1-3}$-alkylsulfinyl, $C_{1-3}$-alkylsulfonyl, $C_{3-6}$-cycloalkyl, (het)aryl, or (het)aryloxy;

amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-4}$-alkyl-carbonylamino, (het)aryl-carbonylamino, (het)aryl-$C_{1-3}$-alkyl-carbonyl-amino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonyl-amino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, aminosulfonylamino, $C_{1-3}$-alkylamino-sulfonylamino, di-($C_{1-3}$-alkyl)amino-sulfonylamino, pyrrolidin-1-yl-sulfonylamino, piperidin-1-yl-sulfonylamino, morpholin-4-yl-sulfonylamino, piperazin-1-yl-sulfonylamino, 4-($C_{1-3}$-alkyl)-piperazin-1-yl-sulfonylamino, ($C_{1-3}$-alkyloxy-carbonyl-amino)carbonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, N N-($C_{1-3}$-alkyl)-(het)aryl-$C_{1-3}$-alkyl-sulfonylamino, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)aryl-aminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-3}$-alkylsulfanyl, $C_{1-3}$-alkysulfinyl, (het)arylsulfonyl, trifluoromethylsulfanyl, trifluoromethylsulfinyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, wherein the above-mentioned $C_{3-n}$-cycloalkyl and $C_{3-n}$-cycloheteroalkyl groups are optionally substituted with one or two groups selected from fluorine, $C_{1-3}$-alkyl, $C_{1-3}$-alkoxy, $C_{1-3}$-alkoxy-$C_{1-3}$-alkyl, or hydroxy, and wherein one $CH_2$ group is optionally replaced by CO or $SO_2$, and $R^{11}$ independently of each other denotes halogen, $C_{1-4}$-alkyl, difluoromethyl, trifluoromethyl, cyano, nitro, amino, $C_{1-3}$-alkylcarbonylamino, $C_{1-3}$-alkylsulfonylamino, carboxy, $C_{1-4}$-alkyloxycarbonyl, aminocarbonyl, $C_{1-3}$-alkylaminocarbonyl, di-($C_{1-3}$-alkyl)-aminocarbonyl, aminosulfonyl, $C_{1-3}$-alkylaminosulfonyl, di-($C_{1-3}$-alkyl)-aminosulfonyl, $C_{1-3}$-alkylsulfanyl, $C_{1-3}$-alkylsulfinyl, $C_{1-3}$-alkylsulfonyl, hydroxy, $C_{1-3}$-alkyloxy, difluoromethoxy, trifluoromethoxy, phenyl, while the above-mentioned (het)aryl is phenyl, naphthyl, pyrrolyl, furanyl, thienyl, pyridyl, indolyl, benzofuranyl, benzothiophenyl, quinolinyl, isoquinolinyl, or pyrrolyl, furanyl, thienyl, imidazolyl, pyridyl in which 1 or 2 CH are replaced by N, or indolyl, benzofuranyl, benzothiophenyl, quinolinyl, isoquinolinyl in which 1 to 3 CH are replaced by N, or a ring selected from the group consisting of 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl and 3,4-dihydro-3-oxo-2H-benzo[1,4]oxazinyl, wherein each (het)aryl is optionally substituted with 1, 2, or 3 $R^{11}$ which may be identical or different, whilst the above-mentioned alkyl or alkylene moieties may be branched or unbranched, or a tautomer thereof, a stereoisomer thereof, a mixture thereof, or a salt thereof.

2. The compound according to claim 1, wherein $R^1$ denotes pyrrolyl, furanyl, thienyl, pyridinyl, indolyl, benzofuranyl, benzothiophenyl, quinolinyl, isoquinolinyl, or pyrrolyl, furanyl, thienyl, pyridinyl, in each of which 1 or 2 CH are replaced by N, or indolyl, benzofuranyl, benzothiophenyl, quinolinyl, isoquinolinyl, in each of which 1 or 2 CH are replaced by N, or indolinyl, 2-oxo-2,3-dihydro-indolyl, 1-oxo-2,3-dihydro-isoindolyl, 2-oxo-2,3-dihydro-benzoimidazolyl, pyrazolo[1,5-a]pyrimidinyl, 7-oxo-4,7-dihydro-pyrazolo[1,5-a]pyrimidinyl, [1,2,4]-triazolo[1,5-a]pyrimidinyl, 4-oxo-3,4-dihydro-quinazolinyl, tetrahydroquinolinyl, wherein the above-mentioned heteroaromatic groups are optionally substituted with one or more, preferably one to four, substituents $R^4$ and wherein 2 adjacent C-atoms are optionally substituted with $R^5$ and $R^6$, or a pharmaceutically acceptable salt thereof.

3. The compound according to claim 1, wherein $R^1$ denotes furanyl, thienyl, pyrazolyl, oxazolyl, thiazolyl, isothiazolyl, [1,2,5]-thiadiazolyl, pyridinyl, pyrimidinyl, pyrazinyl, pyridazinyl, benzofuranyl, indolyl, indolinyl, 2-oxo-2,3-dihydro-indolyl, 1-oxo-2,3-dihydro-isoindolyl, indazolyl, benzimidazolyl, 2-oxo-2,3-dihydro-1H-benzoimidazolyl, benzoxazolyl, benzotriazolyl, benzothiazolyl, pyrazolo[1,5-a]pyrimidinyl, 7-oxo-4,7-dihydro-pyrazolo[1,5-a]pyrimidinyl, quinoxalinyl, quinolinyl, isoquinolinyl, quinazolinyl, 4-oxo-3,4-dihydro-quinazolinyl, naphthyridinyl, and 1,2,3,4-tetrahydroquinolinyl, each of these groups is optionally substituted with one or more, preferably one to four, substituents $R^4$ and/or at 2 adjacent C-atoms with $R^5$ and $R^6$, or a pharmaceutically acceptable salt thereof.

4. The compound according to claim 1, wherein $R^1$ denotes furanyl, thienyl, pyrazolyl, thiazolyl, pyridinyl, benzofuranyl, indolyl, indolinyl, 2-oxo-2,3-dihydro-1H-indolyl, 1-oxo-2,3-dihydro-1H-isoindolyl, indazolyl, benzimidazolyl, 2-oxo-2,3-dihydro-1H-benzoimidazolyl, benzotriazolyl, benzothiazolyl, quinoxalinyl, quinolinyl, isoquinolinyl, 4-oxo-3,4-dihydro-quinazolinyl, and 1,2,3,4-tetrahydroquinolinyl, each of these groups is optionally substituted with one to four substituents $R^4$ and/or at 2 adjacent C-atoms with $R^5$ and $R^6$, or a pharmaceutically acceptable salt thereof.

5. The compound according to claim 1, wherein $R^1$ denotes benzofuranyl, indolyl, 2-oxo-2,3-dihydro-1H-indolyl, indazolyl, benzimidazolyl, benzotriazolyl, benzothiazolyl, quinoxalinyl, quinolinyl, and 1,2,3,4-tetrahydroquinolinyl, each of these groups is optionally substituted with one, two, or three substituents $R^4$ or optionally substituted with one or two substituents $R^4$ and/or at 2 adjacent C-atoms with $R^5$ and $R^6$, or a pharmaceutically acceptable salt thereof.

6. The compound according to claim 1, wherein $R^2$ denotes phenyl and naphthyl while all the above-mentioned aromatic rings are optionally substituted with one to four $R^7$, or a pharmaceutically acceptable salt thereof.

7. The compound according to claim 1, wherein $R^2$ denotes phenyl or naphthyl, each of these groups may be substituted with one, two, or three $R^7$, or a pharmaceutically acceptable salt thereof.

8. The compound according claim 1, wherein $R^2$ denotes phenyl or naphthyl that are optionally substituted with one, two, or three $R^7$, or a pharmaceutically acceptable salt thereof.

9. The compound according to claim 1, wherein $R^2$ denotes phenyl optionally substituted with one or two $R^7$, or a pharmaceutically acceptable salt thereof.

10. The compound according to claim 1, wherein $R^4$ denotes fluorine, chlorine, bromine, $C_{1-4}$-alkyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonyl-amino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, $C_{1-3}$-alkyl-sulfonylamino, (het)arylsulfonylamino, (het)aryl-$C_{1-3}$-alkyl-sulfonylamino, N-($C_{1-3}$-alkyl)-$C_{1-3}$-alkyl-carbonylamino, N-($C_{1-3}$-alkyl)-(het)arylcarbonylamino, N N-($C_{1-3}$-alkyl)-(het)aryl-$C_{1-3}$-alkyl-carbonylamino, N-($C_{1-3}$-alkyl)-$C_{1-3}$-alkyloxy-carbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, N-($C_{1-3}$-alkyl)-(het)aryl-$C_{1-3}$-alkyl-sulfonylamino, oxo-imidazolidinyl, 2,4-dioxo-imidazolidinyl, 2,5-dioxo-imidazolidin-1-yl, 2-oxo-hexahydropyrimidin-1-yl, wherein the nitrogen atom in position 3 of the aforementioned groups is optionally substituted with methyl, 1,1-dioxo-[1,2]thiazinan-2-yl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl, 4-($C_{1-3}$-alkyl)-piperazin-1-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy, 4-($C_{1-3}$-alkyl)-piperazin-1-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, (methyl-morpholin-4-yl)-$C_{1-3}$-alkyl, (dimethyl-morpholin-4-yl)-$C_{1-3}$-alkyl, 3-oxo-morpholin-4-yl-$C_{1-3}$-alkyl, piperazin-1-yl-$C_{1-3}$-alkyl, 2-oxo-piperazin-1-yl-$C_{1-3}$-alkyl, 3-oxo-piperazin-1-yl-$C_{1-3}$-alkyl, 4-($C_{1-3}$-alkyl)-piperazin-1-yl-$C_{1-3}$-alkyl, 2-oxo-4-($C_{1-3}$-alkyl)-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, piperazin-1-yl-$C_{1-3}$-alkyloxy, 2-oxo-piperazin-1-yl-$C_{1-3}$-alkyloxy, 3-oxo-piperazin-1-yl-$C_{1-3}$-alkyloxy, 4-($C_{1-3}$-alkyl)-piperazin-1-yl-$C_{1-3}$-alkyloxy, 2-oxo-4-($C_{1-3}$-alkyl)-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, piperazin-1-yl-sulfonyl, 4-($C_{1-3}$-alkyl)-piperazin-1-yl-sulfonyl, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yl-oxy, tetrahydropyran-3-yl-oxy, tetrahydropyran-4-yl-oxy, tetrahydrofuranyl-$C_{1-3}$-alkyloxy, tetrahydropyranyl-$C_{1-3}$-alkyloxy, thietan-3-yloxy, wherein the above-mentioned (het)aryl groups are phenyl, naphthyl, or pyrrolyl, furanyl, thienyl, pyridyl, indolyl, benzofuranyl, benzothiophenyl, quinolinyl, isoquinolinyl, or pyrrolyl, furanyl, thienyl, imidazolyl, pyridyl, wherein 1 or 2 CH are replaced by N, or indolyl, benzofuranyl, benzothiophenyl, quinolinyl, isoquinolinyl, wherein 1 to 3 CH are replaced by N, or 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quino-linyl, 1,2-dihydro-1-oxo-isoquinolinyl, 1,4-dihydro-4-oxo-cinnolinyl, 1,2-dihydro-2-oxo-quinazolinyl, 1,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-3-oxo-quinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, coumarinyl, 2,3-dihydro-benzo[1,4]dioxinyl, 3,4-dihydro-3-oxo-2H-benzo[1,4]oxazinyl, and wherein all the above-mentioned (het)aryl groups are optionally substituted with 1, 2, or 3 $R^{11}$ which may be identical or different, or a pharmaceutically acceptable salt thereof.

11. The compound according to claim 1, wherein $R^4$ denotes fluorine, chlorine, bromine, $C_{1-4}$-alkyl, hydroxy, $C_{1-4}$-alkyloxy, thietan-3-yloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonyl-amino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, 2-oxo-imidazolidinyl, 1,1-dioxo-[1,2]thiazinanyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, N-($C_{1-3}$-alkyl)-(het)arylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, $C_{1-4}$-alkylsulfonyl, aminosulfonyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, (het)aryl, (het)aryl-$C_{1-3}$-alkyl or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, imidazolyl, or pyridyl, wherein 1 or 2 CH are replaced by N, or indolyl, benzofuranyl, benzothiophenyl, quinolinyl, or isoquinolinyl, wherein 1 to 3 CH are replaced by N, and wherein the above-mentioned (het)aryl groups may be substituted with 1, 2, or 3 $R^{11}$ which may be identical or different, or a pharmaceutically acceptable salt thereof.

12. The compound according to claim 1, wherein $R^4$ denotes fluorine, chlorine, $C_{1-4}$-alkyl, difluoromethyl, trifluoromethyl, hydroxy, $C_{1-4}$-alkyloxy, difluoromethoxy, trifluoromethoxy, thietan-3-yloxy, amino, $C_{1-3}$-alkylamino, di-($C_{1-3}$-alkyl)amino, pyrrolidin-1-yl, piperidin-1-yl, morpholin-4-yl, $C_{1-3}$-alkyl-carbonylamino, $C_{1-4}$-alkylcarbonyl, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, 2-oxo-pyrrolidin-1-yl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, morpholin-4-yl-$C_{1-3}$-alkyl, $C_{1-3}$-alkylcarbonyl-$C_{1-3}$-alkyl, $C_{1-3}$-alkylcarbonylamino-$C_{1-3}$-alkyl, 1,1-dioxo[1,2]thiazinan-2-yl, 2-oxo-imidazolidinyl, $C_{1-4}$-alkylsulfonyl, aminosulfonyl, phenyl, pyrazolyl, oxazolyl, [1,2,4]oxadiazol-3-yl, or tetrazol-1-yl, while the aromatic and heteroaromatic groups listed may be substituted with 1, 2, or 3 groups $R^{11}$ which may be identical or different, or a pharmaceutically acceptable salt thereof.

13. The compound according to claim 1, wherein $R^4$ denotes fluorine, chlorine, methyl, ethyl, iso-butyl, tert-butyl, difluoromethyl, trifluoromethyl, hydroxy, methoxy, tert-butyloxy, thietan-3-yloxy, amino, methylamino, acetylamino, hydroxymethyl, acetylaminomethyl, carboxy, cyano, methoxycarbonyl, aminocarbonyl, methylaminocarbonyl, 2-oxo-pyrrolidin-1-yl, methylcarbonyl, 2-oxo-imidazolidinyl, methylsulfonyl, aminosulfonyl, phenyl, pyrazol-3-yl, oxazol-5-yl, 5-methyl-[1,2,4]oxadiazol-3-yl, tetrazol-1-yl, or tetrazol-5-yl, or a pharmaceutically acceptable salt thereof.

14. The compound according to claim 1, wherein $R^7$ denotes halogen, $C_{1-6}$-alkyl, $C_{2-6}$-alkenyl, $C_{2-6}$-alkynyl, hydroxy, $C_{1-4}$-alkyloxy, nitro, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)aryl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, $C_{1-3}$-alkyl-sulfonylamino, $C_{1-3}$-alkyl-amino-sulfonylamino, di-($C_{1-3}$-alkyl)amino-sulfonylamino, pyrrolidin-1-yl-sulfonyl-amino, piperidin-1-yl-sulfonylamino, morpholin-4-yl-sulfonylamino, (het)aryl-sulfonylamino, N-($C_{1-3}$-alkyl)-$C_{1-3}$-alkyl-carbonylamino, N-($C_{1-3}$-alkyl)-(het)arylcarbonylamino, N-($C_{1-3}$-alkyl)-$C_{1-3}$-alkyloxycarbonylamino, N-(aminocarbonyl)-$C_{1-3}$-alkylamino, N-($C_{1-3}$-alkyl-aminocarbonyl)-$C_{1-3}$-alkylamino, N-[di-($C_{1-3}$-alkyl)aminocarbonyl]-$C_{1-3}$-alkylamino, N-($C_{1-3}$-alkyl)-$C_{1-3}$-alkyl-sulfonylamino, N-($C_{1-3}$-alkyl)-(het)arylsulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, (het)arylaminocarbonyl, N-($C_{1-3}$-alkyl)-(het)arylaminocarbonyl, (het)aryl-$C_{1-3}$-alkylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyl-oxy, piperidin-1-yl-carbonyl-$C_{1-3}$-alkyloxy, morpholin-4-yl-carbonyl-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, piperidin-1-yl-$C_{1-3}$-alkyl, 2-oxo-piperidin-1-yl-$C_{1-3}$-alkyl, morpholin-4-yl-$C_{1-3}$-alkyl, 3-oxo-morpholin-4-yl-$C_{1-3}$-alkyl, 3-oxo-piperazin-1-yl-$C_{1-3}$-alkyl, 3-oxo-4-($C_{1-3}$-alkyl)-piperazin-1-yl-$C_{1-3}$-alkyl, $C_{1-3}$-alkylcarbonylamino-$C_{1-3}$-alkyl, arylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfanyl-$C_{1-3}$-alkyloxy, $C_{1-3}$-alkylsulfinyl-$C_{1-3}$-alkyloxy, $C_{1-3}$-alkylsulfonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, 2-oxo-pyrrolidin-1-yl-$C_{1-3}$-alkyloxy, piperidin-1-yl-$C_{1-3}$-alkyloxy, 2-oxo-piperidin-1-yl-$C_{1-3}$-alkyloxy, morpholin-4-yl-$C_{1-3}$-alkyloxy, 3-oxo-morpholin-4-yl-$C_{1-3}$-alkyloxy, 3-oxo-piperazin-1-yl-$C_{1-3}$-alkyloxy, 3-oxo-4-($C_{1-3}$-alkyl)-piperazin-1-yl-$C_{1-3}$-alkyloxy, $C_{1-3}$-alkylsulfanyl, $C_{1-3}$-alkysulfinyl, $C_{1-3}$-alkylsulfonyl, (het)arylsulfonyl, trifluoromethylsulfinyl, trifluoromethylsulfonyl, aminosulfonyl, $C_{1-3}$-alkyl-aminosulfonyl, di-($C_{1-3}$-alkyl)-aminosulfonyl, pyrrolidin-1-yl-sulfonyl, piperidin-1-yl-sulfonyl, morpholin-4-yl-sulfonyl, difluoromethyl, trifluoromethyl, difluoromethoxy, trifluoromethoxy, $C_{3-6}$-cycloalkyl, $C_{3-6}$-cycloalkyloxy, $C_{3-6}$-cycloalkyl-$C_{1-3}$-alkyl, $C_{3-6}$-cycloalkyl-$C_{1-3}$-alkyloxy, (het)aryl, (het)aryloxy, (het)aryl-$C_{1-3}$-alkyl, (het)aryl-$C_{1-3}$-alkyloxy, (het)aryloxy-$C_{1-3}$-alkyl, or tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, wherein the above-mentioned (het)aryl is phenyl, naphthyl, pyrrolyl, furanyl, thienyl, pyridyl, or pyrrolyl, furanyl, thienyl, imidazolyl, pyridyl, in which 1 or 2 CH are replaced by N, and wherein the above-mentioned (het)aryl groups are optionally substituted with one or two $R^{11}$ which may be identical or different, or a pharmaceutically acceptable salt thereof.

15. The compound according to claim 1, wherein $R^7$ denotes fluorine, chlorine, bromine, $C_{1-6}$-alkyl, $C_{2-6}$-alkenyl, $C_{2-6}$-alkynyl, hydroxy, $C_{1-4}$-alkyloxy, amino, $C_{1-3}$-alkylamino, di-($C_{1-3}$-alkyl)amino, $C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, $C_{1-3}$-alkyl-sulfonylamino, N-($C_{1-3}$-alkyl)-$C_{1-3}$-alkyl-carbonylamino, N-($C_{1-3}$-alkyl)-$C_{1-3}$-alkyl-sulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfonyl, trifluoromethylsulfonyl, aminosulfonyl, $C_{1-3}$-alkyl-aminosulfonyl, di-($C_{1-3}$-alkyl)-aminosulfonyl, difluoromethyl, trifluoromethyl, difluoromethoxy, trifluoromethoxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, or phenyl or phenoxy that are optionally substituted with one or two identical or different $R^{11}$, or a pharmaceutically acceptable salt thereof.

16. The compound according to claim 1, wherein $R^7$ denotes fluorine, chlorine, bromine, $C_{1-4}$-alkyl, trifluoromethyl, hydroxy, $C_{1-4}$-alkyloxy, trifluoromethoxy, phenoxy, amino-$C_{1-3}$-alkyl, carboxy, cyano, $C_{1-3}$-alkoxycarbonyl, aminocarbonyl, $C_{1-3}$-alkyl-aminocarbonyl, di-($C_{1-3}$-alkyl)-aminocarbonyl, or phenyl, or a pharmaceutically acceptable salt thereof.

17. The compound according to claim 1, wherein $R^7$ denotes fluorine, chlorine, bromine, methyl, isopropyl, trifluoromethyl, hydroxy, methoxy, trifluoromethoxy, phenoxy, aminomethyl, carboxy, methoxycarbonyl, aminocarbonyl, or phenyl, or a pharmaceutically acceptable salt thereof.

18. The compound according to claim 1 wherein:

$R^1$ denotes furanyl, thienyl, pyrazolyl, oxazolyl, thiazolyl, isothiazolyl, [1,2,5]-thiadiazolyl, pyridinyl, pyrimidinyl, pyrazinyl, pyridazinyl, benzofuranyl, indolyl, indolinyl, 2-oxo-2,3-dihydro-indolyl, 1-oxo-2,3-dihydro-isoindolyl, indazolyl, benzimidazolyl, 2-oxo-2,3-dihydro-1H-benzoimidazolyl, benzoxazolyl, benzotriazolyl, benzothiazolyl, pyrazolo[1,5-a]pyrimidinyl, 7-oxo-4,7-dihydro-pyrazolo[1,5-a]pyrimidinyl, quinoxalinyl, quinolinyl, isoquinolinyl, quinazolinyl, 4-oxo-3,4-dihydro-quinazolinyl, naphthyridinyl, and 1,2,3,4-tetrahydroquinolinyl, each of these groups is optionally substituted with one or more, preferably one to four, substituents $R^4$ and/or at 2 adjacent C-atoms with $R^5$ and $R^6$;

$R^2$ denotes phenyl or naphthyl, each of these groups is optionally substituted with one, two, or three $R^7$;

$R^4$ denotes fluorine, chlorine, bromine, $C_{1-4}$-alkyl, hydroxy, $C_{1-4}$-alkyloxy, thietan-3-yloxy, amino, $C_{1-3}$-alkylamino, di-($C_{1-3}$-alkyl)amino, pyrrolidin-1-yl, 2-oxo-pyrrolidin-1-yl, piperidin-1-yl, 2-oxo-piperidin-1-yl, morpholin-4-yl, 3-oxo-morpholin-4-yl, piperazin-1-yl, 2-oxo-piperazin-1-yl, 3-oxo-piperazin-1-yl, 4-($C_{1-3}$-alkyl)-piperazin-1-yl, 4-($C_{1-4}$-alkylcarbonyl)-piperazin-1-yl, 4-($C_{3-6}$-cycloalkylcarbonyl)-piperazin-1-yl, 4-($C_{1-4}$-alkyloxycarbonyl)-piperazin-1-yl, 4-($C_{1-4}$-alkylsulfonyl)-piperazin-1-yl, 2-oxo-4-($C_{1-3}$-alkyl)-piperazin-1-yl, 3-oxo-4-($C_{1-3}$-alkyl)-piperazin-1-yl, $C_{1-3}$-alkyl-carbonylamino, (het)arylcarbonylamino, (het)aryl-$C_{1-3}$-alkyl-carbonyl-amino, $C_{1-3}$-alkyloxy-carbonylamino, aminocarbonylamino, $C_{1-3}$-alkyl-aminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino, 4-($C_{1-3}$-alkyl)-piperazin-1-yl-carbonylamino, 2-oxo-imidazolidinyl, 1,1-dioxo-[1,2]thiazinanyl, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, 2-(methoxymethyl)-pyrrolidin-1-yl-carbonyl, 3-(methoxymethyl)-pyrrolidin-1-yl-carbonyl, piperidin-1-yl-carbonyl, morpholin-4-yl-carbonyl, piperazin-1-yl-carbonyl, 4-($C_{1-3}$-alkyl)-piperazin-1-yl-carbonyl, N-($C_{1-3}$-alkyl)-(het)arylaminocarbonyl, N-($C_{1-3}$-alkyl)-(het)aryl-$C_{1-3}$-alkylaminocarbonyl, $C_{1-4}$-alkyl-carbonyl, (het)aryl-carbonyl, $C_{1-3}$-alkylcarbonyl-$C_{1-3}$-alkyl, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, 2-oxo-pyrrolidin-1-yl-$C_{1-3}$-alkyl, morpholin-4-yl-$C_{1-3}$-alkyl, $C_{1-3}$-alkylsulfonyl, aminosulfonyl, $C_{1-3}$-alkylcarbonylamino-$C_{1-3}$-alkyl, (het)arylcarbonylamino-$C_{1-3}$-alkyl, hydroxy-$C_{1-3}$-alkyloxy, $C_{1-3}$-alkyloxy-$C_{1-3}$-alkyloxy, difluoromethyl, trifluoromethyl, difluoromethoxy, trifluoromethoxy, 2,2,2-trifluoro-1-hydroxyethyl, 2,2,2-trifluoro-1-hydroxy-1-methylethyl, 2,2,2-trifluoro-1-hydroxy-1-(trifluoromethyl)ethyl, (het)aryl, (het)aryl-$C_{1-3}$-alkyl or (het)aryloxy, wherein the above-mentioned (het)aryl groups are phenyl, naphthyl, pyrrolyl, furanyl, thienyl, pyridyl, indolyl, benzofuranyl, benzothiophenyl, quinolinyl, and isoquinolinyl, or pyrrolyl, furanyl, thienyl, imidazolyl, or pyridyl wherein 1 or 2 CH are replaced by N, or indolyl, benzofuranyl, benzothiophenyl, quinolinyl, or isoquinolinyl wherein 1 to 3 CH are replaced by N, and wherein the above-mentioned (het)aryl groups may be substituted with 1, 2, or 3 $R^{11}$ which may be identical or different;

$R^5$ and $R^6$ form a methylenedioxy, difluoromethylenedioxy, ethylenedioxy, propylene, or butylene group;

$R^7$ denotes fluorine, chlorine, bromine, $C_{1-6}$-alkyl, $C_{2-6}$-alkenyl, $C_{2-6}$-alkynyl, hydroxy, $C_{1-4}$-alkyloxy, amino, $C_{1-3}$-alkylamino, di-($C_{1-3}$-alkyl)amino, $C_{1-3}$-alkyl-carbonylamino, $C_{1-3}$-alkyloxy-carbonylamino, aminocarbonylamino, $C_{1-3}$-alkyl-aminocarbonylamino, di-($C_{1-3}$-alkyl)aminocarbonylamino, $C_{1-3}$-alkyl-sulfonylamino, N-($C_{1-3}$-alkyl)-$C_{1-3}$-alkyl-carbonylamino, N-($C_{1-3}$-alkyl)-$C_{1-3}$-alkyl-sulfonylamino, cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, carboxy-$C_{1-3}$-alkyloxy, $C_{1-3}$-alkyloxy-carbonyl-$C_{1-3}$-alkyloxy, cyano-$C_{1-3}$-alkyloxy, hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-3}$-alkylcarbonylamino-$C_{1-3}$-alkyl, hydroxy-$C_{1-3}$-alkyloxy, $C_{1-3}$-alkyloxy-$C_{1-3}$-alkyloxy, $C_{1-3}$-alkylsulfonyl, trifluoromethylsulfonyl, aminosulfonyl, $C_{1-3}$-alkyl-aminosulfonyl, di-($C_{1-3}$-alkyl)-aminosulfonyl, difluoromethyl, trifluoromethyl, difluoromethoxy, trifluoromethoxy, $C_{3-6}$-cycloalkyl, $C_{3-6}$-cycloalkyloxy, tetrahydrofuran-3-yloxy, tetrahydropyran-3-yloxy, tetrahydropyran-4-yloxy, tetrahydrofuranyl-$C_{1-3}$-alkyloxy, tetrahydropyranyl-$C_{1-3}$-alkyloxy, or phenyl or phenoxy that are optionally substituted with one or two identical or different $R^{11}$;

$R^{11}$ denotes fluorine, methyl, methoxy, cyano, or acetylamino;

or a pharmaceutically acceptable salt thereof.

19. The compound of formula Ia

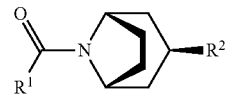

Ia wherein the residue $R^2$ occupies the endo (=trans to the $NCOR^1$ residue and cis to the ethylene bridge) position of the bicyclic structure and wherein $R^1$ and $R^2$ are defined as in claim 1, or a pharmaceutically acceptable salt thereof.

20. The compound of formula Ia

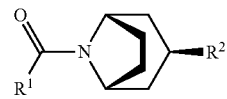

Ia wherein the residue $R^2$ occupies the endo (=trans to the $NCOR^1$ residue and cis to the ethylene bridge) position of the bicyclic structure and wherein $R^1$ and $R^2$ are defined as in claim 6, or a pharmaceutically acceptable salt thereof.

21. A physiologically acceptable salt of a compound according to claim 1 with inorganic or organic acids or bases.

22. A pharmaceutical composition containing a compound according to claim 1, or a physiologically acceptable salt with inorganic or organic acids or bases, optionally together with one or more inert carriers and/or diluents.

23. A method of treating type II diabetes, the method comprising administering to a patient in need thereof the compound of claim 1, or a physiologically acceptable salt with inorganic or organic acids or bases.

24. A process for preparing a compound of formula I according to claim 1, or a physiologically acceptable salt with inorganic or organic acids or bases, characterized in that a compound of formula II

II wherein the group $R^2$ is defined as in claim 1, is reacted with a compound of formula $R^1$—CO—Y, optionally prepared in situ from the corresponding carboxylic acid, wherein $R^1$ is defined as in claim 1 and Y is a leaving group and denotes fluorine, chlorine, bromine, cyano, $C_{1-4}$-alkoxy, $C_{2-4}$-alkenyloxy, $C_{2-4}$-alky-nyloxy, $C_{1-4}$-alkylsulfanyl, arylotriazoloxy, heteroarylotriazoloxy, hetero-N-aryl, succinyl-N-oxy, $C_{1-4}$-alkylcarbonyloxy, di-($C_{1-4}$-alkyl)-aminocarbonyloxy, pyrrolyl-carbonyloxy, piperidinylcarbonyloxy, morpholinylcarbonyloxy, tri-($C_{1-4}$-alkyl)-carb-amimidoyloxy, N,N,N',N'-tetra-($C_{1-4}$-alkyl)uronium-O-yl, N,N'-dicyclohexyluron-O-yl, di-($C_{1-4}$-alkyloxy)-phosphoryloxy, di-(di-$C_{1-4}$-alkylamino)-phosphoryloxy, dipyrrolidinyl-phosphoryloxy, aryloxy, arylsulfanyl, heterosulfanyl, or heteroaryloxy, while the alkyl, alkenyl, and alkynyl groups mentioned in the definition of the above groups, optionally are mono- or polysubstituted with fluorine, chlorine, $C_{1-3}$-alkyl, or $C_{1-3}$-alkoxy, while the aryl groups mentioned in the definition of the above groups denote phenyl or naphthyl groups and the heteroaryl groups mentioned in the definition of the above groups denote pyridinyl, pyrimidinyl, triazinyl, imidazolyl, pyrazolyl, triazolyl, tetrazolyl, whilst both the aryl and heteroaryl groups optionally are mono- or polysubstituted independently with fluorine, chlorine, bromine, $C_{1-3}$-alkyl, $C_{1-3}$-alkyloxy, nitro, cyano, or di-($C_{1-3}$-alkyl)amino groups, optionally in the presence of a base or another additive.

* * * * *

UNITED STATES PATENT AND TRADEMARK OFFICE
CERTIFICATE OF CORRECTION

PATENT NO. : 8,609,690 B2  Page 1 of 1
APPLICATION NO. : 13/059233
DATED : December 17, 2013
INVENTOR(S) : Eckhardt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 384 days.

Signed and Sealed this

Twenty-second Day of September, 2015

Michelle K. Lee
*Director of the United States Patent and Trademark Office*